(12) United States Patent
Compans et al.

(10) Patent No.: US 10,030,053 B2
(45) Date of Patent: Jul. 24, 2018

(54) IMMUNOGENIC COMPOSITIONS AND METHODS OF USE THEREOF

(71) Applicants: EMORY UNIVERSITY, Atlanta, GA (US); INSTITUTE FOR SYSTEMS BIOLOGY, Seattle, WA (US)

(72) Inventors: Richard L. Compans, Atlanta, GA (US); Baozhong Wang, Atlanta, GA (US); Jadranmka Boza, Tucker, GA (US); Ioanna Skountzou, Atlanta, GA (US); Alan A. Aderem, Seattle, WA (US)

(73) Assignees: Emory University, Atlanta, GA (US); Institute for Systems Biology, Seattle, WA (US)

( * ) Notice: Subject to any disclaimer, the term of this patent is extended or adjusted under 35 U.S.C. 154(b) by 216 days.

(21) Appl. No.: 14/621,650

(22) Filed: Feb. 13, 2015

(65) Prior Publication Data
US 2015/0183837 A1    Jul. 2, 2015

Related U.S. Application Data

(62) Division of application No. 12/808,741, filed as application No. PCT/US2008/087194 on Dec. 17, 2008, now abandoned.

(60) Provisional application No. 61/014,130, filed on Dec. 17, 2007, provisional application No. 61/078,815, filed on Jul. 8, 2008.

(51) Int. Cl.
| | |
|---|---|
| *C07K 14/005* | (2006.01) |
| *C12N 7/00* | (2006.01) |
| *A61K 39/145* | (2006.01) |
| *A61K 39/39* | (2006.01) |
| *C07K 14/255* | (2006.01) |
| *A61K 39/12* | (2006.01) |
| *A61K 39/00* | (2006.01) |

(52) U.S. Cl.
CPC ............ *C07K 14/005* (2013.01); *A61K 39/12* (2013.01); *A61K 39/145* (2013.01); *A61K 39/39* (2013.01); *C07K 14/255* (2013.01); *C12N 7/00* (2013.01); *A61K 39/00* (2013.01); *A61K 2039/5252* (2013.01); *A61K 2039/5258* (2013.01); *A61K 2039/543* (2013.01); *A61K 2039/55516* (2013.01); *C07K 2319/02* (2013.01); *C07K 2319/03* (2013.01); *C07K 2319/40* (2013.01); *C12N 2710/14043* (2013.01); *C12N 2760/16123* (2013.01); *C12N 2760/16134* (2013.01)

(58) Field of Classification Search
None
See application file for complete search history.

(56) References Cited

U.S. PATENT DOCUMENTS

| | | | |
|---|---|---|---|
| 6,077,662 A | 6/2000 | Compans | |
| 7,682,618 B2 | 3/2010 | Bavari | |
| 7,790,447 B2 * | 9/2010 | Aikawa | C12N 9/13 435/183 |
| 7,795,017 B2 | 9/2010 | Robinson | |
| 7,914,802 B2 * | 3/2011 | Rhee | A61K 39/08 424/190.1 |
| 8,703,146 B2 * | 4/2014 | Aderem | C07K 14/195 424/190.1 |
| 8,795,682 B2 * | 8/2014 | Compans | A61K 39/21 424/199.1 |
| 9,045,727 B2 * | 6/2015 | Compans | A61K 39/12 |
| 2006/0088909 A1 | 4/2006 | Compans | |
| 2006/0216702 A1 | 9/2006 | Compans | |
| 2010/0047266 A1 | 2/2010 | Haynes | |
| 2010/0196419 A1 | 8/2010 | Compans | |
| 2012/0052082 A1 | 3/2012 | Compans | |

OTHER PUBLICATIONS

Malapaka et al. (Journal of Molecular Biology, Jan. 2007, p. 1102-1116).*
Bright et al., Influenza virus-like particles elicit broader immune responses than whole virion inactivated influenza virus or recombinant hemagglutinin Vaccine 25 (2007) 3871-3878.
Galarza et al., Virus-like particle vaccine conferred complete protection against a lethal influenza virus challenge. Viral Immunol. 2005;18(2):365-72.
Honko, et al., "Flagellin is an Effective Adjuvant for Immunization Against Lethal Respiratory Challenge with Yersinia Pestis," Infection and Immunity, Feb. 2006, pp. 1113-110, vol. 74, No. 2.
Kang et al., Influenza vaccines based on virus-like particles, Virus Res. Aug. 2009;143(2):140-6.
Kim et al., "Virus-like Particles Containing Multiple M2 Extracellular Domains" Molecular Therapy vol. 21 No. 2, 485-492 Feb. 2013.
Kim et al., "Multiple heterologous M2 extracellular domains presented on virus-like particles confer broader and stronger M2 immunity than live influenza A virus infection" Antiviral Researchvol. 99, Issue 3, Sep. 2013, pp. 328-335.
Koutsky et al., "A Controlled Trial of a Human Papillomavirus Type 16 Vaccine" N Engl J Med 2002; 347:1645-1651.

(Continued)

*Primary Examiner* — Agnieszka Boesen
(74) *Attorney, Agent, or Firm* — Emory Patent Group

(57) ABSTRACT

Embodiments of the disclosure encompass compositions and methods for generating immune responses in an animal or human host. Embodiments of the compositions encompass proteins derived from the surface proteins of bacteria and protozoa, and in particular the flagellum component flagellin, and which have adjunctival properties when administered in conjunction with an immunogen. Embodiments of the compositions of the disclosure are modified to incorporate a heterologous transmembrane-cytoplasmic domain allowing the peptides to be incorporated into virus-like particles. Embodiments of the methods of generating an immunological response in an animal or human comprise exposing the immune system of an animal or human host to an immunogen and a virus-like particle comprising an adjuvant polypeptide including a host cell Toll-like receptor ligand polypeptide having a transmembrane-cytoplasmic tail polypeptide, and a heterologous signal peptide.

6 Claims, 25 Drawing Sheets

(56) References Cited

OTHER PUBLICATIONS

Leclerc et al., Proteasome-Independent Major Histocompatibility Complex Class I Cross-Presentation Mediated by Papaya Mosaic Virus-Like Particles Leads to Expansion of Specific Human T Cells, Journal of Virology, 2007, 81(3) 1319-1326.

Matassov et al. "A novel intranasal virus-like particle (VLP) vaccine designed to protect against the pandemic 1918 influenza A virus (H1N1)" Viral Immunol. 2007, 20(3):441-52.

Ogushi et al., "*Salmonella enteritidis* FliC (flagella filament protein) induces human beta-defensin-2 mRNA production by Caco-2 cells." J Biol Chem. 2001, 276(32):30521-6.

Pushko et al., Influenza virus-like particles comprised of the HA, NA, and M1 proteins of H9N2 influenza virus induce protective immune responses in BALB/c mice. Vaccine 23 (2005) 5751-5759.

Quan et al., "Virus-like particle vaccine induces protective immunity against homologous and heterologous strains of influenza virus." J Virol. 2007, 81(7):3514-24.

Revaz et al. "Humoral and cellular immune responses to airway immunization of mice with human papillomavirus type 16 virus-like particles and mucosal adjuvants" Antivir. Res. 76 (1) (2007) 75-85.

Skountzou et al., "Incorporation of Glycosylphosphatidylinositol-Anchored Granulocyte-Macrophage Colony-Stimulating Factor or CD40 Ligand Enhances Immunogenicity of Chimeric Simian Immunodeficiency Virus-Like Particles" J. Virol. 2007, 81(3):1083-1094.

Song et al., "Influenza virus-like particles containing M2 induce broadly cross protective immunity." PLoS One. 2011, 6(1):e14538.

Wang et al., "Intranasal immunization with influenza VLPs incorporating membrane-anchored flagellin induces strong heterosubtypic protection." PLoS One. Nov. 29, 2010;5(11):e13972.

Wang et al. "Enhanced Influenza Virus-Like Particle Vaccines Containing the Extracellular Domain of Matrix Protein 2 and a Toll-Like Receptor Ligand" Clin Vaccine Immunol, 2012, 19(8):1119-25.

Wang et al., "Nanoclusters self-assembled from conformation-stabilized influenza M2e as broadly cross-protective influenza vaccines" Nanomedicine. 2013.

Wang et al., "Virus-Like Particles Containing the Tetrameric Ectodomain of Influenza Matrix Protein 2 and Flagellin Induce Heterosubtypic Protection in Mice" BioMed Research International vol. 2013, Article ID 686549.

\* cited by examiner

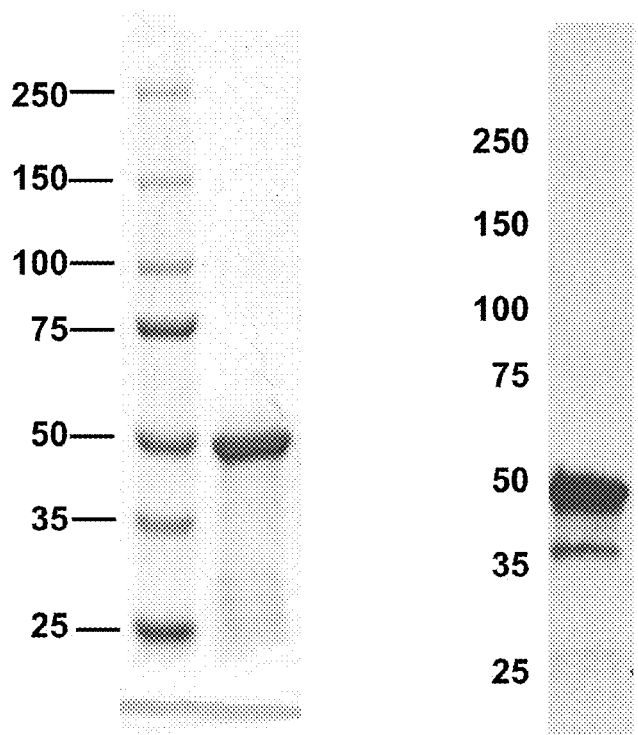
*Fig. 1A*  *Fig. 1B*
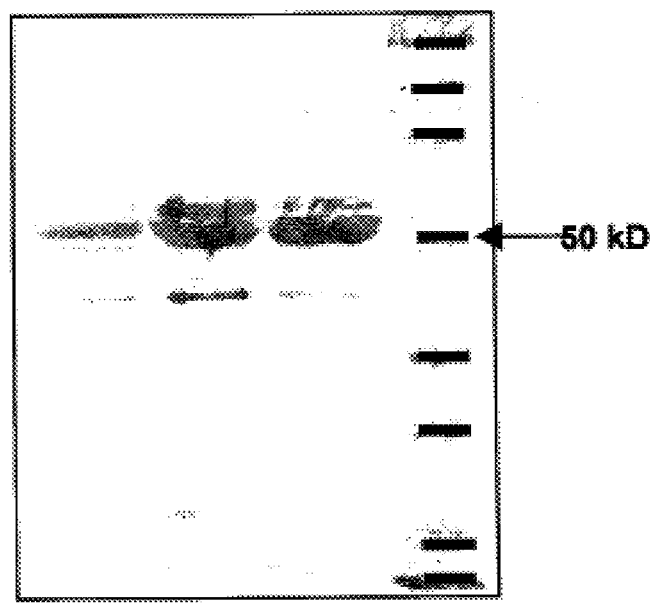
*Fig. 2*

```
         1                495
   fliC □─────────────────□
Chimeric ■─────────────────▨▨
  fliC
  Mellitin SP    HA TM      HA CT
      ■           ▨           ▨
```

*Fig. 5*

SEQ ID NO.: 1

GGTTCTAGAATGAAATTCTTAGTC

SEQ ID NO.: 2

GTGGGATCCT TTCATGTTGATCGG

SEQ ID NO.: 3

GCAGGATCCATGGCACAAGTCAT

SEQ ID NO.: 4

CGCGAATTCACGCAGTAAAGAGAG

SEQ ID NO.: 5

GCTAGAATTCCAGATTCTGGCGATC

SEQ ID NO.: 6

GCTAGGGCCCTTATCAGATGCATATTCT

SEQ ID NO.: 7

GCTCGTCGACATGAAATTCTTAG

SEQ ID NO.: 8
GCTACTCGAGTTATCAGATGCATATTC

*Fig. 6*

SEQ ID NO.: 9
<u>ATGAAATTCTTAGTCAACGTTGCCCTTGTTTTTATGGTCGTGTACATTTCTTACATCTAT
GCGGACCCGATCAACATGACCGGATCC</u>atggcacaagtcattaatacaaacagcctgtcg
ctgttgacccagaataacctgaacaaatcccagtccgctctgggcaccgctatcgagcgt
ctgtcttccggtctgcgtatcaacagcgcgaaagacgatgcggcaggtcaggcgattgct
aaccgttttaccgcgaacatcaaaggtctgactcaggcttcccgtaacgctaacgacggt
atctccattgcgcagaccactgaaggcgcgctgaacgaaatcaacaacaacctgcagcgt
gtgcgtgaactggcggttcagtctgctaacagcaccaactcccagtctgacctcgactcc
atccaggctgaaatcacccagcgcctgaacgaaatcgaccgtgtatccggccagactcag
ttcaacggcgtgaaagtcctggcgcaggacaacaccctgaccatccaggttggtgccaac
gacggtgaaactatcgatatcgatctgaagcagatcaactctcagaccctgggtctggat
acgctgaatgtgcaacaaaatataaggtcagcgatacggctgcaactgttacaggatat
gccgatacaacgattgctttagacaatagtacttttaaagcctcggctactggtcttggt
ggtactgaccagaaaattgatggcgatttaaaatttgatgatacgactggaaaatattac
gccaaagttaccgttacgggggggaactggtaaagatggctattatgaagtttccgttgat
aagacgaacggtgaggagactcttgctggcggtgcgacttcccgcttacaggtggacta
cctgcgacagcaactgaggatgtgaaaaatgtacaagttgcaaatgctgatttgacagag
gctaaagccgcattgacagcagcaggtgttaccggcacagcatctgttgttaagatgtct
tatactgataataacggtaaaactattgatggtggtttagcagttaaggtaggcgatgat
tactattctgcaactcaaaataaagatggttccataagtattaatactacgaaatacact
gcagatgacggtacatccaaaactgcactaaacaaactgggtgacgcagacggcaaaacc
gaagttgtttctattggtggtaaaacttacgctgcaagtaaagccgaaggtcacaacttt
aaagcacagcctgatctggcggaagcggctgctacaaccaccgaaaacccgctgcagaaa
attgatgctgctttggcacaggttgacacgttacgttctgacctgggtgcggtacagaac
cgtttcaactccgctattaccaacctgggcaacaccgtaaacaacctgacttctgcccgt
agccgtatcgaagattccgactacgcgaccgaagtttccaacatgtctcgcgcgcagatt
ctgcagcaggccggtacctccgttctggcgcaggcgaaccaggttccgcaaaacgtcctc
tctttactgcgtgaattccagattctggcgatctactcaactgtcgccagttcactggtg
cttttggtctccctgggggcaatcagtttctggatgtgttctaatggatctttgcagtgc
agaatatgcatctga

*Fig. 7*

SEQ ID NO.: 10

MKFLVNVALVFMVVYISYIYADPINMTGSMAQVINTNSLSLLTQNNLNKSQSALGTAIERLS
SGLRINSAKDDAAGQAIANRFTANIKGLTQASRNANDGISIAQTTEGALNEI

NNNLQRVRELAVQSANSTNSQSDLDSIQAEITQRLNEIDRVSGQTQFNGVKVLAQDN

TLTIQVGANDGETIDIDLKQINSQTLGLDTLNVQQKYKVSDTAATVTGYADTTIALDNSTFK
ASATGLGGTDQKIDGDLKFDDTTGKYYAKVTVTGGTGKDGYYEVSVDKTNGE

ETLAGGATSPLTGGLPATATEDVKNVQVANADLTEAKAALTAAGVTGTASVVKMSYTDNNGK
TIDGGLAVKVGDDYYSATQNKDGSISINTTKYTADDGTSKTALNKLGDADGKTEVVSIGGKT
YAASKAEGHNFKAQPDLAEAAATTTENPLQKIDAALAQVDTLRSDLG

AVQNRFNSAITNLGNTVNNLTSARSRIEDSDYATEVSNMSRAQILQQAGTSVLAQAN

QVPQNVLSLLREFQILAIYSTVASSLVLLVSLGAISFWMCSNGSLQCRICI

SEQ ID NO.: 11
IYSTVASSL

SEQ ID NO.: 12
LYEKVKSQL

SEQ ID NO.: 13
SFERFEIFPKE

SEQ ID NO.: 14
HNTNGVTAACSH

SEQ ID NO.: 15
CPKYVRSAKLRM

SEQ ID NO.: 16
KLKNSYVNKKGK

SEQ ID NO.: 17
NAYVSVVTSKYNRRF

SEQ ID NO.: 18
GAPVYPYDVPDYASPW

SEQ ID NO.: 19
VDHMAAAASLLTEVETPIRNEWGSRSNDSSDPAAGTSAAASLLTEVETPIRNEWGSRSNDSS
DPAAALQAAASLLTEVETPIRNEWGSRSNDSSDPAAAACAAASLLTEVETPIRNEWGSRSND
SSDPAAAAAKL

*Fig. 17*

```
                        SEQUENCE LISTING

<160> NUMBER OF SEQ ID NOS: 19

<210> SEQ ID NO 1
<211> LENGTH: 24
<212> TYPE: DNA
<213> ORGANISM: Artificial Sequence
<220> FEATURE:
<223> OTHER INFORMATION: Forward primer

<400> SEQUENCE: 1
ggttctagaa tgaaattctt agtc                                              24

<210> SEQ ID NO 2
<211> LENGTH: 24
<212> TYPE: DNA
<213> ORGANISM: Artificial Sequence
<220> FEATURE:
<223> OTHER INFORMATION: Reverse primer

<400> SEQUENCE: 2
gtgggatcct ttcatgttga tcgg                                              24

<210> SEQ ID NO 3
<211> LENGTH: 23
<212> TYPE: DNA
<213> ORGANISM: Artificial Sequence
<220> FEATURE:
<223> OTHER INFORMATION: Forward primer

<400> SEQUENCE: 3
gcaggatcca tggcacaagt cat                                               23

<210> SEQ ID NO 4
<211> LENGTH: 24
<212> TYPE: DNA
<213> ORGANISM: Artificial Sequence
<220> FEATURE:
<223> OTHER INFORMATION: Reverse primer

<400> SEQUENCE: 4
cgcgaattca cgcagtaaag agag                                              24

<210> SEQ ID NO 5
<211> LENGTH: 25
<212> TYPE: DNA
<213> ORGANISM: Artificial Sequence
<220> FEATURE:
<223> OTHER INFORMATION: Forward primer

<400> SEQUENCE: 5
gctagaattc cagattctgg cgatc                                             25
```

```
<210> SEQ ID NO 6
<211> LENGTH: 28
<212> TYPE: DNA
<213> ORGANISM: Artificial Sequence
<220> FEATURE:
<223> OTHER INFORMATION: Reverse primer

<400> SEQUENCE: 6
gctagggccc ttatcagatg catattct                                          28

<210> SEQ ID NO 7
<211> LENGTH: 23
<212> TYPE: DNA
<213> ORGANISM: Artificial Sequence
<220> FEATURE:
<223> OTHER INFORMATION: Forward primer

<400> SEQUENCE: 7
gctcgtcgac atgaaattct tag                                               23

<210> SEQ ID NO 8
<211> LENGTH: 27
<212> TYPE: DNA
<213> ORGANISM: Artificial Sequence
<220> FEATURE:
<223> OTHER INFORMATION: Reverse primer

<400> SEQUENCE: 8
gctactcgag ttatcagatg catattc                                           27

<210> SEQ ID NO 9
<211> LENGTH: 1695
<212> TYPE: DNA
<213> ORGANISM: Artificial Sequence
<220> FEATURE:
<223> OTHER INFORMATION: Nucleotide sequence of modified flagellin
      adjuvunctal polypeptide with melltinin signal peptide and
      influenza hemagglutinin A transmembrane-cytoplasmic tail

<400> SEQUENCE: 9
atgaaattct tagtcaacgt tgcccttgtt tttatggtcg tgtacatttc ttacatctat       60
gcggacccga tcaacatgac cggatccatg gcacaagtca ttaatacaaa cagcctgtcg      120
ctgttgaccc agaataacct gaacaaatcc cagtccgctc tgggcaccgc tatcgagcgt      180
ctgtcttccg gtctgcgtat caacagcgcg aaagacgatg cggcaggtca ggcgattgct      240 aaccgttttta ccgcgaacat caaaggtctg actcaggctt cccgtaacgc taacgacggt      300
atctccattg cgcagaccac tgaaggcgcg ctgaacgaaa tcaacaacaa cctgcagcgt      360
gtgcgtgaac tggcggttca gtctgctaac agcaccaact cccagtctga cctcgactcc      420
atccaggctg aaatcaccca cgcgcctgaac gaaatcgacc gtgtatccgg ccagactcag      480
ttcaacggcg tgaaagtcct ggcgcaggac aacaccctga ccatccaggt tggtgccaac      540
gacggtgaaa ctatcgatat cgatctgaag cagatcaact ctcagaccct gggtctggat      600
acgctgaatg tgcaacaaaa atataaggtc agcgatacgg ctgcaactgt tacaggatat      660
gccgatacaa cgattgcttt agacaatagt actttttaaag cctcggctac tggtcttggt      720
ggtactgacc agaaaattga tggcgattta aatttgatg atacgactgg aaaatattac      780
gccaaagtta ccgttacggg gggaactggt aaagatggct attatgaagt ttccgttgat      840
aagacgaacg gtgaggagac tcttgctggc ggtgcgactt ccccgcttac aggtggacta      900
cctgcgacag caactgagga tgtgaaaaat gtacaagttg caaatgctga tttgacagag      960
```

-continued

```
gctaaagccg cattgacagc agcaggtgtt accggcacag catctgttgt taagatgtct    1020
tatactgata taacggtaa aactattgat ggtggtttag cagttaaggt aggcgatgat     1080
tactattctg caactcaaaa taaagatggt tccataagta ttaatactac gaaatacact    1140
gcagatgacg gtacatccaa aactgcacta aacaaactgg gtgacgcaga cggcaaaacc   1200
gaagttgttt ctattggtgg taaaacttac gctgcaagta aagccgaagg tcacaacttt   1260
aaagcacagc tgatctggc ggaagcggct gctacaacca ccgaaaaccc gctgcagaaa    1320
attgatgctg ctttggcaca ggttgacacg ttacgttctg acctgggtgc ggtacagaac   1380
cgtttcaact ccgctattac caacctgggc aacaccgtaa acaacctgac ttctgcccgt   1440
agccgtatcg aagattccga ctacgcgacc gaagtttcca acatgtctcg cgcgcagatt   1500
ctgcagcagg ccgtacctc cgttctggcg caggcgaacc aggttccgca aaacgtcctc    1560
tctttactgc gtgaattcca gattctggcg atctactcaa ctgtcgccag ttcactggtg   1620
cttttggtct ccctgggggc aatcagtttc tggatgtgtt ctaatggatc tttgcagtgc   1680
agaatatgca tctga                                                    1695
```

<210> SEQ ID NO 10
<211> LENGTH: 564
<212> TYPE: PRT
<213> ORGANISM: Artificial Sequence
<220> FEATURE:
<223> OTHER INFORMATION: Amino acid sequence of modified flagellin
      adjuvunctal polypeptide with melltinin signal peptide and
      influenza hemagglutinin A transmembrane-cytoplasmic tail

<400> SEQUENCE: 10

```
Met Lys Phe Leu Val Asn Val Ala Leu Val Phe Met Val Val Tyr Ile
1               5                   10                  15

Ser Tyr Ile Tyr Ala Asp Pro Ile Asn Met Thr Gly Ser Met Ala Gln
            20                  25                  30

Val Ile Asn Thr Asn Ser Leu Ser Leu Leu Thr Gln Asn Asn Leu Asn
        35                  40                  45

Lys Ser Gln Ser Ala Leu Gly Thr Ala Ile Glu Arg Leu Ser Ser Gly
    50                  55                  60

Leu Arg Ile Asn Ser Ala Lys Asp Asp Ala Ala Gly Gln Ala Ile Ala
65                  70                  75                  80

Asn Arg Phe Thr Ala Asn Ile Lys Gly Leu Thr Gln Ala Ser Arg Asn
                85                  90                  95

Ala Asn Asp Gly Ile Ser Ile Ala Gln Thr Thr Glu Gly Ala Leu Asn
            100                 105                 110

Glu Ile Asn Asn Asn Leu Gln Arg Val Arg Glu Leu Ala Val Gln Ser
        115                 120                 125

Ala Asn Ser Thr Asn Ser Gln Ser Asp Leu Asp Ser Ile Gln Ala Glu
    130                 135                 140

Ile Thr Gln Arg Leu Asn Glu Ile Asp Arg Val Ser Gly Gln Thr Gln
145                 150                 155                 160

Phe Asn Gly Val Lys Val Leu Ala Gln Asp Asn Thr Leu Thr Ile Gln
                165                 170                 175

Val Gly Ala Asn Asp Gly Glu Thr Ile Asp Ile Asp Leu Lys Gln Ile
            180                 185                 190

Asn Ser Gln Thr Leu Gly Leu Asp Thr Leu Asn Val Gln Gln Lys Tyr
        195                 200                 205

Lys Val Ser Asp Thr Ala Ala Thr Val Thr Gly Tyr Ala Asp Thr Thr
    210                 215                 220
```

```
Ile Ala Leu Asp Asn Ser Thr Phe Lys Ala Ser Ala Thr Gly Leu Gly
225                 230                 235                 240

Gly Thr Asp Gln Lys Ile Asp Gly Asp Leu Lys Phe Asp Thr Thr
                    245                 250                 255

Gly Lys Tyr Tyr Ala Lys Val Thr Val Thr Gly Gly Thr Gly Lys Asp
            260                 265                 270

Gly Tyr Tyr Glu Val Ser Val Asp Lys Thr Asn Gly Glu Glu Thr Leu
            275                 280                 285

Ala Gly Gly Ala Thr Ser Pro Leu Thr Gly Gly Leu Pro Ala Thr Ala
            290                 295                 300

Thr Glu Asp Val Lys Asn Val Gln Val Ala Asn Ala Asp Leu Thr Glu
305                 310                 315                 320

Ala Lys Ala Ala Leu Thr Ala Ala Gly Val Thr Gly Thr Ala Ser Val
                    325                 330                 335

Val Lys Met Ser Tyr Thr Asp Asn Asn Gly Lys Thr Ile Asp Gly Gly
                340                 345                 350

Leu Ala Val Lys Val Gly Asp Asp Tyr Tyr Ser Ala Thr Gln Asn Lys
                355                 360                 365

Asp Gly Ser Ile Ser Ile Asn Thr Thr Lys Tyr Thr Ala Asp Asp Gly
370                 375                 380

Thr Ser Lys Thr Ala Leu Asn Lys Leu Gly Asp Ala Asp Gly Lys Thr
385                 390                 395                 400

Glu Val Val Ser Ile Gly Gly Lys Thr Tyr Ala Ala Ser Lys Ala Glu
                405                 410                 415

Gly His Asn Phe Lys Ala Gln Pro Asp Leu Ala Glu Ala Ala Ala Thr
                420                 425                 430

Thr Thr Glu Asn Pro Leu Gln Lys Ile Asp Ala Ala Leu Ala Gln Val
                435                 440                 445

Asp Thr Leu Arg Ser Asp Leu Gly Ala Val Gln Asn Arg Phe Asn Ser
450                 455                 460

Ala Ile Thr Asn Leu Gly Asn Thr Val Asn Asn Leu Thr Ser Ala Arg
465                 470                 475                 480

Ser Arg Ile Glu Asp Ser Asp Tyr Ala Thr Glu Val Ser Asn Met Ser
                485                 490                 495

Arg Ala Gln Ile Leu Gln Gln Ala Gly Thr Ser Val Leu Ala Gln Ala
                500                 505                 510

Asn Gln Val Pro Gln Asn Val Leu Ser Leu Leu Arg Glu Phe Gln Ile
                515                 520                 525

Leu Ala Ile Tyr Ser Thr Val Ala Ser Ser Leu Val Leu Leu Val Ser
                530                 535                 540

Leu Gly Ala Ile Ser Phe Trp Met Cys Ser Asn Gly Ser Leu Gln Cys
545                 550                 555                 560

Arg Ile Cys Ile

<210> SEQ ID NO 11
<211> LENGTH: 9
<212> TYPE: PRT
<213> ORGANISM: Artificial Sequence
<220> FEATURE:
<223> OTHER INFORMATION: MHC-1 HA peptide 1

<400> SEQUENCE: 11

Ile Tyr Ser Thr Val Ala Ser Ser Leu
1               5
```

```
<210> SEQ ID NO 12
<211> LENGTH: 9
<212> TYPE: PRT
<213> ORGANISM: Artificial Sequence
<220> FEATURE:
<223> OTHER INFORMATION: MHC-1 HA peptide 2

<400> SEQUENCE: 12

Leu Tyr Glu Lys Val Lys Ser Gln Leu
1               5

<210> SEQ ID NO 13
<211> LENGTH: 11
<212> TYPE: PRT
<213> ORGANISM: Artificial Sequence
<220> FEATURE:
<223> OTHER INFORMATION: MHC-II HA peptide 1

<400> SEQUENCE: 13

Ser Phe Glu Arg Phe Glu Ile Phe Pro Lys Glu
1               5                   10

<210> SEQ ID NO 14
<211> LENGTH: 12
<212> TYPE: PRT
<213> ORGANISM: Artificial Sequence
<220> FEATURE:
<223> OTHER INFORMATION: MHC-II HA peptide 2

<400> SEQUENCE: 14

His Asn Thr Asn Gly Val Thr Ala Ala Cys Ser His
1               5                   10

<210> SEQ ID NO 15
<211> LENGTH: 12
<212> TYPE: PRT
<213> ORGANISM: Artificial Sequence
<220> FEATURE:
<223> OTHER INFORMATION: MHC-II HA peptide 3

<400> SEQUENCE: 15

Cys Pro Lys Tyr Val Arg Ser Ala Lys Leu Arg Met
1               5                   10

<210> SEQ ID NO 16
<211> LENGTH: 12
<212> TYPE: PRT
<213> ORGANISM: Artificial Sequence
<220> FEATURE:
<223> OTHER INFORMATION: MHC-II HA peptide 4

<400> SEQUENCE: 16

Lys Leu Lys Asn Ser Tyr Val Asn Lys Lys Gly Lys
1               5                   10

<210> SEQ ID NO 17
<211> LENGTH: 15
<212> TYPE: PRT
<213> ORGANISM: Artificial Sequence
<220> FEATURE:
<223> OTHER INFORMATION: MHC-II HA peptide 5

<400> SEQUENCE: 17

Asn Ala Tyr Val Ser Val Val Thr Ser Lys Tyr Asn Arg Arg Phe
1               5                   10                  15
```

```
<210> SEQ ID NO 18
<211> LENGTH: 16
<212> TYPE: PRT
<213> ORGANISM: Artificial Sequence
<220> FEATURE:
<223> OTHER INFORMATION: Flexible linker

<400> SEQUENCE: 18

Gly Ala Pro Val Tyr Pro Tyr Asp Val Pro Asp Tyr Ala Ser Pro Trp
1               5                   10                  15

<210> SEQ ID NO 19
<211> LENGTH: 135
<212> TYPE: PRT
<213> ORGANISM: Artificial Sequence
<220> FEATURE:
<223> OTHER INFORMATION: Insert antigenic

<400> SEQUENCE: 19

Val Asp His Met Ala Ala Ala Ser Leu Leu Thr Glu Val Glu Thr
1               5                   10                  15

Pro Ile Arg Asn Glu Trp Gly Ser Arg Ser Asn Asp Ser Ser Asp Pro
            20                  25                  30

Ala Ala Gly Thr Ser Ala Ala Ala Ser Leu Leu Thr Glu Val Glu Thr
            35                  40                  45

Pro Ile Arg Asn Glu Trp Gly Ser Arg Ser Asn Asp Ser Ser Asp Pro
        50                  55                  60

Ala Ala Ala Leu Gln Ala Ala Ala Ser Leu Leu Thr Glu Val Glu Thr
65                  70                  75                  80

Pro Ile Arg Asn Glu Trp Gly Ser Arg Ser Asn Asp Ser Ser Asp Pro
            85                  90                  95

Ala Ala Ala Ala Cys Ala Ala Ala Ser Leu Leu Thr Glu Val Glu Thr
            100                 105                 110

Pro Ile Arg Asn Glu Trp Gly Ser Arg Ser Asn Asp Ser Ser Asp Pro
            115                 120                 125

Ala Ala Ala Ala Ala Lys Leu
            130             135
```

IMMUNOGENIC COMPOSITIONS AND METHODS OF USE THEREOF

CROSS-REFERENCE TO RELATED APPLICATION

This application is a Divisional filing of U.S. patent application Ser. No. 12/808,741 filed Sep. 13, 2010, which is a 371(c) application of PCT/US08/87194 filed Dec. 17, 2008 and claims the benefit of priority to U.S. Provisional Patent Application Nos. 61/014,130 filed Dec. 17, 2007, and 61/078,815 filed Jul. 8, 2008, which applications are hereby incorporated by this reference in their entireties.

STATEMENT REGARDING FEDERALLY SPONSORED RESEARCH OR DEVELOPMENT

This invention was made with government support under Grant No. AI068003 awarded by the National Institutes of Health. The government has certain rights in the invention.

BACKGROUND

The innate immune responses of a host are the first line of defense against infectious disease. The principal challenge for the host is to detect the pathogen and mount a rapid defensive response. A group of proteins that comprise the Toll-like Receptor (TLR) family performs this role in vertebrate organisms. The TLRs are key proteins that allow mammals, whether immunologically naïve or experienced, to detect microbes. For instance, TLR5 recognizes bacterial flagellin, the major structural protein of flagella. Flagellin is a 55-kD protein monomer obtained from bacterial flagella, polymeric rod-like appendages that extend from the outer membrane of Gram-negative bacteria. Gram negative flagellin is a potent inducer of innate immune effectors, such as cytokines and nitric oxide. Vaccines that induce mucosal immunity are likely to provide the most effective protection against pathogens, such as influenza and other viruses.

Since the outbreak of a highly pathogenic avian influenza virus (HPAI) H5N1 variant in 1997 in Hong Kong, there have been increased concerns about the threat of a new pandemic that may cause widespread fatal infection in humans. Although the transmission of avian influenza viruses from birds to humans is a rare event, both the continuing increase of infected human cases and the high mortality rates suggest the persisting threat of an H5N1 pandemic. There is evidence that the 1918 pandemic virus, which caused an estimated 40 million deaths, was an avian virus directly adapted to humans. Although two classes of antiviral drugs targeting the viral matrix protein M2 and neuraminidase, respectively, are available against influenza A viruses, financial and supply limitations as well as frequent drug resistance may limit the ability to utilize these drugs for preventing a new pandemic. It is well recognized that an effective vaccine is the primary strategy for protection against an emerging pandemic.

Currently, an inactivated influenza vaccine is the dominant form used, although a live attenuated (cold-adapted) influenza virus vaccine has also been introduced. However, the emergence of a new pandemic strain could easily overwhelm the present capacity of vaccine production, which is based on embryonic hens' eggs. There are additional concerns that biosafety containment facilities may be needed for virus-based vaccine production, and a period of 6 to 9 months would be required. A safe, convenient, and more reliable alternative is needed as a countermeasure to the emerging challenge.

As a new form of vaccine candidate, virus-like particles (VLPs) have been reported to be potent vaccines for a variety of pathogenic viruses (Koutsky et al., (2002) N. Engl. J. Med. 347:1645-1651; Leclerc et al., (2007) J. Virol. 81:1319-1326; Revaz et al., (2007) Antivir. Res. 76:75-85; Skountzou et al., (2007) J. Virol. 81:1083-1094; Zhang et al., (2007) Scand. J. Immunol. 65:320-3). VLPs elicit immune responses including both B-cell-mediated antibody and specific T-cell-mediated cellular responses to protect experimental animals against lethal influenza virus challenge (Bright et al., (2007) Vaccine 25:3871-3878; Galarza et al., (2005) Viral Immunol. 18:244-251; Matassov et al., (2007) Viral Immunol. 20:441-452; Pushko et al., (2005) Vaccine 23:5751-5759; Quan et al., (2007) J. Virol. 81:3514-3524). However, though VLPs provide an attractive platform for designing vaccines against a possible new influenza virus pandemic strain, they resemble the current vaccines in inducing immune responses that are predominantly subtype specific. An important advance would be the development of new vaccines with enhanced breadth of immunity, which could potentially be used to prevent infection by newly emerging variants, including influenza viruses of other subtypes.

SUMMARY

Briefly described, embodiments of this disclosure, among others, encompass compositions and methods for generating immune responses in an animal or human host. Embodiments of the compositions of the disclosure encompass proteins derived from the surface proteins of bacteria and protozoa, and in particular the flagellum component flagellin, and which have adjunctival properties when administered in conjunction with an immunogen. Embodiments of the compositions of the disclosure, therefore, are modified surface proteins that incorporate a heterologous transmembrane-cytoplasmic domain allowing the peptides to be incorporated into virus-like particles.

An embodiment of the disclosure, therefore, provide adjuvant polypeptides comprising a first region comprising a heterologous signal peptide; a second region comprising at least one domain capable of selectively interacting with a Toll-like receptor of an animal or human cell, and wherein the domain is capable of increasing an immune response in a recipient host; and at least one heterologous region selected from the group consisting of a signal peptide region and a transmembrane-cytoplasmic tail region.

An embodiment of the disclosure may comprise a first region, wherein the first region comprises a signal peptide; a second region, where the second region may comprise at least one domain capable of selectively interacting with a Toll-like receptor of an animal or human cell, and where the domain may be capable of increasing an immune response in a recipient host; and a third region, where the third region comprises a transmembrane-cytoplasmic tail peptide. In embodiments of this aspect of the disclosure, the at least one domain that is capable of selectively interacting with a Toll-like receptor of an animal or human cell may be derived from a surface protein of a bacterial species, or of a protozoal species.

In some embodiments of the adjuvant polypeptide, the surface protein may be a protein of a bacterial or a protozoal flagellum, or a fragment thereof. In an embodiment, the surface protein is a flagellin of the bacterial species *Salmonella enteriditis*.

Another aspect of the disclosure provides nucleic acid molecules comprising a region encoding a bacterial flagellin polypeptide, or a fragment thereof, where the flagellin polypeptide or fragment thereof comprises at least one domain capable of specifically interacting with a Toll-like receptor of an animal or human cell; and at least one region selected from the group consisting of: a region encoding a heterologous signal peptide, and a region encoding a transmembrane-cytoplasmic tail capable of being incorporated into a virus-like particle or virosome.

In embodiments of this aspect of the disclosure, the heterologous signal peptide may be a bee melittin signal peptide, and the trans-membrane-cytoplasmic tail may be from an influenza virus hemagglutinin.

In some embodiments of the disclosure, the nucleic acid molecule may be operably inserted into a nucleic acid expression vector.

Another aspect of the disclosure provides immunogenic compositions comprising: an adjuvant polypeptide comprising at least one region capable of selectively interacting with a Toll-like receptor protein of a host; and an immunogen capable of inducing an immune response in a recipient host.

In an embodiment of this aspect of the disclosure, the immunogenic compositions may further comprise a virus-like carrier selected from a virus-like particle and a virosome, and wherein the adjuvant polypeptide and the immunogen may be incorporated in the virus-like particle or the virosome. In these embodiments of the disclosure, the adjuvant polypeptide may be incorporated into the virus-like particle or virosome.

In still other embodiments of the disclosure, the virus-like carrier may comprise: a viral core protein capable of self-assembling into a virus-like particle (VLP); at least one viral surface envelope glycoprotein expressed on the surface of the VLP; and at least one adjuvant molecule expressed on the surface of the VLP, where the adjuvant molecule may comprise a membrane-anchored form of a bacterial or protozoal surface component that is a mammalian Toll-like receptor (TLR) ligand molecule. In these embodiments, the viral core protein and at least one viral surface envelope glycoprotein may be from different viruses.

Still another aspect of the disclosure provides methods of generating an immunological response in an animal or human comprising: exposing the immune system of an animal or human host to an immunogen and a virus-like carrier, wherein the virus-like carrier is a virus-like particle or a virosome, and wherein the virus-like carrier comprises an adjuvant polypeptide comprising a host cell Toll-like receptor ligand polypeptide derived from a bacterial or protozoal flagellum polypeptide, and at least one heterologous peptide selected from the group consisting of a trans-membrane-cytoplasmic tail polypeptide and a heterologous signal peptide; thereby generating in the recipient host an immune response directed against the immunogen.

In embodiments of this aspect of the disclosure, delivering to the recipient host or host cell at least one expression vector, wherein the at least one expression vector or a multiplicity of expression vectors comprise at least one polynucleotide encoding at least one polypeptide selected from the group consisting of: a viral core protein, a viral surface envelope glycoprotein, and an adjuvant molecule, wherein each of the polynucleotide or polynucleotides is operably linked to an expression control region; expressing in the recipient host or host cell at least one viral surface envelope glycoprotein, and at least one adjuvant molecule, thereby assembling a virosome virus-like carrier.

In other embodiments, an expression vector may comprise a polynucleotide encoding a viral core protein, wherein the viral core protein is incorporated into a virus-like particle.

Yet another aspect of the disclosure are methods of immunizing a host comprising: co-expressing a viral core protein, at least one viral surface envelope surface glycoprotein, and at least one adjuvant molecule in one or more host cells; whereby the viral core protein, at least one viral surface envelope glycoprotein, assemble to form a virus-like particle, and wherein the at least one adjuvant molecule is mammalian toll-like receptor ligand molecule.

DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 1A shows a digital image of a Coomassie Blue stained electrophoretic gel analysis of *Salmonella* flagellin expressed and isolated from *E. coli*. Lane 1: molecular weight markers; Lane 2: soluble flagellin expressed by an *E. coli* culture and purified therefrom with affinity chorography.

FIG. 1B is a digital mage of a Western blot analysis showing soluble flagellin.

FIG. 2 shows a Coomassie Blue stained electrophoretic gel analysis (10% SDS polyacrylamide gel) of flagellin proteins. The samples shown were from individually prepared batches of flagellin proteins. The band on the extreme left is monomeric flagellin having a size of 50-60 kDa.

FIG. 5 schematically illustrates an embodiment of a chimeric flagellin nucleic acid molecule, and the domains therein.

FIG. 6 illustrates the nucleotide sequences SEQ ID NOS.: 1-8 of primers used in the construction of a nucleic acid molecule encoding a membrane-anchored flagellin-having, at the N terminus of the flagellin-encoding nucleic acid region, the coding sequence for the signal peptide (SP) of the honeybee protein melittin and, at the C-terminus of the flagellin-encoding nucleic acid, the transmembrane-cytoplasmic tail (TM-CT) from influenza hemagglutinin (HA).

FIG. 7 illustrates the nucleotide sequence SEQ ID NO.: 9 of the nucleic acid molecule encoding a membrane-anchored flagellin-having, at the N terminus of the flagellin-encoding nucleic acid region, the coding sequence for the signal peptide (SP) of the honeybee protein melittin (capitalized and underlined) and, at the C-terminus of the flagellin-encoding nucleic acid, the transmembrane-cytoplasmic tail (TM-CT) from influenza hemagglutinin (HA).

FIG. 8 illustrates the amino acid sequence SEQ ID NO.: 10 derived from the nucleotide sequence SEQ ID NO.: 9. Potential N-linked glycosylation sites are indicated by arrows.

FIG. 17 illustrates peptide sequences SEQ ID NOs.: 11-18.

DETAILED DESCRIPTION

Figure 3:
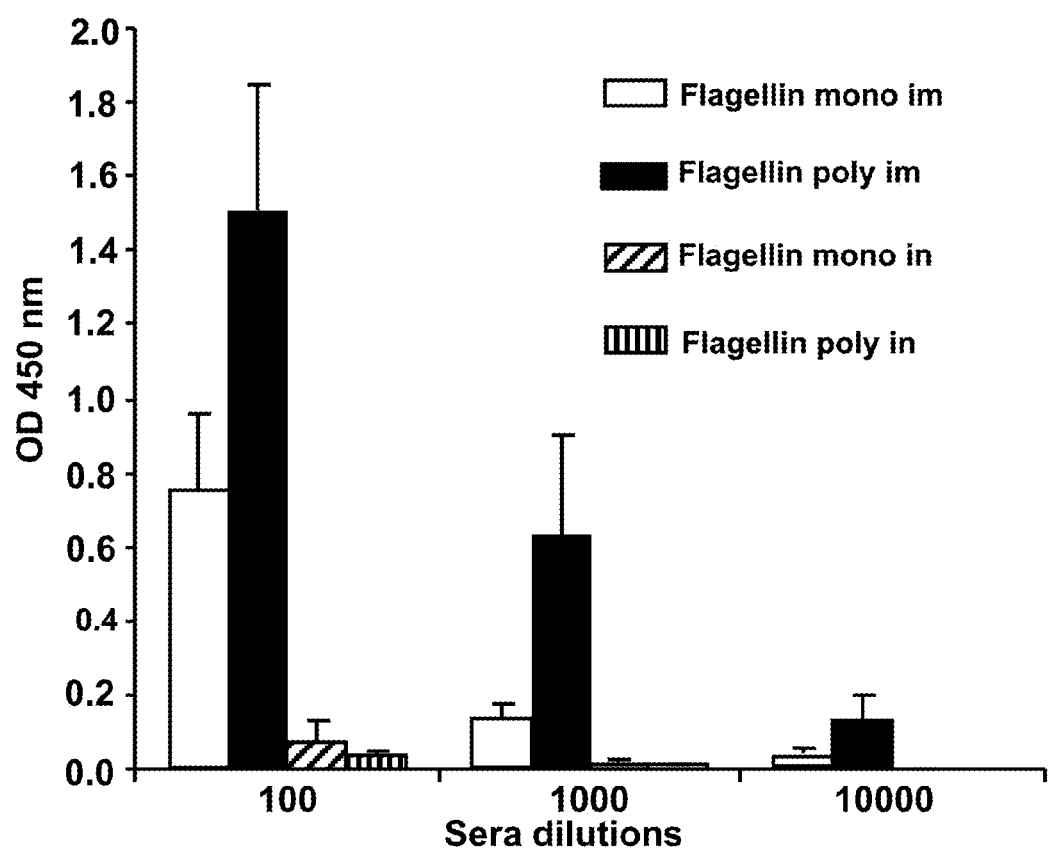
FIG. 3 is a bar graph illustrating the immune responses generated by recombinant monomeric soluble flagellin from *Salmonella enteritidis* gene expressed in an *E. coli* cell system, and purified polymeric flagellin isolated from *Salmonella enteritidis* bacteria. The flagellins were tested for immunogenicity in female Balb/c 4-6 old mice. Plates were coated with anti-*S. enteriditis* flagellin-specific monoclonal antibody.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a cell" includes a plurality or multiplicity of cells. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing," "having," and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. patent law and the term is open-ended, allowing for the presence of more than that which is recited so long as basic or novel characteristics of that which is recited is not changed by the presence of more than that which is recited, but excludes prior art embodiments.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified.

Prior to describing the various embodiments, the following definitions are provided and should be used unless otherwise indicated.

DEFINITIONS

In describing and claiming the disclosed subject matter, the following terminology will be used in accordance with the definitions set forth below.

Unless otherwise defined, all technical and scientific terms used herein have the same meaning as commonly understood by one of ordinary skill in the art of molecular biology. Although methods and materials similar or equivalent to those described herein can be used in the practice or testing of the present disclosure, suitable methods and materials are described herein.

Further definitions are provided in context below. Unless otherwise defined, all technical and scientific terms used herein have the same meaning as commonly understood by one of ordinary skill in the art of molecular biology. Although methods and materials similar or equivalent to those described herein can be used in the practice or testing of the present disclosure, suitable methods and materials are described herein.

Unless otherwise defined, all terms of art, notations and other scientific terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 3rd. edition (2001) Cold Spring Harbor Laboratory Press, Cold Spring Harbor, N.Y. and Current Protocols in Molecular Biology (Ausbel et al., eds., John Wiley & Sons, Inc. 2001). As appropriate, procedures involving the use of commercially available kits and reagents are generally carried out in accordance with manufacturer defined protocols and/or parameters unless otherwise noted.

As used herein, the term "adjuvant molecule" includes bacterial surface proteins capable of eliciting an immune response in a host. In particular the term includes bacterial surface proteins capable of targeting a host Toll-like receptor (TLR) protein, such as, but not limited to, a bacterial flagellin protein that targets a host TLR5 protein. In particular embodiments, the adjuvant molecule is a "membrane-anchored form" of the adjuvant molecule which indicates that the adjuvant molecule has been engineered to include a signal peptide (SP) and a membrane anchor sequence to direct the transport and membrane orientation of the protein. Thus, in embodiments, a membrane-anchored form of an adjuvant molecule is a recombinant protein including a portion of the bacterial protein (such as bacterial flagellin) fused to a SP and membrane anchor sequence (e.g., the membrane-anchored form of *Salmonella* flagellin described in Example 5 below).

The term "virus-like carrier" as used herein refers to either a virus-like particle", a virosome, or both.

The term "virus-like particle" (VLPs) as used herein refers to a membrane-surrounded viral core structure having viral envelope proteins expressed on the VLP surface. In addition, adjuvant molecules can be expressed on the VLP. Further, viral core proteins are located within the membrane of the VLP. Additional components of VLPs, as known in the art, can be included within or disposed on the VLP. VLPs do not contain intact viral nucleic acids, and they are non-infectious. Desirably, there is sufficient viral surface envelope glycoprotein and/or adjuvant molecules expressed, at least in part, on the surface of the VLP so that when a VLP preparation is formulated into an immunogenic composition and administered to an animal or human, an immune response (cell-mediated or humoral) is raised.

The term "virosome" as used herein refers to a virus-like carrier that is similar to a virus-like particle, except that a virosome does not contain a viral core protein.

A "chimeric virus-like particle" as used herein, can be defined as a VLP having at least one viral surface envelope glycoprotein incorporated into the VLP, wherein the viral core protein and at least one viral surface envelope glycoprotein are from different viruses. A chimeric VLP, as used herein, may include additional viral surface envelope glycoproteins that are from the same or different virus as the viral core protein, so long as at least one is different.

A "phenotypically mixed" VLP, as used herein, can be defined as a VLP having at least two different surface molecules (e.g., surface envelope glycoproteins and/or adjuvant molecules) incorporated into the VLP. A phenotypically mixed VLP, as used herein, may include additional surface molecules that are from the same or different source as the viral core protein, so long as at least one is different.

A "truncated" viral surface envelope glycoprotein is one having less than a full length protein (e.g., a portion of the cytoplasmic domain has been removed), which retains surface antigenic determinants against which an immune response is generated, preferably a protective immune response, and it retains sufficient envelope sequence for proper membrane insertion. The skilled artisan can produce truncated virus envelope proteins using recombinant DNA technology and virus coding sequences, which are readily available to the public.

As used herein "chimeric" viral surface glycoproteins are ones that contain at least a portion of the extracellular domain of a viral surface glycoprotein of one virus and at least a portion of the transmembrane and/or cytoplasmic domains and/or signal peptide sequence of a different transmembrane glycoprotein from a different virus or other organism. Such chimeric proteins retain surface antigenic determinants against which an immune response is generated, preferably a protective immune response, and retain sufficient envelope sequence for proper precursor processing and membrane insertion. The operably linked transmembrane and/or cytoplasmic domains will serve to preferentially interact with the desired viral core protein components in VLP assembly, and thus increase the levels of viral surface glycoprotein in VLPs. The skilled artisan can produce chimeric viral surface glycoproteins using recombinant DNA technology and protein coding sequences, techniques known to those of skill in the art and available to the public. Such chimeric viral surface glycoproteins may be useful for increasing the level of incorporation of viral glycoproteins in VLPs for viruses that may naturally have low levels of incorporation.

The term "polypeptides" includes proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

"Variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall (homologous) and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of this disclosure and still result in a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly where the biologically functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamnine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take one or more of the foregoing characteristics into consideration are well known to those of skill in the art and include, but are not limited to (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest. The term "substantially homologous" is used herein to denote polypeptides of the present disclosure having about 50%, about 60%, about 70%, about 80%, about 90%, and preferably about 95% sequence identity to the reference sequence. Percent sequence identity is determined by conventional methods as discussed above. In general, homologous polypeptides of the present disclosure are characterized as having one or more amino acid substitutions, deletions, and/or additions.

"Identity," as known in the art, is a relationship between two or more polypeptide sequences, as determined by comparing the sequences. In the art, "identity" also refers to the degree of sequence relatedness between polypeptides as determined by the match between strings of such sequences. "Identity" and "similarity" can be readily calculated by known methods, including, but not limited to, those described in Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48: 1073, (1988).

Preferred methods to determine identity are designed to give the largest match between the sequences tested. Methods to determine identity and similarity are codified in publicly available computer programs. The percent identity between two sequences can be determined by using analysis software (i.e., Sequence Analysis Software Package of the Genetics Computer Group, Madison, Wis.) that incorporates the Needelman & Wunsch, (J. Mol. Biol., 48: 443-453, 1970) algorithm (e.g., NBLAST and XBLAST). The default parameters are used to determine the identity for the polypeptides of the present disclosure.

By way of example, a polypeptide sequence may be identical to the reference sequence, that is be 100% identical, or it may include up to a certain integer number of amino acid alterations as compared to the reference sequence such that the % identity is less than 100%. Such alterations are selected from: at least one amino acid deletion, substitution (including conservative and non-conservative substitution), or insertion, and wherein said alterations may occur at the amino- or carboxy-terminus positions of the reference polypeptide sequence or anywhere between those terminal positions, interspersed either individually among the amino acids in the reference sequence, or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

Conservative amino acid variants can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methyl-glycine, allo-threonine, methylthreonine, hydroxy-ethylcysteine, hydroxyethylhomocysteine, nitro-glutamine, homoglutamine, pipecolic acid, thiazolidine carboxylic acid, dehydroproline, 3- and 4-methylproline, 3,3-dimethylproline, tert-leucine, norvaline, 2-azaphenyl-alanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. (Robertson, et al., J. Am. Chem. Soc., 113: 2722, 1991; Ellman, et al., Methods Enzymol., 202: 301, 1991; Chung, et al., Science, 259: 806-9, 1993; and Chung, et al., Proc. Natl. Acad. Sci. USA, 90: 10145-9, 1993). In a second method, translation is carried out in *Xenopus* oocytes by microinjection of mutated mRNA and chemically aminoacylated suppressor tRNAs (Turcatti, et al., J. Biol. Chem., 271: 19991-8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. (Koide, et al., Biochem., 33: 7470-6, 1994). Naturally occurring amino acid residues can be converted to non-naturally occurring species by in vitro chemical modification. Chemical modification can be combined with site-directed mutagenesis to further expand the range of substitutions (Wynn, et al., Protein Sci., 2: 395-403, 1993).

Furthermore, unless the context demands otherwise, the term peptide, polypeptide and protein are used interchangeably to refer to amino acids in which the amino acid residues are linked by covalent peptide bonds or alternatively (where post-translational processing has removed an internal segment) by covalent disulphide bonds, etc. The amino acid chains can be of any length and comprise at least two amino acids, they can include domains of proteins or full-length proteins. Unless otherwise stated the terms peptide, polypeptide, and protein also encompass various modified forms thereof, including but not limited to glycosylated forms, phosphorylated forms, etc.

As used herein, the term "polynucleotide" generally refers to any polyribonucleotide or polydeoxribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically, double-stranded or a mixture of single- and double-stranded regions. The terms "nucleic acid," "nucleic acid sequence," or "oligonucleotide" also encompass a polynucleotide as defined above.

In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

It will be appreciated that a great variety of modifications have been made to DNA and RNA that serve many useful purposes known to those of skill in the art. The term polynucleotide as it is employed herein embraces such chemically, enzymatically, or metabolically modified forms of polynucleotides, as well as the chemical forms of DNA and RNA characteristic of viruses and cells, including simple and complex cells, inter alia.

By way of example, a polynucleotide sequence of the present disclosure may be identical to the reference sequence, that is be 100% identical, or it may include up to a certain integer number of nucleotide alterations as compared to the reference sequence. Such alterations are selected from the group including at least one nucleotide deletion, substitution, including transition and transversion, or insertion, and wherein said alterations may occur at the 5' or 3' terminus positions of the reference nucleotide sequence or anywhere between those terminus positions, interspersed either individually among the nucleotides in the reference sequence or in one or more contiguous groups within the reference sequence. The number of nucleotide alterations is determined by multiplying the total number of nucleotides in the reference nucleotide by the numerical percent of the respective percent identity (divided by 100) and subtracting that product from said total number of nucleotides in the reference nucleotide. Alterations of a polynucleotide sequence encoding the polypeptide may alter the polypeptide encoded by the polynucleotide following such alterations.

As used herein, DNA may be obtained by any method. For example, the DNA includes complementary DNA (cDNA) prepared from mRNA, DNA prepared from genomic DNA, DNA prepared by chemical synthesis, DNA obtained by PCR amplification with RNA or DNA as a template, and DNA constructed by appropriately combining these methods.

As used herein, an "isolated nucleic acid" is a nucleic acid, the structure of which is not identical to that of any naturally occurring nucleic acid or to that of any fragment of a naturally occurring genomic nucleic acid spanning more than three genes. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in random, uncharacterized mixtures of different DNA molecules, transfected cells, or cell clones, e.g., as these occur in a DNA library such as a cDNA or genomic DNA library.

The term "substantially pure" as used herein in reference to a given polypeptide means that the polypeptide is substantially free from other biological macromolecules. For example, the substantially pure polypeptide is at least 75%, 80, 85, 95, or 99% pure by dry weight. Purity can be measured by any appropriate standard method known in the art, for example, by column chromatography, polyacrylamide gel electrophoresis, or HPLC analysis.

The DNA encoding the protein disclosed herein can be prepared by the usual methods: cloning cDNA from mRNA encoding the protein, isolating genomic DNA and splicing it, chemical synthesis, and so on.

cDNA can be cloned from mRNA encoding the protein by, for example, the method described below:

First, the mRNA encoding the protein is prepared from the above-mentioned tissues or cells expressing and producing the protein. mRNA can be prepared by isolating total RNA by a known method such as guanidine-thiocyanate method (Chirgwin et al., Biochemistry, 18:5294, 1979), hot phenol method, or AGPC method, and subjecting it to affinity chromatography using oligo-dT cellulose or poly-U Sepharose.

Then, with the mRNA obtained as a template, cDNA is synthesized, for example, by a well-known method using reverse transcriptase, such as the method of Okayama et al (Mol. Cell. Biol. 2:161 (1982); Mol. Cell. Biol. 3:280 (1983)) or the method of Hoffman et al. (Gene 25:263 (1983)), and converted into double-stranded cDNA. A cDNA library is prepared by transforming *E. coli* with plasmid vectors, phage vectors, or cosmid vectors having this cDNA or by transfecting *E. coli* after in vitro packaging.

The plasmid vectors used herein are not limited as long as they are replicated and maintained in hosts. Any phage vector that can be replicated in hosts can also be used. Examples of usually used cloning vectors are pUC19, λgt10, lgt11, and so on. When the vector is applied to immunological screening as mentioned below, a vector having a promoter that can express a gene encoding the desired protein in a host is preferably used.

cDNA can be inserted into a plasmid by, for example, the method of Maniatis et al. (Molecular Cloning, A Laboratory Manual, second edition, Cold Spring Harbor Laboratory, p.1.53, 1989). cDNA can be inserted into a phage vector by, for example, the method of Hyunh et al. (DNA cloning, a practical approach, 1, p.49 (1985)). These methods can be simply performed by using a commercially available cloning kit (for example, a product from Takara Shuzo). The recombinant plasmid or phage vector thus obtained is introduced into an appropriate host cell such as a prokaryote (for example, *E. coli*: HB101, DH5a, MC1061/P3, etc).

Examples of a method for introducing a plasmid into a host are, calcium chloride method, calcium chloride/rubidium chloride method and electroporation method, described in Molecular Cloning, A Laboratory Manual (second edition, Cold Spring Harbor Laboratory, p.1.74 (1989)). Phage vectors can be introduced into host cells by, for example, a method in which the phage DNAs are introduced into grown hosts after in vitro packaging. In vitro packaging can be easily performed with a commercially available in vitro packaging kit (for example, a product from Stratagene or Amersham).

An "expression vector" is useful for expressing the DNA encoding the protein used herein and for producing the protein. The expression vector is not limited as long as it expresses the gene encoding the protein in various prokaryotic and/or eukaryotic host cells and produces this protein. Examples thereof are pMAL C2, pEF-BOS (Nucleic Acids Res. 18:5322 (1990) and so on), pME18S (Experimental Medicine: SUPPLEMENT, "Handbook of Genetic Engineering" (1992)), etc.

When bacteria, particularly *E. coli* are used as host cells, an expression vector generally comprises, at least, a promoter/operator region, an initiation codon, the DNA encoding the protein termination codon, terminator region, and replicon.

When yeast, animal cells, or insect cells are used as hosts, an expression vector is preferably comprising, at least, a promoter, an initiation codon, the DNA encoding the protein and a termination codon. It may also comprise the DNA encoding a signal peptide, enhancer sequence, 5'- and 3'-untranslated region of the gene encoding the protein, splicing junctions, polyadenylation site, selectable marker region, and replicon. The expression vector may also contain, if required, a gene for gene amplification (marker) that is usually used.

A promoter/operator region to express the protein in bacteria comprises a promoter, an operator, and a Shine-Dalgarno (SD) sequence (for example, AAGG). For example, when the host is *Escherichia*, it preferably comprises Trp promoter, lac promoter, recA promoter, lambda.PL promoter, b 1pp promoter, tac promoter, or the like. Examples of a promoter to express the protein in yeast are PH05 promoter, PGK promoter, GAP promoter, ADH promoter, and so on. When the host is *Bacillus*, examples thereof are SL01 promoter, SP02 promoter, penP promoter, and so on. When the host is a eukaryotic cell such as a mammalian cell, examples thereof are SV40-derived promoter, retrovirus promoter, heat shock promoter, and so on, and preferably SV-40 and retrovirus-derived one. As a matter of course, the promoter is not limited to the above examples. In addition, using an enhancer is effective for expression.

A preferable initiation codon is, for example, a methionine codon (ATG).

A commonly used termination codon (for example, TAG, TAA, TGA) is exemplified as a termination codon. Usually, used natural or synthetic terminators are used as a terminator region.

A "replicon" means a DNA capable of replicating the whole DNA sequence in host cells, and includes a natural plasmid, an artificially modified plasmid (DNA fragment prepared from a natural plasmid), a synthetic plasmid, and so on. Examples of preferable plasmids are pBR322 or its artificial derivatives (DNA fragment obtained by treating pBR322 with appropriate restriction enzymes) for *E. coli*, yeast 2.mu. plasmid or yeast chromosomal DNA for yeast, and pRSVneo ATCC 37198, pSV2dhfr ATCC 37145, pdBPV-MMTneo ATCC 37224, pSV2neo ATCC 37149, and such for mammalian cells.

An enhancer sequence, polyadenylation site, and splicing junction that are usually used in the art, such as those derived from SV40 can also be used.

A selectable marker usually employed can be used according to the usual method. Examples thereof are resistance genes for antibiotics, such as tetracycline, ampicillin, or kanamycin.

The expression vector used herein can be prepared by continuously and circularly linking at least the above-mentioned promoter, initiation codon, DNA encoding the protein, termination codon, and terminator region, to an appropriate replicon. If desired, appropriate DNA fragments (for example, linkers, restriction sites, and so on), can be used by the usual method such as digestion with a restriction enzyme or ligation using T4 DNA ligase.

As used herein, "transformants" can be prepared by introducing the expression vector mentioned above into host cells.

As used herein, "host" cells are not limited as long as they are compatible with an expression vector mentioned above and can be transformed. Examples thereof are various cells such as wild-type cells or artificially established recombinant cells usually used in technical field (for example, bacteria (*Escherichia* and *Bacillus*), yeast (*Saccharomyces*, *Pichia*, and such), animal cells, insect cells, or plant cells).

By "administration" is meant introducing a composition (e.g., a vaccine, adjuvant, or immunogenic composition) of the present disclosure into a subject. The preferred route of administration of the vaccine composition is intravenous. However, any route of administration, such as oral, topical, subcutaneous, peritoneal, intra-arterial, inhalation, vaginal, rectal, nasal, introduction into the cerebrospinal fluid, or instillation into body compartments can be used.

"Immunogenic compositions" are those which result in specific antibody production or in cellular immunity when injected into a host. Such immunogenic compositions or vaccines are useful, for example, in immunizing hosts against infection and/or damage caused by viruses, including, but not limited to, HIV, human T-cell leukemia virus (HTLV) type I, SIV, FIV, SARS, RVFV, Filovirus, Flavivirus, arenavirus, bunyavirus, paramyxovirus, influenza virus, cytomegalovirus, herpesvirus, and alphavirus.

By "immunogenic amount" is meant an amount capable of eliciting the production of antibodies directed against the virus, in the host to which the vaccine has been administered. It is preferred for HIV, influenza virus, RSV, and cytomegalovirus, among others, that the route of administration and the immunogenic composition is designed to optimize the immune response on mucosal surfaces, for example, using nasal administration (via an aerosol) of the immunogenic composition.

The term "pharmaceutically" or "pharmaceutically acceptable" as used herein refer to molecular entities and compositions that do not produce an adverse, allergic or other untoward reaction when administered to an animal, or a human, as appropriate.

The term "pharmaceutically acceptable carrier" as used herein refers to any carrier, excipient, diluents, adjuvants, or vehicles, such as preserving or antioxidant agents, fillers, disintegrating agents, wetting agents, emulsifying agents, suspending agents, solvents, dispersion media, coatings, antibacterial and antifungal agents, isotonic and absorption delaying agents and the like. The use of such media and agents for pharmaceutical active substances is well-known in the art. Except insofar as any conventional media or agent is incompatible with the active ingredient, its use in the therapeutic compositions is contemplated. Supplementary active ingredients can also be incorporated into the compositions as suitable therapeutic combinations.

The term "host" or "organism" as used herein includes humans, mammals (e.g., cats, dogs, horses, etc.), living cells, and other living organisms. A living organism can be as simple as, for example, a single eukaryotic cell or as complex as a mammal. Typical hosts to which embodiments of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For some applications, hosts may also include plants. For diagnostic or research applications, a wide variety of mammals will be suitable subjects, including rodents (e.g., mice, rats, hamsters), rabbits, primates, and swine such as inbred pigs and the like. Additionally, for in vitro applications, such as in vitro diagnostic and research applications, body fluids and cell samples of the above subjects will be suitable for use, such as mammalian (particularly primate such as human) blood, urine, or tissue samples, or blood, urine, or tissue samples of the animals mentioned for veterinary applications. Hosts that are "predisposed to" condition(s) can be defined as hosts that do not exhibit overt symptoms of one or more of these conditions but that are genetically, physiologically, or otherwise at risk of developing one or more of these conditions.

The term "treat", "treating", and "treatment" are an approach for obtaining beneficial or desired clinical results. For purposes of embodiments of this disclosure, beneficial or desired clinical results include, but are not limited to, alleviation of symptoms, diminishment of extent of disease, stabilization (e.g., not worsening) of disease, preventing spread of disease, delaying or slowing of disease progression, amelioration or palliation of the disease state, and remission (partial or total) whether detectable or undetectable. In addition, "treat", "treating", and "treatment" can also mean prolonging survival as compared to expected survival if not receiving treatment.

The term "condition" and "conditions" denote a state of health that can be related to infection by a virus. The infections that are discussed herein are to be included as conditions that can be treated by embodiments of the present disclosure.

Discussion:

Embodiments of the present disclosure relates to novel immunogenic compositions for stimulating systemic, and/or mucosal immunity. Embodiments of the present disclosure provides novel biological tools, chimeric virus-like particles (VLPs) and methods of use, for inducing immunogenic responses in an animal or human host. Briefly described, embodiments of the present disclosure include immunogenic compositions comprising an adjuvant molecule and an immunogen, where the adjuvant molecule may be a surface protein, such as, but not limited to, a bacterial or protozoal flagellin molecule. In certain embodiments of the present disclosure, a bacterial surface protein may be a membrane-anchored form of the protein, such as, but not limited to, a membrane-anchored flagellin. In some embodiments of the present disclosure, the surface protein may be a modified form of the protein, where such modifications may include removal or modification of certain immunogenic or antigenic amino acid sequences, and/or addition of antigenic or immunogenic sequences derived from a heterologous protein species, shown, for example in FIGS. 25 and 26 and in Example 16, below. In these embodiments, the surface polypeptide may be modified by the insertion or deletion of amino acids of the native surface polypeptide or regions of the surface polypeptide may be replaced by heterologous amino acids or amino acid sequences.

Embodiments of the present disclosure also include methods of using the immunogenic compositions of the present disclosure to generate an immune response in an animal or human host, as well as methods of making the immunogenic compositions of the present disclosure. One embodiment, for example, provides a method of presenting immunogenic moieties derived from an influenza virus, thereby inducing a protective immune response in the recipient animal or human host.

Surface Protein Adjuvant Molecules.

As described by McDonald et al., (2007) J. Infect. Dis. 195:1607-1617, and by Eaves-Pyles et al., (2001) J. Immunol. 167:7009-7016), a modified flagellin protein with a removed hypervariable region did not lose the ability to activate TLR5 activation in vitro. In some embodiments, the removed fragment may be replaced with a linker peptide, while in other embodiments it may be replaced with immunogenic fragments isolated from other polypeptides, such as bacterial or viral peptides. In some embodiments of the disclosure, the flagellin polypeptide may also be modified by the addition of a membrane-anchoring peptide sequence. It is contemplated that a useful membrane-anchoring peptide may be a viral peptide (for example, an influenza hemagglutinin (HA) membrane-anchoring sequence, an MMTV Env membrane anchor sequence, and the like).

In other embodiments of the disclosure, modified flagellin polypeptides may also comprise a signal peptide sequence. In some of these embodiments the signal peptide sequence may be isolated from a heterologous polypeptide. The signal sequence may be attached at the N- or C-terminus of the modified flagellin and may be included to help direct the incorporation of the flagellin polypeptide into a VLP. Exemplary embodiments of such variants are described in greater detail in the examples 11-13, and in and figures below, particularly FIGS. 21-23.

Immunogenic Compositions Compressions Surface Protein Adjuvant Molecules.

Embodiments of the present disclosure further encompass flagellin and/or other cell surface proteins that may be used as an adjuvant for vaccines. Flagellin has been demonstrated to have a strong adjuvant activity for influenza vaccines, and for vaccines including virus like particles (VLP). The immunogenic compositions of the present disclosure may be used to enhance an immune response, including antibody production, cytotoxic T cell activity, and cytokine activity. The presently disclosed immunogenic compositions may act as a prophylactic vaccine to prevent the onset or establishment of a viral infection such as, but not limited to, a viral infection caused by the human immunodeficiency virus (HIV), the coronavirus, the influenza virus, the paramyxovirus, the herpesvirus, the Ebola virus, the Rift Valley Fever virus, the Hantavirus, the Lassa fever virus, the Flavivirus, and the like. It is further contemplated, however, that the modified flagellin adjuvants of the present disclosure may also be used in vaccines directed against bacterial target infections for the prevention or treatment of such bacterial diseases as diphtheria, cholera, bacterial tuberculosis, and other bacterial infections known to those in the art.

The embodiments of the present disclosure further relate to novel vaccine compositions of chimeric virus-like particles for administering to humans and animals. In particular, the present disclosure demonstrates that soluble membrane-anchored flagellin and/or other surface proteins can be cloned and expressed in such as an insect cell protein expression system, and mixed with antigens (VLP or others) to be used for immunization of hosts against various pathogens.

In embodiments of the disclosure, membrane-anchored flagellin or other surface protein may be incorporated into a VLP, and in particular incorporated in a manner that exposes the membrane-anchored flagellin externally to the VLP, allowing use as a vaccine to stimulate an immunogenic response in a recipient host receiving. Such VLPs, containing membrane-anchored flagellin or other surface protein as a vaccine adjuvant can be used for systemic, mucosal or other immunostimulatory routes.

As described in the below, the methods of the present disclosure include making immunogenic compositions of the present disclosure by cloning membrane-anchored flagellin of a bacterial source and expressing the cloned membrane-anchored flagellin in insect cell protein expression system. The resulting membrane-anchored flagellin can then be incorporated into a VLP or virosome together with a selected immunogen. In some embodiments, to incorporate flagellin into VLPs, a signal peptide (SP) and a membrane anchor are fused to direct the transport and membrane orientation. In an exemplary embodiment, the resulting recombinant gene was used for the generation of recombinant baculovirus (rBV).

Modified Surface Polypeptide Variants.

Embodiments of the compositions and methods of the present disclosure may include, but are not limited to, a flagellin isolated from a bacterial source, such as *Salmonella enteritidis*. The examples below demonstrate that soluble monomeric flagellin and purified polymeric flagellin isolated from *S. enteritidis* may contribute to the generation of an immune response. In addition to flagellin from *Salmonella* spp., however, it is considered to be within the scope of the disclosure for other motile bacterial or protozoal flagellar proteins to be used in the constructs and compositions of the disclosure. In particular, bacterial or protozoal surface polypeptides that may cooperate with the TLR5 or other TLRs include, but are not limited to polypeptides of: *Proteus* spp., *Pseudomonas* spp., *Serratia* spp., *Morganella morganii* (grown under 30° C.), *Providencia stuartii, P. rettgeri, P. Alcalifaciens, Arcobacter* spp., *Aeromonas* spp., *Acidivorax* spp., *Helicobacter* spp., *Flexispira rappine, Wolinella* spp., *Rhizobium* spp., *Vibrio* spp., *Legionella* spp., *Edwardsiella* spp., *Shigella* spp., *Eschericia* spp., *Listeria* spp., *Bordetella* spp., *Burkholderia* spp., *Helicobacter* spp., *Butyrivibrio* spp., *Roseburia* spp., *Thermotoga* spp., *Clostridium* spp., *Bacillus* spp., *Oceanobacillus iheyensis, Thermotoga maritime, Leptospira* spp., *Yersinia* spp., *Bordetella* spp, *Legionella* spp., *Trichomonas* spp., *Bartonella bacilliformis, Caulobater crescentus, Campylobacer* spp., and *Treponema* spp flagellins. Modified forms of the flagellins can be used, where portions of the flagellin polypeptide has been deleted and replaced by a linker sequence and/or an immunogenic or antigenic sequence.

In embodiments of the disclosure, a modified flagellin polypeptide may be a *Salmonella* flagellin that has been modified to delete a fragment located between the N- and C-terminii that are known to interact with a TLR. For example, deletion of the region of the *Salmonella* flagellin of amino acids about 176 to about 402 inclusive leaves regions about 1 to about 175 and about 403 to about 495 that may interact with TLRs. It may be advantageous to remove this antigenic fragment to reduce unfavorable host responses, such as excessive inflammation, previously acquired immune responses, and the like that may result in inactivation of the administered adjuvant modified flagellin once administered to an animal or human host. In embodiments, such a deleted fragment may be replaced with a linker peptide, while in other embodiments the fragment may be replaced with an antigenic or immunogenic peptide derived from a heterologous source. In some embodiments, the modified flagellin polypeptide may also include a heterologous signal peptide sequence and/or a heterologous transmembrane and cytoplasmic domain from other sources, such as viral sources, including influenza hemagglutinin, MMTV Env peptides, and the like. Such embodiments are described in additional detail in FIGS. 21-23.

The adjuvant molecules of the present disclosure may be co-administered with an antigenic composition or may be physically incorporated with the antigen or immunogen. For example, the adjuvant molecule may be incorporated into, or otherwise physically linked to, an antigenic compound, such as a VLP. Embodiments of the adjuvant molecule, therefore, may be a membrane-anchored surface protein that is incorporated into a VLP. In one embodiment of the present disclosure, the adjuvant molecule may be a membrane-anchored flagellin that is incorporated onto the surface of a VLP, to produce a chimeric VLP (cVLP). In other embodiments of the disclosure, the immunogenic compositions may comprise a VLP co-administered with a flagellin as the adjuvant molecule, where the flagellin is not incorporated into the VLP. Additional details about VLPs and chimeric VLPs are described in U.S. patent application Ser. Nos. 10/514,462 and 11/397,830, which are herein incorporated by reference in their entireties. The adjuvant molecule of the present disclosure can also be used with other antigen-presenting systems, such as virosomes as described, for example, in PCT Patent Application No. PCT/US2007/073342, which is hereby incorporated herein by reference in its entirety.

Immunogenic Compositions Including VLPs.

Embodiments of the immunogenic compositions of the present disclosure include chimeric virus-like particles (cVLPs) with adjuvanted characteristics as described above, and derived from viruses selected from, but not limited to, human immunodeficiency virus (HIV), feline immunodeficiency virus (FIV), bovine immunodeficiency virus, bovine leukemia virus, equine infectious anemia virus, human T-leukemia virus, Bunya virus, Lassa fever virus, Rift Valley virus, ebola virus, coronavirus, arenavirus, filovirus, influenza virus, paramyxovirus, rhabdovirus, alphavirus, flavivirus, herpesvirus; hanta virus; hepadna virus, cytomegalovirus, and the like.

Embodiments of the present disclosure, therefore, further provide methods of using the virus-like particles, and methods of making virus-like particles that can be used in immunogenic compositions to treat conditions in a host, and the immunogenic compositions that include virus-like particles.

Figure 24:
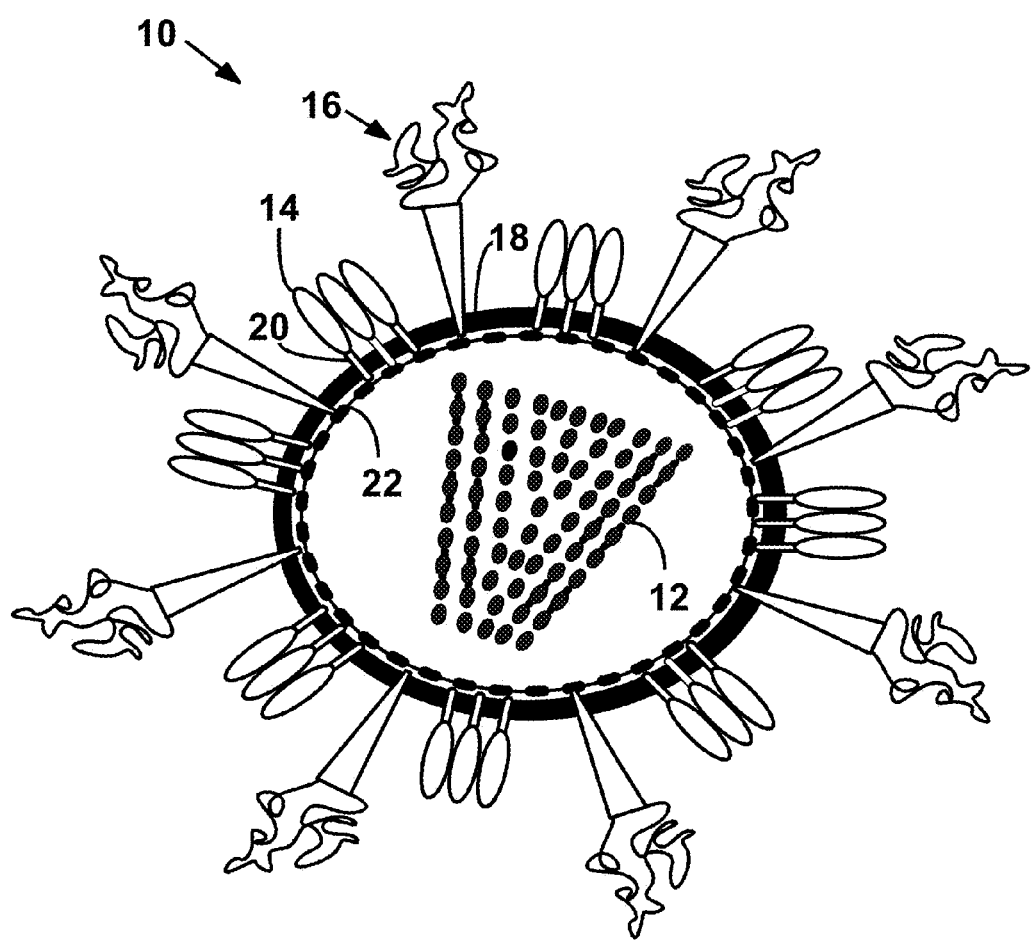
FIG. 24 is an illustration of a representative virus like particle (VLP) according to the present disclosure.

Referring now to FIG. 24, a virus-like particle (VLP) 10 according to the present disclosure comprises at least a viral core protein 12 (hereinafter "viral protein") and at least one viral surface envelope glycoprotein 14. The viral surface envelope glycoprotein 14 may be selected from, but is not limited to type 1 (14a) or type 2 (14b) viral surface envelope glycoproteins. In some embodiments of the disclosure, the VLP 10 can include at least one adjuvant molecule 16 according to the present disclosure incorporated onto the lipid membrane 18 of the VLP 10. In other embodiments, the adjuvant molecule may be co-administered with the VLP, but is not incorporated into the VLP itself. The adjuvant molecule 16 may be a surface protein (such as a bacterial flagellin) that may selectively target a host cell TLR. It is contemplated that the VLPs of the present disclosure may comprise more than one type of adjuvant molecule (e.g. 16a, 16b, and so on). In some embodiments, the adjuvant molecule 16 may be a membrane-anchored form of a surface protein, such as but not limited to, a membrane-anchored form of a bacterial flagellin such as described in the examples below.

Furthermore, the VLP may comprise a lipid membrane 18, viral glycoprotein transmembrane unit 20, and a matrix protein 22. In particular, chimeric VLPs (cVLPs) are VLPs having at least one viral surface envelope glycoprotein 14 incorporated into the VLP 10, wherein the viral core protein 12, and at least one viral surface envelope glycoprotein 14, may be from different viral sources. Thus, cVLPs also include VLPs wherein there are more than one type of viral surface envelope glycoprotein 14 (14a, 14b, and the like), and wherein one or both of 14a and 14b are from a different virus than the viral core protein 12.

Such cVLPs may or may not have the adjuvant molecule 16 incorporated into the VLP 10. In embodiments of the disclosure, the cVLPs may have at least one adjuvant molecule 16 incorporated into the VLP, where the adjuvant molecule(s) 16 may comprise a bacterial surface protein, such as a bacterial flagellin, or a fragment thereof, that targets a host TLR. Embodiments of the disclosure also include phenotypically mixed VLPs where there is more than one type of adjuvant molecule 16, such as 16a and 16b, where one or both of 16a and 16b are from a different bacterial source from each other.

Viral core proteins 12 include proteins that are capable of self-assembling into a VLP core, as described by Freed, E. O., (2002) *J. Virol.*, 76: 4679-4687. The viral core proteins 12 can include, but are not limited to, such as a viral Gag protein, including a retrovirus gag protein (such as the HIV Gag viral protein 'HIV-1 NL43 Gag' (GenBank serial no. AAA44987), the simian immunodeficiency virus (SIV) Gag viral protein 'SIVmac239 Gag' (GenBank serial no. CAA68379), the murine leukemia virus (MuLV) Gag viral protein 'MuLV Gag' (GenBank serial no. S70394), or the human foamy virus Gag viral protein), a retrovirus matrix protein, a rhabdovirus matrix protein M protein such as the vesicular stomatis virus (VSV) M protein 'VSV Matrix protein' (GenBank serial no. NP041714), a filovirus viral core protein such as the Ebola VP40 viral protein 'Ebola virus VP40' (GenBank serial no. AAN37506), the Rift Valley Fever virus N protein 'RVFV N Protein' (GenBank serial no. NP049344), coronavirus M, E and NP proteins such as NP protein (GenBank serial no. NP040838), M protein (GenBank serial no. NP040835), E protein of Avian Infections Bronchitis Virus (GenBank serial no. CAC39303), and E protein of the SARS virus (GenBank serial no. NP828854), a bunyavirus N protein (GenBank serial no. AAA47114), an influenza M1 protein, a paramyxovirus M protein, arenavirus Z protein (e.g., a Lassa Fever Virus Z protein), a cytomegalovirus (CMV) core protein, a herpes simplex virus (HSV) core protein, and combinations thereof. Appropriate surface glycoproteins and/or viral RNA may be included to form the VLP 10.

In general, the viral core protein 12 sequence and the corresponding polynucleotide sequence can be found in GenBank and the access numbers can be obtained online at the National Center for Biotechnology Information (NCBI). In addition, the sequences identified for the viral proteins 12 above are only illustrative examples of representative viral proteins 12. Furthermore, variants that are substantially homologous to the above referenced viral proteins 12 and viral proteins 12 having conservative substitutions of the above referenced viral proteins 12 can also be incorporated into VLPs 10 of the present disclosure to enhance the immunogenic characteristics of VLPs.

The viral surface envelope glycoprotein 14, or at least a portion of the viral surface envelope glycoprotein 14, may be disposed on the surface of the VLP so that it can interact with target molecules or cells, such as the interaction between the HIV surface envelope glycoprotein and the B cell receptor to activate HIV envelope glycoprotein specific antibody-producing B cells, to produce immunogenic responses including antibody production.

The viral surface envelope glycoproteins 14 of the VLPs according to the present disclosure can include, but are not limited to, a retroviral glycoprotein such as the human immunodeficiency virus (HIV) envelope glycoprotein 'HIVSF162 envelope glycoprotein' (GenBank serial no. M65024), the simian immunodeficiency virus (SIV) envelope glycoprotein 'SIVmac239 envelope glycoprotein' (GenBank serial no. M33262), the simian-human immunodeficiency virus (SHIV) envelope glycoprotein 'SHIV-89.6p envelope glycoprotein' (GenBank serial no. U89134), the feline immunodeficiency virus (FIV) envelope glycoprotein 'feline immunodeficiency virus envelope glycoprotein' (GenBank serial no. L00607), the feline leukemia virus envelope glycoprotein 'feline leukemia virus envelope glycoprotein' (GenBank serial no. M12500), the bovine immunodeficiency virus envelope glycoprotein 'bovine immunodeficiency virus envelope glycoprotein' (GenBank serial no. NC001413), the bovine leukemia virus envelope glycoprotein (GenBank serial no. AF399703), the equine infectious anemia virus envelope glycoprotein (GenBank serial no. NC001450), the human T-cell leukemia virus envelope glycoprotein (GenBank serial no. AF0033817), the human foamy virus glycoprotein, the mouse mammary tumor virus envelope glycoprotein (MMTV), a bunya virus glycoprotein such as the Rift Valley Fever virus (RVFV) glycoprotein 'RVFV envelope glycoprotein' (GenBank serial no. M11157), an arenavirus glycoprotein such as the Lassa fever virus glycoprotein (GenBank serial no. AF333969), a filovirus glycoprotein such as the Ebola virus glycoprotein (Gen Bank serial no. NC002549), the coronavirus glycoprotein (GenBank serial no. AAP13567), an influenza virus glycoprotein (GenBank serial number V01085), a paramyxovirus glycoprotein such as the Nipah virus F and G proteins (Gen Bank serial no. NC002728), a rhabdovirus glycoprotein such as Vesicular Stomatitis Virus (VSV) glycoprotein (Gen Bank serial no. NP049548), an alphavirus glycoprotein such as Venezuelan equine encephalomyelitis (VEE) (Gen Bank serial no. AAA48370), the flavivirus glycoprotein such as West Nile virus (GenBank serial no. NC001563), a Hepatitis C Virus glycoprotein, a Herpes Virus glycoprotein, a cytomegalovirus (CMV) glycoprotein, a Respiratory Syncytial virus (RSV) glycoprotein, a rabies virus glycoprotein, a Marburg virus glycoprotein, and combinations thereof.

In general, the viral surface envelope glycoprotein 14 sequence and the corresponding polynucleotide sequence can be found in GenBank and the access numbers can be obtained online at NCBI. In addition, the sequences identified for the viral surface envelope glycoproteins 14 above are only illustrative examples of representative viral surface envelope glycoproteins 14. Further, variants that are substantially homologous to the above referenced viral surface envelope glycoproteins 14 and viral surface envelope glycoproteins 14 having conservative substitutions of the above referenced viral surface envelope glycoproteins 14 can also be incorporated into VLPs 10 of the present disclosure to enhance the immunogenic characteristics of VLPs.

In embodiments of the disclosure where the adjuvant molecule 16 is incorporated into the VLP, the adjuvant molecule 16, or at least a portion of the adjuvant molecule 16, is disposed on the surface of the VLP 10. The adjuvant molecule 16 may interact with other molecules or cells, such as mucosal surfaces having sialic acid residues thereon, and antigen-presenting cells such as dendritic cells, follicular dendritic cells, and the like.

The adjuvant molecule 16 may be, but is not limited to, monomeric or polymeric forms of a surface protein that targets a host TLR, such as, but not limited to a bacterial flagellin. For incorporation into the VLP, the adjuvant molecule should generally be a membrane-anchored form of the surface protein. Examples of membrane-anchored forms of mammalian TLR ligand molecules include, but are not limited to, ligands listed in Akira & Takeda (2004) Nature Revs/Immunol., 4: 499-511, which is incorporated by reference herein in its entirety. In particular, exemplary TLR ligand molecules include glycoproteins from *Prevotella intermedia*, respiratory syncytial virus protein F, fibronectin A domain, fibrinogen, flagellin, a measles virus HA protein, and Pam2Cys lipoprotein/lipopeptide (MALP-2). In addition to the surface protein adjuvant molecule, the VLPs of the present disclosure may also include one or more additional adjuvant molecules which may include, but are not limited to, an influenza hemagglutinin (HA) molecule (GenBank access no. J02090), a parainfluenza hemagglutinin-neuraminidase (HN) molecule (GenBank access no. Z26523 for human parainfluenza virus type 3 HN sequence information), a Venezuelan equine encephalitis (VEE) adjuvant molecule (GenBank access no. NC001449), a fms-like tyrosine kinase ligand (Flt3) adjuvant molecule (GenBank access no. NM013520), a C3d adjuvant molecule (Gen Bank access no. NM009778 for mouse C3 sequence; access no. NM000064 for human C3 sequence), a mannose receptor adjuvant molecule, a CD40 ligand adjuvant molecule (GenBank access no. M83312 for mouse CD40), and combinations thereof.

In general, the adjuvant molecule 16 sequence and the corresponding polynucleotide sequence can be found in GenBank and the access numbers can be obtained online at the NCBI. In addition, the sequences identified for the adjuvant molecules 16 above are only illustrative examples of representative adjuvant molecules 16. Further, variants that are substantially homologous to the above referenced adjuvant molecules 16 and adjuvant molecules 16 having conservative substitutions of the above referenced adjuvant molecules 16 can also be incorporated into VLPs 10 of the present disclosure to enhance the immunogenic characteristics of VLPs.

Methods of Making and Using the Immunogenic Compositions.

Embodiments of the present disclosure further include methods of inducing an immune response in a host by administering to the host an effective amount of an immunogenic composition according to the present disclosure. It is contemplated that the methods of the present disclosure are useful in preventing a disease or disorder by administering to an animal or human host in need thereof an effective amount of an immunogenic composition according to the present disclosure.

Embodiments of the disclosure further include methods of immunizing an animal or human host by administering to such a host an immunogenic composition of the present disclosure. In embodiments where the immunogenic composition includes a VLP that comprises a membrane-anchored form of an adjuvant molecule of the present disclosure incorporated into the VLP, the method may comprise expressing a viral core protein, at least one viral surface envelope surface glycoprotein, and at least one adjuvant molecule of the present disclosure in one or more host cells. It is contemplated, for example, that nucleic acid molecules encoding such proteins may be included in at least one expression vector nucleic acid which may be delivered to a recipient host cell. The viral core protein, at least one viral surface envelope glycoprotein, and at least one adjuvant molecule thus expressed by the host cell(s), may be assembled to form a VLP. The VLP can then elicit an immune response from the host animal or human, thereby providing future protection from infection by a pathogen corresponding to the proteins expressed by the VLP.

Methods of Making the Immunogenic Compositions of the Present Disclosure.

Embodiments of the present disclosure also include methods of making the immunogenic compositions of the present disclosure. Some exemplary methods of making the adjuvant molecules of the present disclosure are described below, including methods of making membrane-anchored forms of the adjuvant molecules. Methods useful for the making VLPs of the present disclosure for administration with the adjuvant molecules of the present disclosure, or which incorporate adjuvant molecules into the VLP, may be found in U.S. patent application Ser. Nos. 10/514,462 and 11/397,830, which are herein incorporated by reference in their entireties, and which are also described below.

VLPs for use in the immunogenic compositions of the present disclosure can be produced by in vitro cell culture expression systems such as, but not limited to, recombinant baculovirus expression system (BEVS) (see, for example, Yamshchikov et al., (1995) Virology: 214, 50-58). Assembly of HIV or SIV virus-like particles containing envelope proteins may be performed using expression systems, such as, but not limited to, a baculovirus expression system (Yamshchikov et al., (1995) Virology: 214, 50-58), recombinant poxvirus expression system (MVA) (Wyatt et al., (1996), Vaccine: 15, 1451-1458), recombinant VSV, recombinant adenovirus, and recombinant DNA expression vectors. Preferably, the VLPs are produced using recombinant BEVS and recombinant poxvirus expression systems.

In general, VLPs can be produced by simultaneously introducing into a cell a viral core protein expression vector, a viral surface envelope glycoprotein expression vector, and/or an adjuvant molecule expression vector. The expressed viral core protein self-assembles into a VLP that incorporates the viral surface envelope glycoprotein and/or the adjuvant molecule. The viral surface envelope glycoprotein and/or the adjuvant molecule are expressed and disposed on the VLP surface. Thereafter, the cell produces the VLP (for example, Vero cells, chimeric and/or phenotypically mixed VLPs). The cells may be selected from, but are not limited to, insect cells (e.g., *Spodoptera frugiperda* Sf 9 and Sf21 cells), and mammalian cells such as, but not limited to, EL4 cells and HeLa cells. The expression elements for expressing the viral core protein, viral surface envelope glycoprotein, and adjuvant molecule can also be included together in a single expression vector, or can be included in two or more expression vectors.

In general, the viral protein expression vector can be produced by operably linking a coding sequence for a viral protein of a virus to an appropriate promoter (e.g., an early promoter, late promoter, or hybrid late/very late promoter). The viral protein expression vector can also be modified to form a viral protein expression construct. In addition, the viral surface envelope glycoprotein expression vector can be produced by operably linking a coding sequence for a viral surface envelope glycoprotein of a virus to an appropriate promoter (e.g., early promoter, late promoter, or hybrid late/very late promoter). The viral surface envelope glycoprotein expression vector can be modified to form a viral surface envelope glycoprotein expression construct. Similarly, the adjuvant molecule expression vector can be produced by operably linking a coding sequence for an adjuvant molecule to an appropriate promoter (e.g., early promoter, late promoter, or hybrid late/very late promoter). The adjuvant molecule expression vector can be modified to form an adjuvant molecule expression construct.

In other embodiments of the disclosure, polynucleotide sequences encoding for a viral core protein, at least one viral surface envelope glycoprotein, and at least one adjuvant molecule can be included in a single expression vector, or in two or more expression vectors. The one or more expression vectors can be introduced into a host cell, the proteins can be expressed in the cell, whereby the cell forms the VLP. In embodiments, each of the polynucleotide sequences encoding for the viral core protein, the viral surface envelope glycoprotein, and the adjuvant molecule is operably linked to an appropriate promoter (e.g., a baculovirus promoter, a recombinant Modified Vaccinia Ankara (MVA) promoter, a CMV promoter, an EF promoter, an adenovirus promoter, a recombinant VSV promoter, a recombinant adenovirus promoter, a recombinant alphavirus promoter, and a recombinant DNA expression vector). Appropriate promoters include, but are not limited to, a constitutive or inducible promoter; an early, late, or hybrid late/very late promoter.

Compositions and immunogenic preparations of the present disclosure, including vaccine compositions comprising the VLPs of the present disclosure which are capable of inducing protective immunity in a suitably treated host, and a suitable carrier therefore are provided. The vaccine preparations of the present disclosure can include an immunogenic amount of one or more VLPs, fragment(s), or subunit(s) thereof. Such vaccines can include one or more viral surface envelope glycoproteins and portions thereof, and adjuvant molecule and portions thereof on the surfaces of the VLPs, or in combination with another protein or other immunogen, such as one or more additional virus components naturally associated with viral particles or an epitopic peptide derived therefrom.

The immunogenic compositions and/or vaccines of the present disclosure may be formulated by any of the methods known in the art. They can be typically prepared as injectables or as formulations for intranasal administration, either as liquid solutions or suspensions. Solid forms suitable for solution in, or suspension in, liquid prior to injection or other administration may also be prepared. The preparation may also, for example, be emulsified, or the protein(s)/peptide(s) encapsulated in liposomes. The immunogenic compositions can be used, but it is not limited to, skin immunization, microneedle delivery, mucosal delivery, and/or intramuscularly.

The active immunogenic ingredients are often mixed with excipients or carriers, which are pharmaceutically acceptable and compatible with the active ingredient. Suitable excipients include but are not limited to water, saline, dextrose, glycerol, ethanol, or the like and combinations thereof. The concentration of the immunogenic polypeptide in injectable, aerosol, or nasal formulations is usually in the range of about 0.2 to 5 mg/ml. Similar dosages can be administered to other mucosal surfaces.

In addition, if desired, the vaccines may contain amounts of auxiliary substances such as wetting or emulsifying agents, pH buffering agents, and/or other agents, which enhance the effectiveness of the vaccine. Examples of agents which may be effective include, but are not limited to: aluminum hydroxide; aluminum phosphate, N-acetyl-muramyl-L-threonyl-D-isoglutamine (thr-MDP); N-acetyl-nor-muramyl-L-alanyl-D-isoglutamine (CGP 11637, referred to as nor-MDP); N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE); and RIBI, which contains three components extracted from bacteria: monophosphoryl lipid A, trehalose dimycolate, and cell wall skeleton (MPL+TDM+CWS) in a 2% squalene/Tween 80 emulsion. The effectiveness of the auxiliary substances may be determined by measuring the amount of antibodies (especially IgG, IgM or IgA) directed against the immunogen resulting from administration of the immunogen in vaccines which comprise the adjuvant in question. Additional formulations and modes of administration may also be used.

The immunogenic compositions and/or vaccines of the present disclosure can be administered in a manner compatible with the dosage formulation, and in such amount and manner as will be prophylactically and/or therapeutically effective, according to what is known to the art. The quantity to be administered, which is generally in the range of about 1 to about 1,000 micrograms of viral surface envelope glycoprotein per dose and/or adjuvant molecule per dose, more generally in the range of about 5 to about 500 micrograms of glycoprotein per dose and/or adjuvant molecule per dose, depends on the subject to be treated, the capacity of the hosts immune system to synthesize antibodies, and the degree of protection desired. Precise amounts of the active ingredient required to be administered may depend on the judgment of the physician or veterinarian and may be peculiar to each individual, but such a determination is within the skill of such a practitioner.

The vaccine or immunogenic composition may be given in a single dose; two dose schedule, for example two to eight weeks apart; or a multiple dose schedule. A multiple dose schedule is one in which a primary course of vaccination may include 1 to 10 or more separate doses, followed by other doses administered at subsequent time intervals as required to maintain and/or reinforce the immune response (e.g., at 1 to 4 months for a second dose, and if needed, subsequent dose(s) after several months). Humans (or other animals) immunized with the compositions of the present disclosure are protected from infection by the cognate virus.

It should also be noted that the vaccine or immunogenic composition can be used to boost the immunization of a host having been previously treated with a vaccine such as, but not limited to, DNA vaccine and a recombinant virus vaccine.

Construction of the Membrane-Anchored Flagellin Coding Sequence.

To incorporate flagellin into VLPs as a molecular adjuvant according to an embodiment of the present disclosure, the gene was modified to enable membrane translocation, transport, and cell surface expression. As schematized in FIG. 5, a membrane-anchored flagellin-encoding nucleic acid construct was prepared by merging, at the N terminus of the flagellin-encoding nucleic acid, the coding sequence for the signal peptide (SP) of the honeybee protein melittin. The transmembrane-cytoplasmic tail (TM-CT) from influenza hemagglutinin (HA) was added in-frame at the C-terminus of the flagellin-encoding nucleic acid. As a heterologous SP, melittin SP is known to improve glycoprotein cell surface expression in an insect cell system. The TM-CT sequence from HA provided a membrane anchor sequence to allow the modified flagellin to assemble into influenza virus matrix protein (M1)-derived VLPs (Ali et al., (2000) J. Virol. 74:8709-8719).

Figure 9:
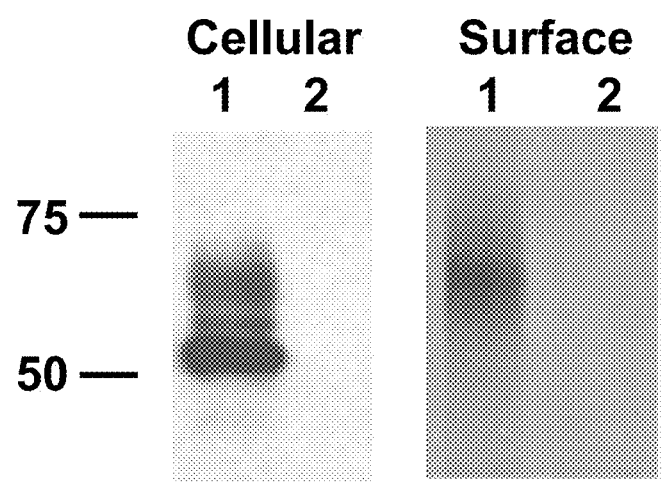
FIG. 9 is a digital image of a gel electrophoretic analysis of cellular and cell surface expression of membrane-anchored flagellin. Surface expression of the membrane-anchored flagellin was detected by cell surface biotinylation. Lane: 1, cell lysate from 5' and 3' ends membrane-anchored flagellin; Lane 2, mock rBV (rBV expressing human immunodeficiency virus Gag)-infected cells.

Recombinant baculovirus (rBV) was generated using the resulting membrane-anchored flagellin-encoding sequence. As shown in FIG. 9 (left panel), flagellin fused with the HA™-CT region could be expressed in rBV-infected Sf9 cells. The modified protein yielded two major bands in cell lysates by autoradiography (FIG. 9, left panel, lane 1). The lowest band is around 55 kDa and corresponds to the molecular mass estimated according to its amino acid composition in a non-glycosylated form. The top band is about 65 kDa, indicating that glycosylation of this modified protein occurred in the insect cell protein expression system. Other bands between the two main bands are possibly due to differences in glycosylation of the membrane-anchored flagellin. As shown in FIG. 9, right panel, surface expressed flagellin corresponds to the top band with a molecular mass of 65 kDa, suggesting that only glycosylated flagellin is transported to cell surfaces.

Production of cVLPs Containing Flagellin.

Figure 10:
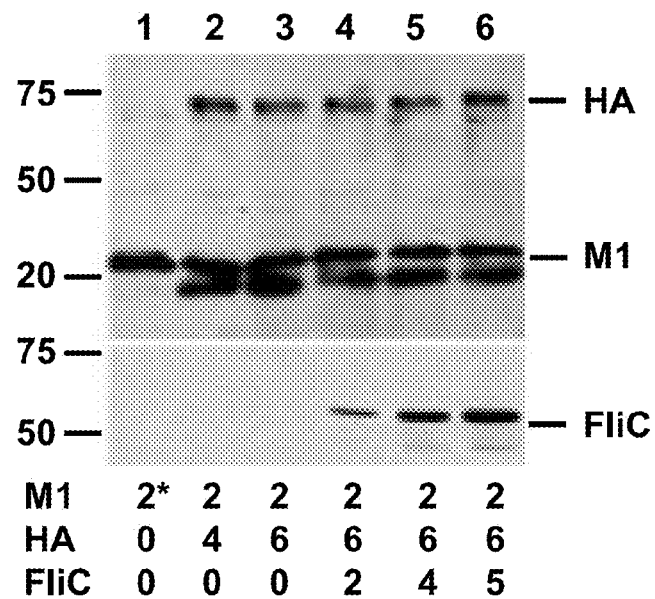
FIG. 10 is a digital image illustrating the optimization of VLP production: Sf9 cells were infected with rBVs expressing HA, M1, and flagellin at different MOI as designated below the image. HA and M1 bands were probed with mouse anti-influenza serum. The band below M1 was variable in different VLP preparations and may represent a degradation product. Membrane-anchored flagellin (FliC) was probed with rabbit anti-flagellin-specific polyclonal antibody.

In an embodiment VLPs were produced in an rBV-derived protein expression system in Sf9 insect cells and purified by gradient centrifugation. To optimize the production of cVLPs, rBVs expressing HA, M1, and flagellin were compared at various multiplicities of infection (MOI), as shown in FIG. 10, bottom. The results, in FIG. 10, top, demonstrate that standard influenza VLPs with a high HA content resulted from co-infection of HA- and M1-expressing rBVs at MOIs of 4 and 2, respectively, and the VLPs (total protein concentration, 1 mg/ml) have an HA titer as high as 2048 U when titrated with chicken blood cells.

Figure 11:
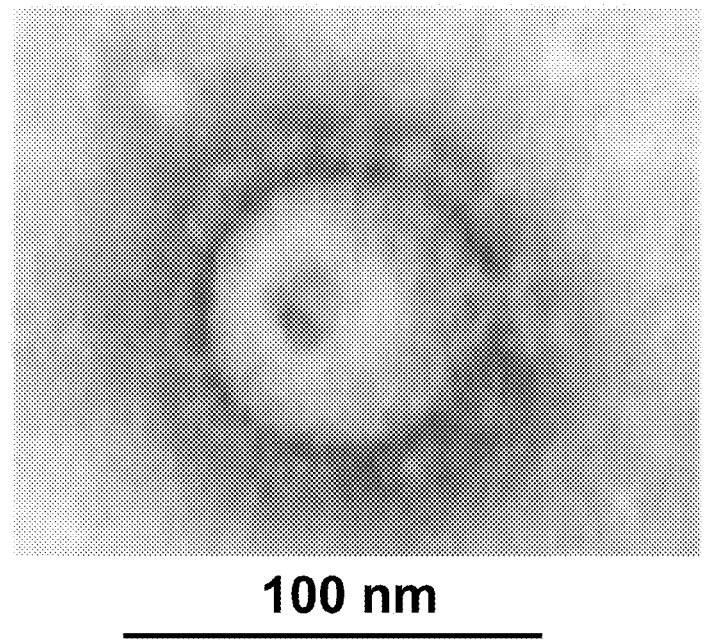
FIG. 11 is a digital electron microscopy image of influenza VLPs. Influenza VLPs containing flagellin, HA, and M were negatively stained

The cVLPs containing flagellin were produced by co-infection of rBVs expressing HA, M1, and flagellin at MOIs of 6, 2, and 6, respectively. These cVLPs had HA and M1 contents comparable to those of standard HA and M1VLPs, as shown by the Western blot results in FIG. 10 (*top*). The HA titer of the cVLPs (protein concentration, 1 mg/ml) was 2048 U, the same as that for standard VLPs. When purified recombinant flagellin was used as a standard, a Western blot comparison showed that the cVLPs have a flagellin content of about 8 μg/100 μg VLPs. To further confirm the morphology and integrity of these cVLPs, the cVLP samples were examined by electron microscopy after negative staining. As shown in FIG. 11, enveloped VLPs with projections on the surface were observed, with diameters of about 80 to about 100 nm. In addition, the cVLPs had morphological characteristics similar to those of standard HA/M1 VLPs, as described previously (Quan et al., (2007). J. Virol. 81:3514-3524). Membrane-anchored flagellin variants of the present disclosure, therefore, together with HA, is incorporated into M1-derived VLPs with a morphology and size similar to those of standard HA/M1VLPs and influenza virions.

Characterization of the Membrane-Anchored Flagellin incVLPs.

(i) In an embodiment there are six potential N-linked glycosylation sites in the flagellin sequence itself, with an NXT/S motif (Asn 19, 101, 200, 346, 446, and 465, respectively, and identified by arrows in FIG. 8). Four of them are located in the TLR-5-recognizing regions (Asn 19, 101, 446, and 465). To further characterize the possible glycosylation of the membrane-anchored flagellin in cVLPs, VLPs containing flagellin were treated with PNGase F or endo-H. PNGase F is an amidase that can remove N-linked oligosaccharides from glycoproteins, whereas endo-H cleaves the chitobiose core of high-mannose and hybrid oligosaccharides from N-linked glycoproteins.

Figure 12:
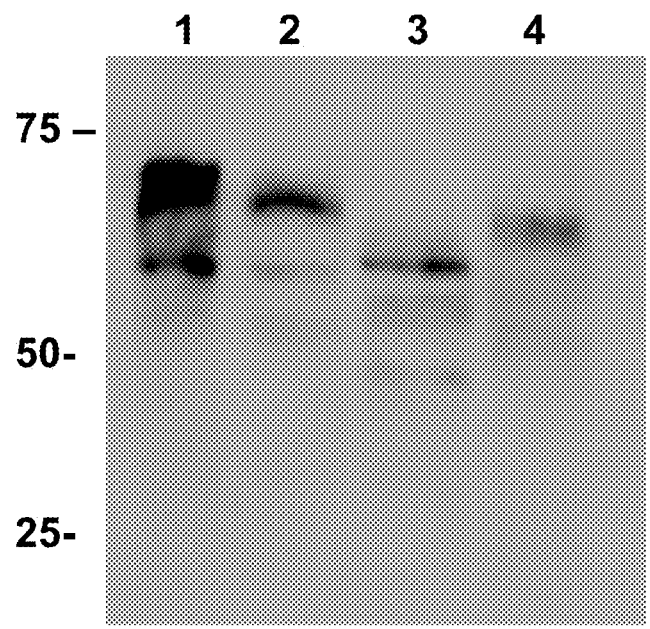
FIG. 12 is a digital image of a Western blot where 10 µg aliquots of flagellin-containing VLPs were left untreated (lane 2) or were digested by PNGase F (lane 3) or endo-H (lane 4). Lane 1 is cell lysate from cells infected by membrane-anchored flagellin expressing rBV.

As shown in FIG. 12, most of the modified flagellin in cell lysates is seen as two main portions on the blot with molecular masses of 55 and 65 kDa (lane 1). The flagellin incorporated into cVLPs corresponds to the upper band (65 kDa) (lane 2). After treatment of VLPs with PNGase F, flagellin bands of faster mobility at 55 kDa were observed (FIG. 12, lane 3), demonstrating that the membrane-anchored flagellin is glycosylated by N-linked oligosaccharides. When the glycosylated flagellin in VLPs was treated by endo-H, an intermediate band (around 60 kDa) was observed (FIG. 12, lane 4), revealing the partial sensitivity of the flagellin in VLPs to endo-H. These results indicate that at least some of the oligosaccharides are of the high-mannose type. In conclusion, these results indicate that flagellin in VLPs is glycosylated and that the oligosaccharides are linked to the flagellin peptide backbone by N-type glycosidic linkages.

Figure 13:
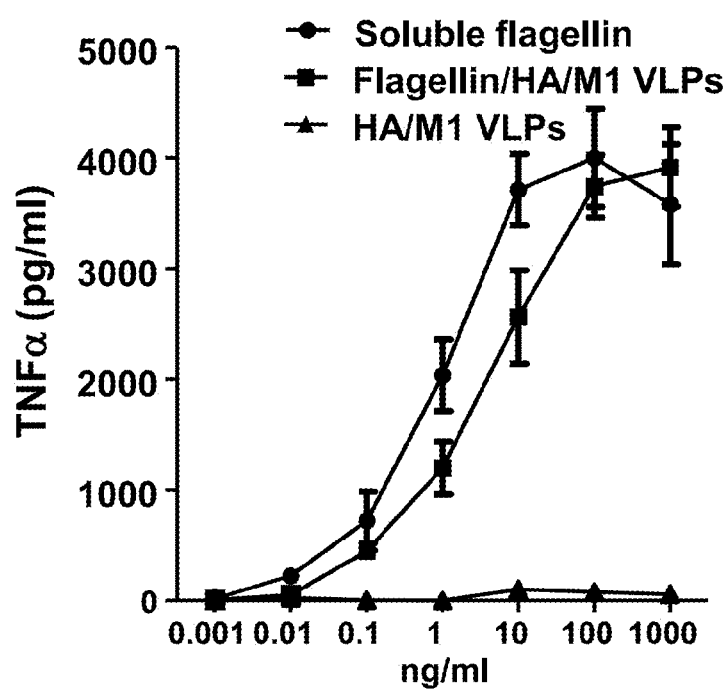
FIG. 13 is a graph of TLR-5 agonist activity of membrane-anchored flagellin. TLR-5-positive and -negative RAW264.7 cells were activated with soluble flagellin (sFliC) and flagellin-containing VLPs (FliC/HA/M1 VLPs), respectively. Standard HA/M1 VLPs were used as controls. TLR-5-specific bioactivity was expressed by the production by TNF-α of TRL-5-positive cells, from which was subtracted that of TLR-5-negative cells stimulated by flagellin, flagellin-containing VLPs, or standard HA/M1 VLPs at the same concentration. Data represent means±standard errors from triplicate repeats.

(ii) In an embodiment the adjuvant properties of flagellin are based on its TLR-5-activating activity. To evaluate the ability of the membrane-anchored flagellin in VLPs to function as a TLR-5 ligand, flagellin-containing VLPs were analyzed by a mouse macrophage cell line RAW264.7-based assay, and results were compared to those from purified soluble flagellin. As shown in FIG. 13, flagellin-containing cVLPs stimulated TLR-5-positive RAW264.7 cells to produce TNF-α over a broad concentration spectrum, similar to that seen with soluble flagellin. The 50% effective concentration (concentration which produces 50% of maximal activity) of flagellin-containing VLPs was about 8 ng/ml, whereas the 50% effective concentration of soluble flagellin was about 1 ng/ml. Because the flagellin content in cVLPs is about 8% by weight, the results indicate that the TLR-5 agonist activity of membrane-anchored flagellin in cVLPs is comparable to that of soluble flagellin.

cVLPs Containing Flagellin Induce Enhanced Humoral Immune Responses.

It is well recognized that flagellin in full length, truncated, or fusion protein forms enhances antigen specific antibody responses (Cuadros et al., (2004) Infect. Immun. 72:2810-28168; Honko et al., (2006). Infect. Immun. 74:1113-1120; McDonald et al., (2007) J. Infect. Dis. 195:1607-1617).

Figure 14A:
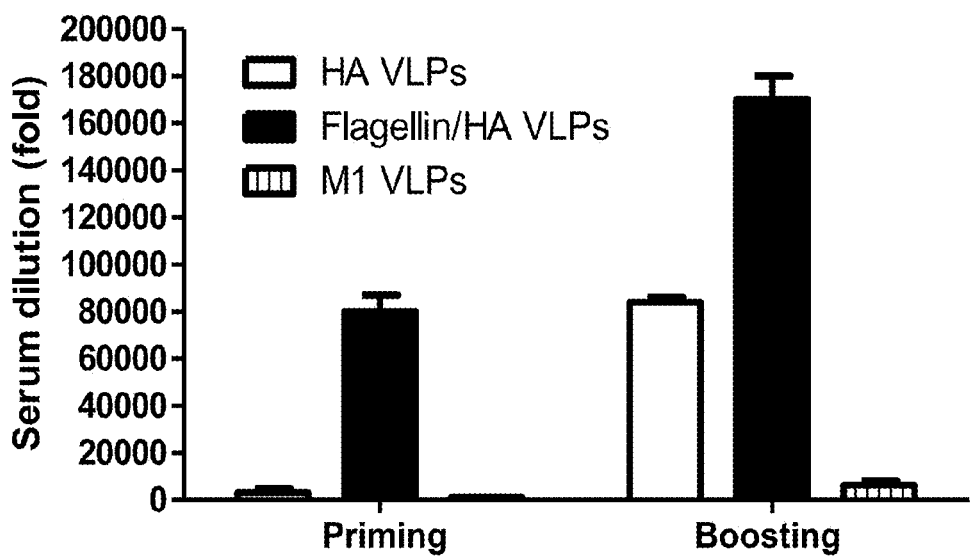
FIG. 14A shows a bar graphs illustrating serum IgG isotype endpoint titers. Serum antibodies specific for influenza A/PR8 virus were determined. The highest serum dilution (n-fold) which gave an $OD_{450}$ twice that of naive mice was designated as the serum antibody endpoint titer. Data are the mean±standard deviation (SD) of six mice per group, and were analyzed by an unpaired t test. A two-tailed P value of 0.05 is designated as a significant difference. sFliC: soluble flagellin.

To evaluate the ability of membrane-bound flagellin in influenza cVLPs to function as an adjuvant, the humoral immune response against influenza viral antigen was determined for mice immunized with standard HA/M1 VLPs or flagellin/HA/M1 cVLPs. As shown in FIG. 14A, high levels of serum antigen-specific IgG were promoted by priming or priming plus boosting for mice immunized with flagellin-containing cVLPs. A 2500-fold-higher IgG titer was achieved by the flagellin-containing VLP group after only the priming immunization compared with that of the standard HA/M1 VLP group, and this IgG level was comparable to that of the standard VLP group after two immunizations, demonstrating a significant enhancement of responses promoted by the incorporated flagellin. After two immunizations, the IgG level of the cVLP group remained two times higher than that of the standard VLP group (P 0.05). In contrast, when mice were immunized with mixtures of HA/M1 VLPs plus soluble recombinant flagellin, no significant difference in antibody response was detected compared to what was seen for HA/M1 VLPs alone. These results indicate that the incorporation of the membrane-anchored flagellin into VLPs is significant for its adjuvant effect.

Figure 14B:
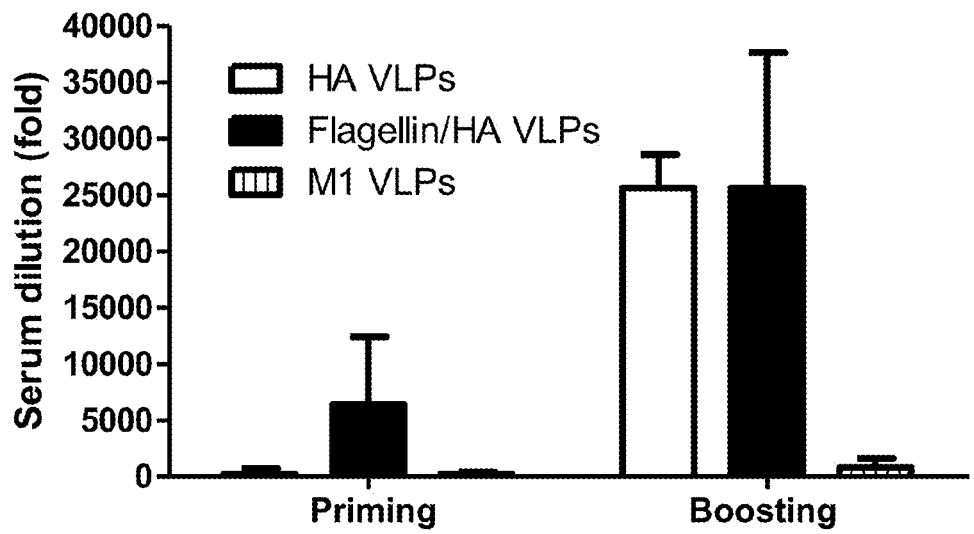
FIG. 14B shows a bar graph for IgG1 as in 14A.
Figure 14C:
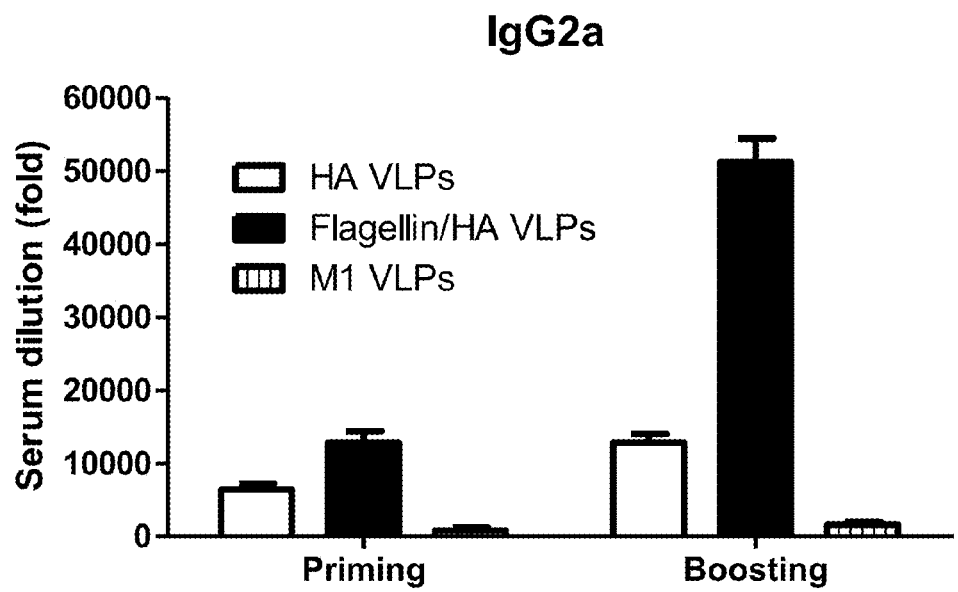
FIG. 14C shows a bar graph for IgG2a as in 14A.
Figure 14D:
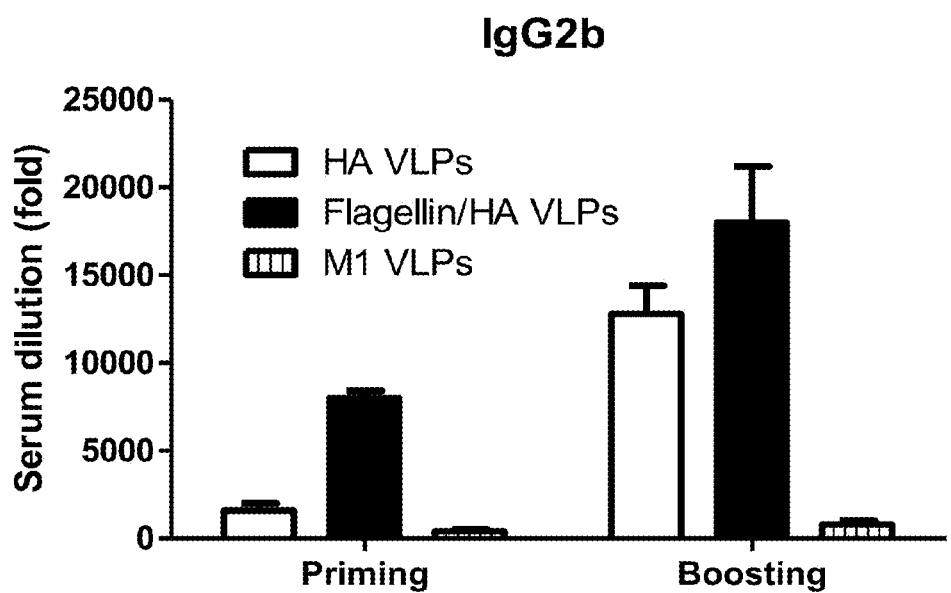
FIG. 14D shows a bar graph for IgG2b as in 14A.

Influenza VLP vaccines induce mixed Th1/Th2-type immune responses. To further evaluate the serum antibody response induced by flagellin, production levels of IgG subtypes IgG1, IgG2a, and IgG2b were determined. As shown in FIGS. 14B-14D, both standard VLPs and cVLPs promoted the production of all three IgG subtypes compared to what was seen for the control (M1-only) VLP group, demonstrating that both Th1 and Th2 immune responses were induced by VLP vaccines. However, the flagellin-containing VLPs elicited a level of IgG2a (IgG1/IgG2a ratio, 0.5) significantly higher than that seen for standard VLPs (IgG1/IgG2a ratio, 1.5; P 0.05), but this was not the case for IgG1, demonstrating that Th1-biased type-mixed responses and IgG2a-dominant class switching were effectively promoted by the incorporation of flagellin compared to standard VLPs.

Flagellin Stimulates Enhanced Virus Neutralization and HI Activity.

Figure 15A:
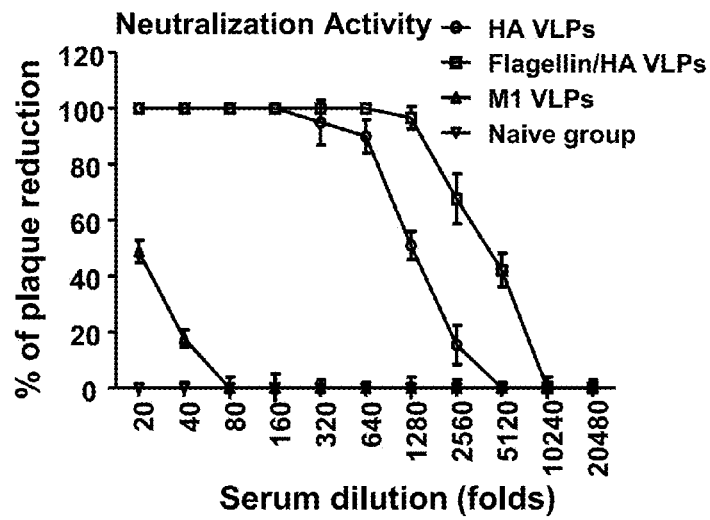
FIG. 15A shows data illustrating neutralization and HI titers against influenza A/PR8 virus, and the effect of preexisting anti-flagellin immunity. There is a graph illustrating neutralization activities determined using the capacity of sera to neutralize plaque formation by influenza PR8 virus in MDCK cell cultures. Serial dilutions of sera were incubated with influenza PR8 virus (about 100 PFU) at 37° C. for 1 h. A standard plaque reduction assay was performed using MDCK cells.
Figure 15B:
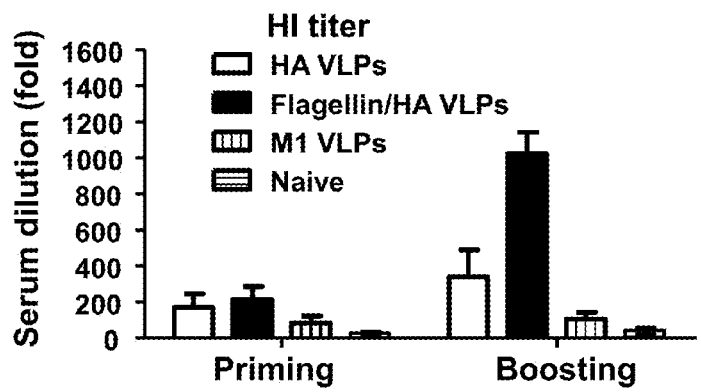
FIG. 15B is a bar graph illustrating HI titers of sera determined using the capacity of sera to inhibit virus hemagglutination of chicken red blood cells (*, P<0.05).

Virus neutralization activity is an important serological assay to reflect that functional antibodies provide protective immunity. To determine the effects of flagellin on conferring protective humoral responses, sera from mouse groups immunized with HA/M1 VLPs or flagellin-containing HA/M1 VLPs were evaluated for neutralization activities against PR8 virus. As shown in FIG. 15A, sera from standard VLP-immunized mice 3 weeks after the boost immunization showed a neutralization titer (50% plaque reduction) of 1280. In contrast, the flagellin-containing cVLP group showed a virus neutralization titer of 4000, more than threefold higher, revealing the effectiveness of flagellin incorporated into VLPs as an adjuvant. The enhanced responses were also demonstrated by the HI titers, which are based on blocking the ability of influenza HA to agglutinate erythrocytes by specific antibodies. As shown in FIG. 15B, the flagellin-containing cVLP group achieved an HI titer of 1080, three-fold higher than that of the standard VLP group (P 0.05), which had a mean HI titer of 360. The neutralization activity and HI titers were highly consistent, demonstrating that functional antibodies elicited by influenza VLPs are directed against the HA. Immune sera from the group immunized with a mixture of soluble flagellin plus HA/M1 VLPs also achieved levels of neutralization and HI titers similar to those of the standard HA/M1 VLP group.

Modified Flagellin Antigenicity.

Figure 15C:
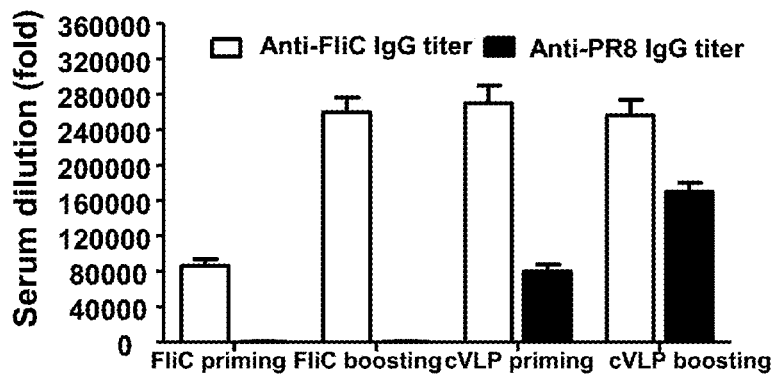
FIG. 15C is a bar graph illustrating the preexisting anti-flagellin IgG titer as determined with ELISA. Six mice were pre-immunized twice intramuscularly at a 4-week interval with 10 µg of soluble recombinant flagellin and subsequently immunized twice with 10 µg cVLPs at a 4-week interval. A six-mouse group without pre-immunization was used as the control. Serum anti-flagellin and anti-inactivated PR8 virus IgG titers were determined by ELISA. For flagellin-specific IgG titers, microplates were coated with 100 µl of recombinant flagellin per well at 5 µg/ml. Representative data are the mean±SD from six mice in each group. sFliC, soluble flagellin.

A concern for using a protein component as an adjuvant is the antigenicity of the protein itself, and pre-existing immunity against flagellin might block its further function as an adjuvant. To evaluate the effects of preexisting anti-flagellin antibody, mice were pre-immunized intramuscularly twice with 10 μg of recombinant flagellin. Subsequently, the same group was immunized twice with 10 μg of cVLPs at 4-week intervals. As shown in FIG. 15C, this resulted in a significant mean anti-flagellin IgG titer of $2.7 \times 10^5$, stable for 8 weeks. Interestingly, the PR8-specific IgG titers of flagellin-pre-immunized mice rose to levels similar to those of the cVLP control group without flagellin pre-immunization, as shown in FIG. 15C. Flagellin is an effective adjuvant to promote antigen-specific humoral responses when incorporated into the VLP embodiments of the present disclosure. Pre-existing flagellin immunity did not decrease its adjuvant function.

Figure 16A:
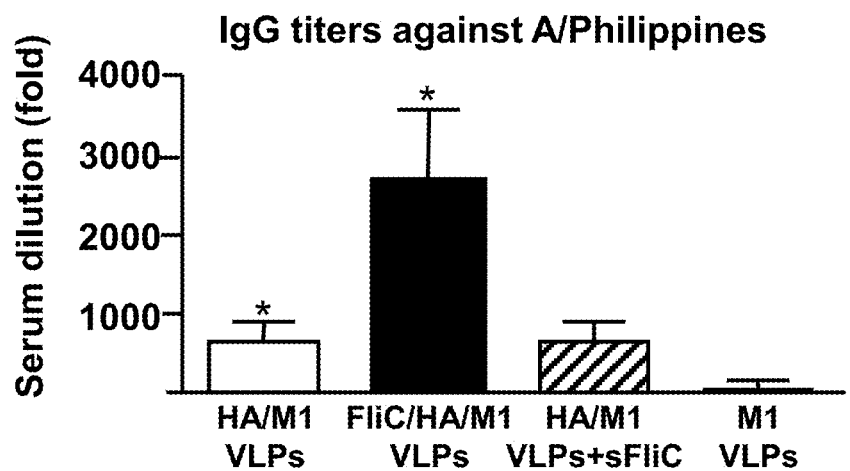
FIG. 16A is a bar graph illustrating the serum IgG endpoint, respectively, against the heterosubtypic virus A/Philippines (H3N2), respectively. Data depict the mean±SD from six mice per group (*, P<0.05). sFliC, soluble flagellin.
Figure 16B:
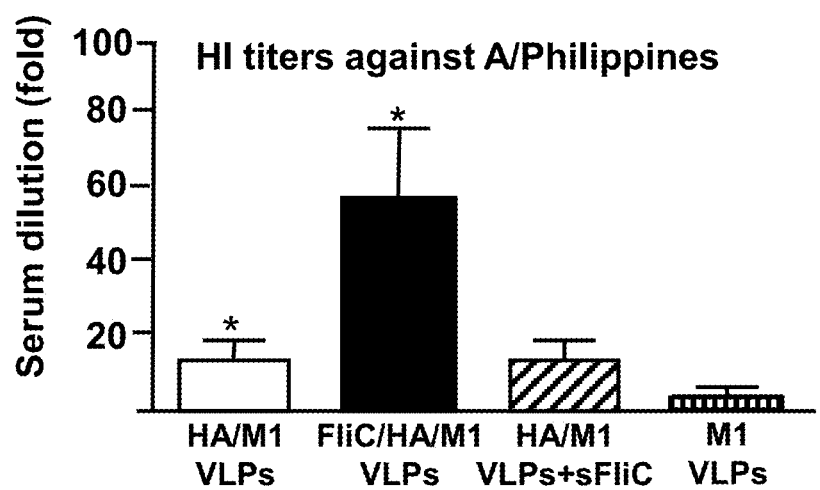
FIG. 16B shows a graph of HI titers as in FIG. 16A.
Figure 18A:
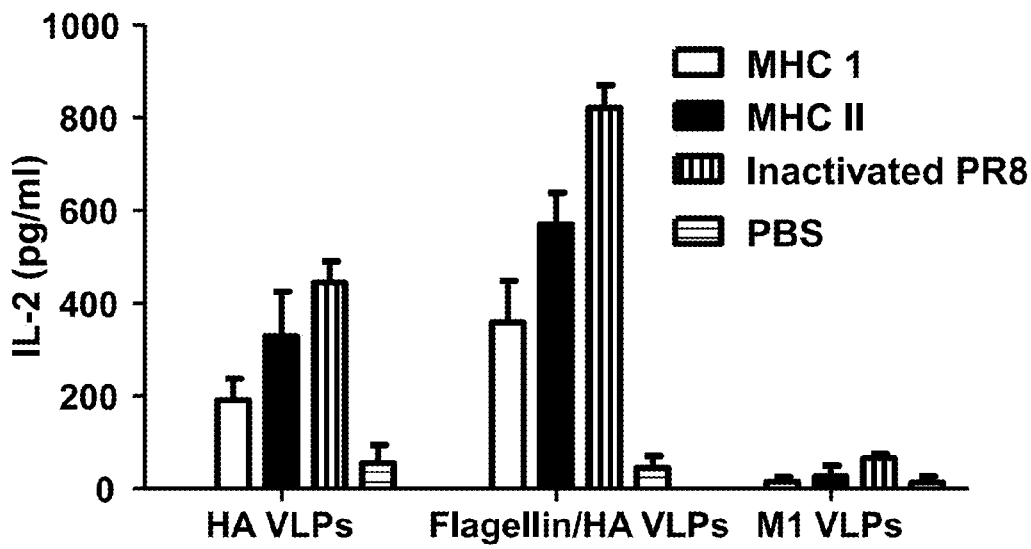
FIG. 18A shows a bar graph illustrating cytokine secretion IL-2 from immunized mouse splenocytes. Splenocytes were isolated from immunized six-mouse groups 3 weeks after the boosting immunization. Cells ($1 \times 10^6$) were seeded into 96-well cell culture plates with 200 µl RPMI 1640 medium. The MHC-I- or MHC-II-specific HA peptides of A/PR8 virus were added into cell culture medium, and secreted cytokines were determined. Data depict the mean±SD of six mice per group with similar results in triplicate assays (*, +, or ˆ, P<0.05). FliC: flagellin
Figure 18B:
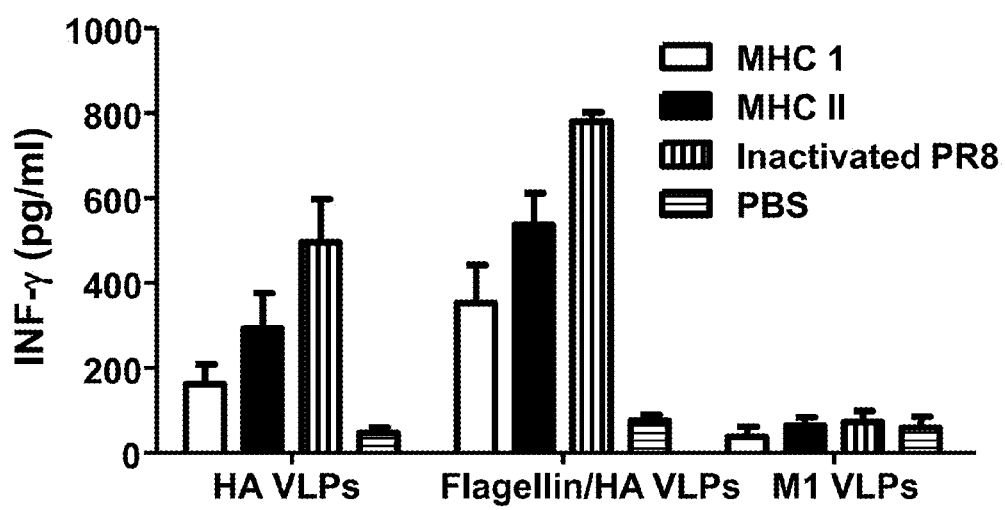
FIG. 18B shows a bar graph for IFN-γ as in FIG. 18A.
Figure 18C:
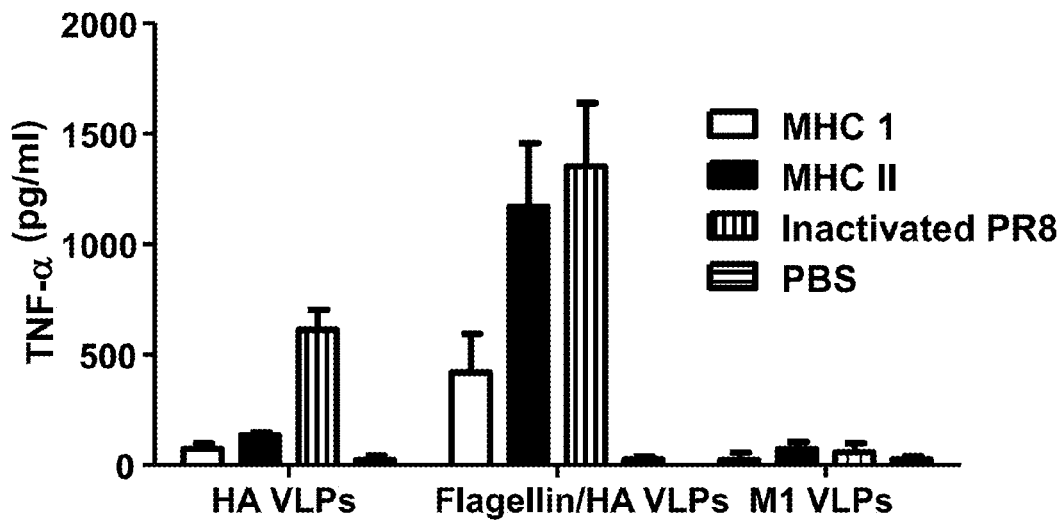
FIG. 18C shows a bar graph for TNF-α as in FIG. 18A.
Figure 18D:
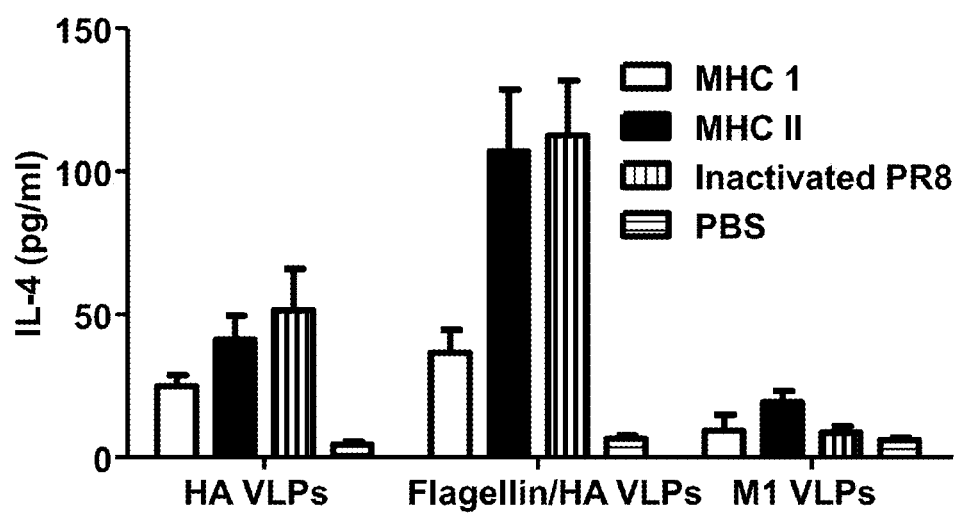
FIG. 18D shows a bar graph for IL-4 as in FIG. 18A.
Figure 19A:
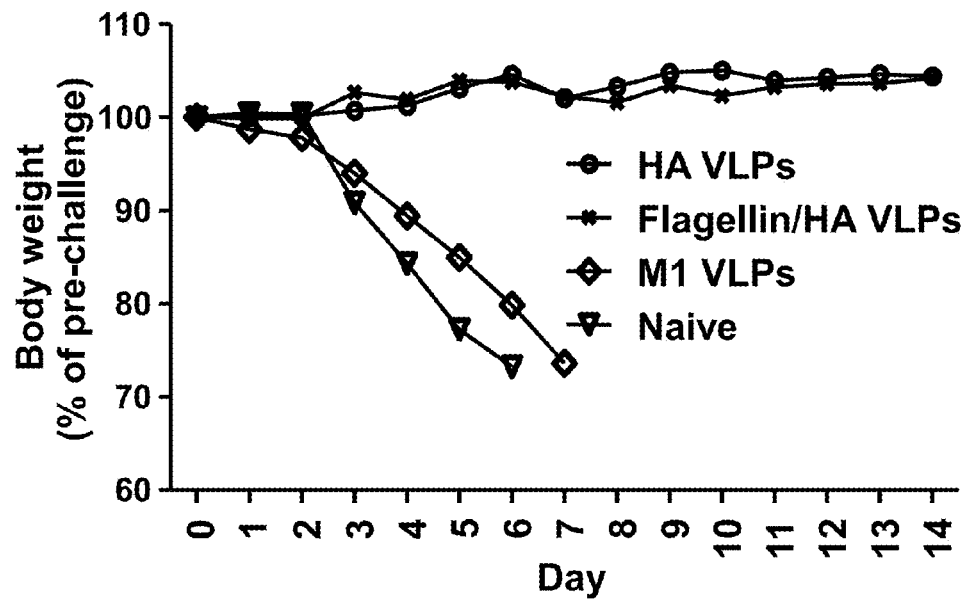
FIG. 19A shows a graph illustrating protection from challenge with A/PR8 or A/Philippines virus. Mouse groups containing six mice were challenged with $40 \times LD_{50}$ of PR8 ($H_1N_1$) or A/Philippines ($H_3N_2$) virus. Mice were monitored daily for 14 days for body weight changes. sFliC: soluble flagellin.
Figure 19B:
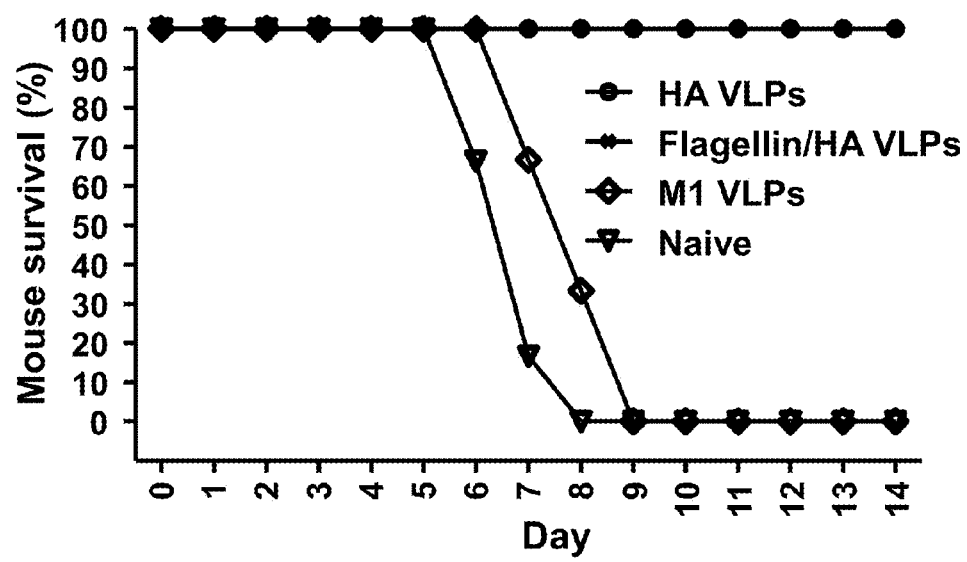
FIG. 19B shows a graph on percentages of survival as in FIG. 19A.
Figure 19C:
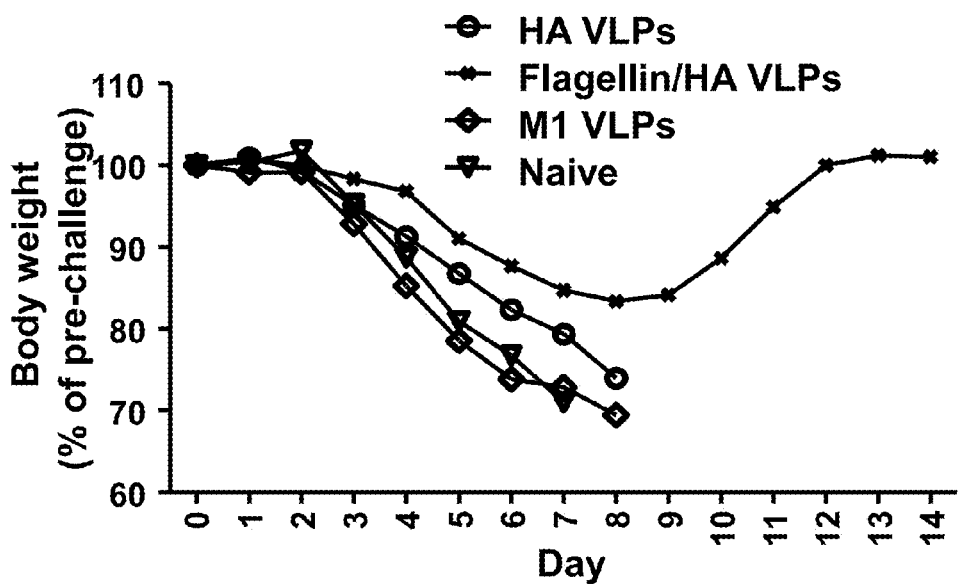
FIG. 19C shows a graph after PR8 virus challenge as in FIG. 19A.
Figure 19D:
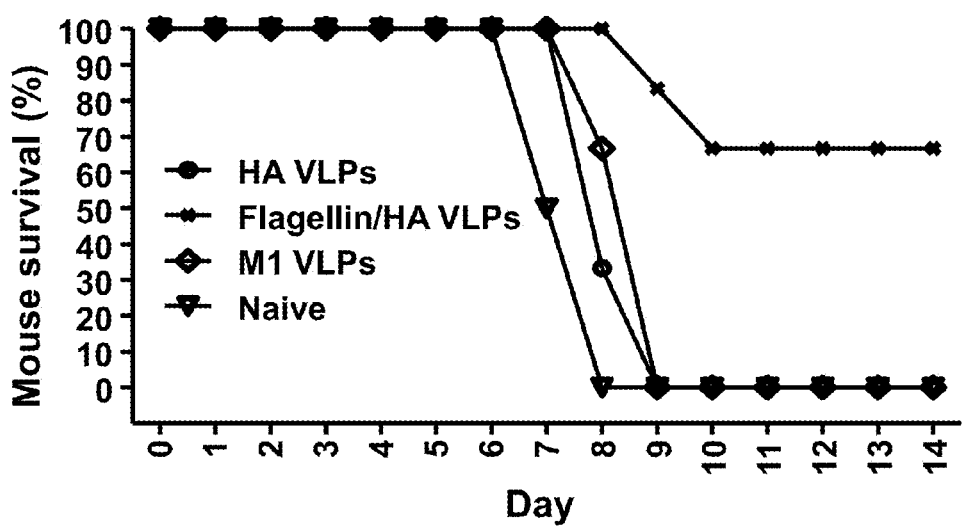
FIG. 19D shows a graph on percentages of survival after A/Philippines virus challenge as in FIG. 19A.
Figure 20:
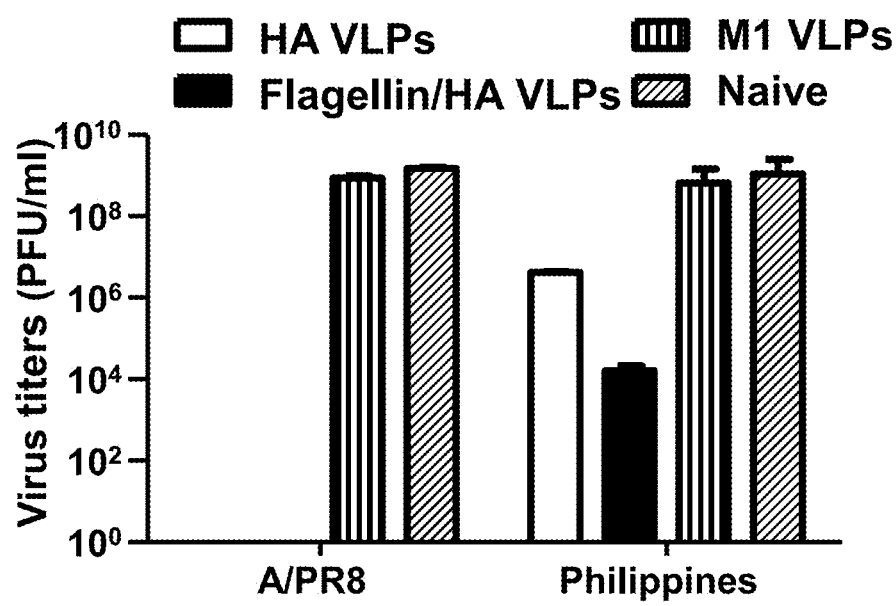
FIG. 20 is a bar graph illustrating lung viral load on day 4 post challenge. Six mice in each group were challenged with $40 \times LD_{50}$ of PR8 (H1N1) or A/Philippines (H3N2) virus. Mouse lung samples were collected on day 4 post challenge. Six lungs in each group were pooled, ground, and cleared in 6 ml of DMEM. Lung virus loads were determined using a standard plaque assay with MDCK cells. Bars represent mean virus titers standard errors from three independent assays (*, P<0.05). FliC, flagellin.

Because cVLPs induced significantly higher humoral responses, it was determined whether these immune sera could confer a cross-reaction with a heterosubtypic virus, by determining the serum IgG titer and HI titer against a heterosubtypic A/Philippines virus ($H_3N_2$). Though the humoral responses against A/Philippines were at low levels compared to those against A/PR8, flagellin-containing cVLPs induced significantly high IgG (2800) and HI (60)

titers against A/Philippines compared to those induced by standard VLPs (all P values were 0.05) (FIGS. 16A and 16B). The membrane-anchored flagellin of the present disclosure, therefore, broaden the spectrum of immunity to confer heterosubtypic immune responses.

Flagellin Promotes Antigen-Specific T-Cell Responses.

Several microbial products, such as lipopolysaccharide and CpG DNA, induce dendritic cell (DC) maturation by binding to TLR family molecules, including TLR-5 (Hemmi et al., (2000) Nature 408:740-745; Kaisho et al., (2001). J. Immunol. 166:5688-5694; McSorley et al., (2002) J. Immunol. 169:3914-3919; Takeuchi et al., (1999) Immunity 11:443-451). DCs are found in physical contact with naive T cells in vivo and, therefore, recognize microbial products and activate antigen-specific T-cell clonal expansion. To test the effects of membrane-anchored flagellin on enhancing the production of cytokines, cytokine secretions from splenocytes of mice immunized with the flagellin-containing cVLPs of the present disclosure were compared to those of the standard VLP-immunized mice. The results in FIGS. 18A-18D show that spleen T cells from mice immunized with flagellin-containing VLP secreted high levels of IL-2, IFN-γ, TNF-α, and IL-4 when stimulated by MHC-I or -II HA peptides, or inactivated PR8 virus, compared to those for the standard VLP group (all P values were 0.05). MHC-II-recognized HA peptides induced relatively higher levels of cytokine secretion, demonstrating a CD4-dominant memory T-cell population; both Th1 (IL-2 and IFN-γ)- and Th2 (TNF-α and IL-4)-type cytokine production was observed, but not detectable TNF-α secretion from splenocytes from the standard VLP group upon stimulation with either MHC-I or -IIHA peptides. However, splenocytes from flagellin-containing cVLP-immunized mice produced high levels of TNF-α.

Flagellin-Containing VLPs Promote Protective Immunity Against Lethal Virus Challenge.

To determine whether the enhanced antibody and T-cell responses as described above conferred protection against lethal virus challenge, immunized mice were challenged intranasally with mouse-adapted PR8 viruses at $40\times LD_{50}$. As shown in FIGS. 18A and 18B, mice immunized with standard VLPs, flagellin-incorporating VLPs, or a mixture of standard VLPs plus soluble flagellin, retained their healthy status as measured by body weight. These groups showed 100% protective immunity to lethal PR8 virus challenge. By contrast, no protection was observed using M1 VLPs, though mice immunized with M1 VLPs showed a minor improvement clinical score, as represented by body weight loss and a 1- to 2-day delay in reaching the endpoint upon lethal virus challenge compared to what was seen for the negative control group Because the flagellin-containing cVLP group showed much higher antibody levels and enhanced T cellular responses, we tested whether their enhanced immunity also can provide cross-protection to a heterologous virus challenge. Thus, immunized mice were challenged with an A/Philippines/82 $H_3N_2$ virus at $40\times LD_{50}$ per mouse. Data shown in FIG. 19C demonstrate that all VLP groups lost weight, as did the naive group, but the flagellin-containing cVLP-immunized group lost less weight. Though there was a 1-day delay compared to the control group, all mice in the standard VLP group or in the group immunized with the standard VLPs plus soluble flagellin, as well as those of the M1 VLP group, reached the endpoint by day 8 or 9. In the flagellin-containing cVLP-immunized group, however, mice began to regain body weight from day 9 (FIG. 19C), and 67% of mice survived the challenge with the heterologous A/Philippines virus, as shown in FIG. 19D.

Clearance of Virus Load from an Infected Host.

Rapid clearance of virus from the body and low virus loads after infection are important for decreased morbidity and mortality after infection. Immunized mice, therefore, were intranasally infected with A/PR8 or A/Philippines virus at the same dose as used in the challenge experiment (above). Mice were sacrificed on day 4, and the virus loads in lungs were determined by plaque assay on MDCK cells. As shown in FIG. 20, virus titers were not detected for either the standard or the flagellin-containing VLP groups in the PR8-infected mice. In contrast, naive mice and mice of the M1 VLP group were carrying high virus loads of $1.5\times10^9$ and $8.5\times10^8$ PFU/ml of lung extract, respectively. For A/Philippines virus-infected mice, the standard VLP group showed a lung virus titer of $4.2\times10^6$ PFU/ml of lung extract, whereas the flagellin-containing VLP group showed $1.6\times10^4$ PFU/ml of lung extract, a low titer when compared to that of standard cVLP group (P 0.05). The naive and M1 VLP groups showed titers of $1.5\times10^9$ and $8.7\times10^8$ PFU/ml of lung extract, respectively. These results demonstrated that by incorporating flagellin into VLPs as an adjuvant as disclosed in the present disclosure, influenza VLPs induce enhanced immunity, providing complete protection against a homologous virus challenge, and significant cross-protection against a heterosubtypic virus challenge.

The present disclosure, therefore, encompasses adjuvants for VLP and virosomal vaccines where the membrane-anchored form of *Salmonella* flagellin is incorporated as a modified flagellin into VLPs. By also fusing the SP-encoding DNA from honeybee protein melittin and the influenza HA TM-CT region to the *Salmonella* flagellin, the modified flagellin was efficiently expressed in insect cells with a baculovirus-derived protein expression system, and the expressed modified flagellin protein was presented on the cell surface. This membrane-anchored flagellin, together with HA, was also incorporated into M1-derived influenza VLPs.

The adjuvant function of flagellin is derived from its capacity for binding TLR-5 and several reports have shown that soluble chimeric flagellins in-frame fused to an antigen at the C terminus of the flagellin region retain both TLR-5-binding capacity and can promote the immunogenicity of the antigen itself (Cuadros et al., (2004) Infect. Immun. 72:2810-2816; Huleatt et al., (2008) Vaccine 26:201-214; McDonald et al., (2007) J. Infect. Dis. 195:1607-1617). Embodiments of the present disclosure introduce the HA membrane anchor at the C terminus of flagellin. The TLR-5 agonist activity of membrane-anchored flagellin in VLPs was verified by a TLR-5 bioactivity assay, and the ability of the membrane-anchored flagellin to act as an adjuvant for VLP vaccines was shown in the immunization results.

Previously, the immune responses induced by influenza VLPs containing HA and M1 were shown (Quan et al., (2007) J Virol 81:3514-3524) and it was found that the influenza VLPs induced high levels of antibody responses. However, using the methods encompassed by the present disclosure, flagellin may be incorporated into VLPs. The cVLP embodiments of the disclosure induce antibody responses more rapidly, and to a greater extent, than those induced by standard VLPs.

Flagellin-incorporated cVLPs of the present disclosure also activated a Th1-preferred Th1/Th2 profile, as demonstrated by a lower IgG1/IgG2a ratio. Standard VLPs and flagellin-containing cVLPs induced comparable levels of IgG1. However, embodiments of the flagellin-containing VLPs of the disclosure induced a fourfold-higher level of IgG2a production. Therefore, membrane-anchored flagellin variant embodiments of the present disclosure differ significantly from recombinant soluble flagellin, which induces a Th2 phenotype (Didierlaurent et al., (2004) J. Immunol. 172:6922-6930). The response induced by the membrane-anchored flagellin variants as used in the embodiments of the present disclosure are similar to flagellin in its native surface-bound context on live Salmonella bacteria, as described by Cunningham et al., (2004) Eur. J. Immunol. 34:2986-2995.

Splenocytes from mice immunized with embodiments of the flagellin-containing VLPs of the present disclosure produced high levels of IL-2, IFN-γ, TNF-α, and IL-4 when stimulated by HA-specific MHC-I or -II-restricted peptides, indicating the induction of antigen-specific T cells after immunization. Higher levels of cytokine production stimulated by an MHC-II HA-specific peptide demonstrated that flagellin primed a CD4-dominant T-cell response.

The flagellin-containing VLPs of the present disclosure primed a high level of TNF-α secretion, whereas TNF-α secretion of splenocytes as induced by standard VLPs remained at the background level. The high-level production of TNF-α induced by flagellin-containing VLPs and the enhanced specific immunity show that TNF-α plays an important role in activating adaptive immunity in flagellin-containing VLP immunization.

Mice pre-immunized with soluble recombinant flagellin produce high levels of flagellin-specific IgG responses. However, such pre-existing immunity against flagellin did not block the adjuvant function of membrane-anchored flagellin in VLPs, consistent with flagellin being an effective adjuvant even in the presence of pre-existing anti-flagellin immunity. While not wishing to be bound by any one theory, pre-existing anti-flagellin antibody might enhance the targeting of cVLPs to antigen-presenting cells (APCs) by the Fc portion of the cVLP-bound anti-flagellin IgG, since APCs express Fcγ receptors. However, significant differences in responses with or without pre-existing anti-flagellin immunity were not observed.

In its native state, flagellin is glycosylated at six sites by O-linked β-acetylglucosamine (Schirm et al., (2004). J. Bacteriol. 186:2523-2531). Glycosylation has roles for both flagellar assembly and biological function (Logan, S. M. (2006) Microbiology 152:1249-1262). In the N- and C-termini of Salmonella flagellin, which are both recognized by TLR-5, four N-linked glycosylation sites are located, at Asn19 and Asn101 in the N-terminal region, and at Asn446 and Asn465 in the C-terminal region. For the insect cell-derived membrane-anchored flagellins of the disclosure, though the whole-cell lysate showed two bands at 55 and 65 kDa, the VLPs showed only the higher (65 kDa) molecular-mass form. It is known that insect cells mostly produce simple N-glycans with terminal mannose residues (Harrison & Jarvis (2006). Adv. Virus Res. 68:159-191). The glycosylated forms of flagellin variants of the present disclosure do retain potent adjuvant activity.

Mixtures of soluble flagellin plus antigen do not promote high antigen-specific immune responses, and the physical association of an antigen with flagellin (fusion protein of antigen with flagellin) may be necessary for the promotion of the specific immune responses (Huleatt et al., (2008) Vaccine 26:201-214; McDonald et al., (2007) J. Infect. Dis. 195:1607-1617). However, embodiments of membrane-anchored flagellin incorporated into VLPs, as disclosed in the present disclosure, boosted a strong specific immune response; a mixture of soluble flagellin and standard VLPs, however, failed to show a similar adjuvant effect. While not wishing to be bound by any one theory, because TLR-5 is expressed on the surfaces of APCs, an association with flagellin may result in the TLR-5-mediated uptake of antigens and consequent processing and presentation.

The goal of vaccines is to elicit protection against pathogens and an effective adjuvant should extend this protective effect by promoting the immunogenicity of specific antigens in vaccines, thereby increasing the magnitude and the duration of immunity. The flagellin-containing VLPs of embodiments of the present disclosure induced apparently complete protection against an homologous virus challenge, and partially cross-protected against heterologous virus challenge, a broader-spectrum immunity.

Except as noted hereafter, standard techniques for peptide synthesis, cloning, DNA isolation, amplification and purification, for enzymatic reactions involving DNA ligase, DNA polymerase, restriction endonucleases, and the like, and various separation techniques are those known and commonly employed by those skilled in the art. A number of standard techniques are described in Sambrook et al. (1989) *Molecular Cloning*, Second Edition, Cold Spring Harbor Laboratory, Plainview, N.Y.; Maniatis et al. (1982) *Molecular Cloning*, Cold Spring Harbor Laboratory, Plainview, N.Y.; Wu (ed.) (1993) *Meth. Enzymol.* 218, Part I; Wu (ed.) (1979) *Meth. Enzymol.* 68; Wu et al. (eds.) (1983) *Meth. Enzymol.* 100 and 101; Grossman and Moldave (eds.) *Meth. Enzymol.* 65; Miller (ed.) (1972) Experiments in Molecular Genetics, Cold Spring Harbor Laboratory, Cold Spring Harbor, N.Y., Old Primrose (1981) *Principles of Gene Manipulation*, University of California Press, Berkeley; Schleif and Wensink (1982) *Practical Methods in Molecular Biology*; Glover (ed.) (1985) DNA Cloning Vol. I and II, IRL Press, Oxford, UK; Hames and Higgins (eds.) (1985) Nucleic Acid Hybridization, IRL Press, Oxford, UK; Setlow and Hollaender (1979) *Genetic Engineering: Principles and Methods*, Vols. 1-4, Plenum Press, N.Y.

One aspect of the disclosure, therefore, provides adjuvant polypeptides comprising at least one domain capable of selectively interacting with a Toll-like receptor of an animal or human cell, and where the domain may be capable of increasing an immune response in a recipient host; and at least one heterologous region selected from the group consisting of a signal peptide region and a transmembrane-cytoplasmic tail region.

In one embodiment of the disclosure, the adjuvant polypeptide may comprise a first region, where the first region comprises a signal peptide; a second region, where the second region may comprise at least one domain capable of selectively interacting with a Toll-like receptor of an animal or human cell, and where the domain is capable of increasing an immune response in a recipient host; and a third region, where the third region may comprise a transmembrane-cytoplasmic tail peptide.

In embodiments of this aspect of the disclosure, in the adjuvant polypeptides thereof, at least one domain is capable of selectively interacting with a Toll-like receptor of an animal or human cell, and may be derived from a surface protein of a bacterial species, or of a protozoal species.

In some embodiments of the adjuvant polypeptide, the surface protein may be a protein of a bacterial or a protozoal flagellum, or a fragment thereof.

In one embodiment, the surface protein is a flagellin of the bacterial species *Salmonella enteriditis*.

In one embodiment of the adjuvant polypeptides of the disclosure, the adjuvant polypeptide may have the amino acid sequence SEQ ID NO.: 10, or a conservative variant thereof.

In another embodiment, the second region thereof may further comprise a peptide linker.

In yet another embodiment, the peptide linker has the amino acid sequence according to SEQ ID NO.: 18.

In one embodiment of the disclosure, the signal peptide may be a signal peptide of a bee melittin polypeptide.

In another embodiment of the disclosure, the transmembrane-cytoplasmic region may be derived from a hemagglutinin A polypeptide of the influenza virus.

Another aspect of the disclosure is nucleic acid molecules comprising; a region encoding a bacterial flagellin polypeptide, or a fragment thereof, wherein the flagellin polypeptide or fragment thereof may comprise at least one domain capable of specifically interacting with a Toll-like receptor of an animal or human cell; and at least one region selected from the group consisting of: a region encoding a heterologous signal peptide, and a region encoding a transmembrane-cytoplasmic tail capable of being incorporated into a virus-like particle or virosome.

One embodiment of this aspect of the disclosure may comprise: a region encoding a bacterial flagellin polypeptide, or a fragment thereof, wherein the flagellin polypeptide or fragment thereof comprises at least one domain capable of specifically interacting with a Toll-like receptor of an animal or human cell; a region encoding a heterologous signal peptide; and a region encoding a transmembrane-cytoplasmic tail capable of being incorporated into a virus-like particle or virosome.

In embodiments of this aspect of the disclosure, the heterologous signal peptide may be a bee melittin signal peptide, the trans-membrane-cytoplasmic tail may be from an influenza virus hemagglutinin.

In other embodiments, the nucleic acid molecules may comprise: a first nucleotide sequence encoding the amino acid sequence from amino acid positions about 1 to about 305 of sequence SEQ ID NO.: 10, or a conservative variant thereof; a second nucleotide sequence encoding the amino acid sequence from amino acid positions about 430 to about 565 of sequence SEQ ID NO.: 10, or a conservative variant thereof; and a third nucleotide sequence disposed between the first and the second nucleotide sequences, where the third nucleotide sequence encodes a region selected from the group consisting of; a region of a bacterial or protozoal surface protein polypeptide, a peptide linker, and an immunogenic peptide.

In one embodiment of this aspect of the disclosure, the first nucleotide sequence may be according to about position 1 to about position 615 of nucleotide sequence SEQ ID NO.: 9, or a conservative variant thereof; and the second nucleotide sequence may be according to about position 1293 to about position 1695 of nucleotide sequence SEQ ID NO.: 9, or a conservative variant thereof.

In one embodiment of the disclosure, the nucleic acid molecule may comprise the nucleic acid sequence SEQ ID NO.: 9, or a conservative variant thereof.

In one embodiment of the disclosure, the nucleic acid molecule may have the nucleic acid sequence SEQ ID NO.: 9.

In some embodiments of the disclosure, the nucleic acid molecule may be operably inserted into a nucleic acid expression vector.

In embodiments of the disclosure, the nucleic acid expression vector may be selected from the group consisting of: a plasmid, a baculovirus vector, a cosmid, a viral vector, a chromosome, a mini-chromosome, a modified vaccinia Ankara (MVA) vector, a plasmid, a recombinant poxvirus vector, and a recombinant adenovirus vector, an alphavirus vector, and a paramyxovirus vector.

Another aspect of the disclosure provides immunogenic compositions comprising: an adjuvant polypeptide comprising at least one region capable of selectively interacting with a Toll-like receptor protein of a host; and an immunogen capable of producing an immune response in a recipient host.

In one embodiment of this aspect of the disclosure, the immunogenic compositions may further comprise a virus-like carrier, wherein the virus-like carrier is selected from the group consisting of a virus-like particle and a virosome, and wherein the adjuvant polypeptide and the immunogen may be incorporated in the virus-like particle or the virosome. In these embodiments of the disclosure, the adjuvant polypeptide may be incorporated into the VLP or virosome.

In another embodiment, the adjuvant polypeptide may be a surface polypeptide of a bacterial species or of a protozoal species, or a modified variant of the surface polypeptide.

In yet another embodiment, the surface polypeptide is a bacterial flagellin.

In one embodiment of the disclosure, in the immunogenic composition, the flagellin may be of the bacterial species *Salmonella enteridis*.

In embodiments of this aspect of the disclosure, the modified variant of the adjuvant polypeptide may comprise at least one heterologous peptide region selected from the group consisting of a signal peptide region and a transmembrane-cytoplasmic tail region.

In other embodiments of the disclosure, the modified variant of the adjuvant polypeptide may comprise a first heterologous peptide region, where the first heterologous peptide region may be a signal peptide, and a second heterologous peptide region, wherein the second heterologous peptide region may be a transmembrane-cytoplasmic tail peptide.

In the embodiments of this aspect of the disclosure, the bacterial flagellin polypeptide may be a modified bacterial flagellin polypeptide modified by deletion of a region of a full-length bacterial flagellin polypeptide.

In other embodiments, the modified adjuvant polypeptide may further comprise a heterologous peptide region, where said region may be disposed between two domains of the adjuvant polypeptide, where each domain may be capable of selectively targeting a toll-like receptor protein of a host.

In yet other embodiments of the immunogenic compositions of the disclosure, the adjuvant polypeptide may further comprise a heterologous peptide region, wherein said region is antigenic.

In still other embodiments of the disclosure, the virus-like carrier may be a virosome, comprising: at least one viral surface envelope glycoprotein expressed on the surface of the virosome; and at least one adjuvant molecule expressed on the surface of the virosome, wherein the adjuvant molecule comprises a membrane-anchored form of a bacterial or protozoal surface component that is a mammalian toll-like receptor ligand molecule. In another embodiment of the disclosure, the virus-like carrier may be a virus-like particle and further comprises a viral core protein capable of self-assembling into a virus-like particle core.

In these embodiments, the viral core protein and at least one viral surface envelope glycoprotein may be from different viruses.

In these embodiments of the disclosure, the viral core protein may be selected from: a retrovirus Gag protein, a retrovirus matrix protein, a rhabdovirus M protein, a filovirus viral core protein, a coronavirus M protein, a coronavirus E protein, a coronavirus NP protein, a bunyavirus N protein, an influenza M1 protein, a paramyxovirus M protein, an arenavirus Z protein, a cytomegalovirus (CMV) core protein, a herpes simplex virus (HSV) core protein, or a combination thereof.

In these embodiments, also, the retrovirus gag protein may be selected from; a Human Immunodeficiency Virus (HIV) Gag protein, a Simian Immunodeficiency Virus (SIV) Gag protein, a human foamy virus Gag protein, or a Murine Leukemia Virus (MuLV) Gag protein.

In other embodiments, the viral core protein may be selected from: a Vesicular Stomatitis Virus (VSV) M protein, an Ebola Virus VP40 protein, a Lassa Fever Virus Z protein, or a combination thereof.

In still other embodiments, the viral surface envelope surface glycoprotein is selected from: a retrovirus/lentivirus glycoprotein, a bunyavirus glycoprotein, a coronavirus glycoprotein, an arenavirus glycoprotein, a filovirus glycoprotein, an influenza virus glycoprotein, a paramyxovirus glycoprotein, a rhabdovirus glycoprotein, an alphavirus glycoprotein, a flavivirus glycoprotein, a cytomegalovirus glycoprotein, a herpes virus glycoprotein, or a combination thereof.

In other embodiments of the disclosure, the retrovirus glycoprotein may be selected from: a human immunodeficiency virus (HIV) glycoprotein, a simian immunodeficiency virus (SIV) glycoprotein, a simian-human immunodeficiency virus (SHIV) glycoprotein, a feline immunodeficiency virus (FIV) glycoprotein, a feline leukemia virus glycoprotein, a bovine immunodeficiency virus glycoprotein, a bovine leukemia virus glycoprotein, an equine infectious anemia virus glycoprotein, a human T-cell leukemia virus glycoprotein, a mouse mammary tumor virus envelope glycoprotein (MMTV), a human foamy virus glycoprotein, or a combination thereof.

In other embodiments, the viral surface envelope surface glycoprotein may be selected from: an influenza virus glycoprotein, a Respiratory syncytial virus (RSV) glycoprotien, a Lassa Fever virus glycoprotein, an Ebola Virus glycoprotein, a Marburg virus glycoprotein, a VSV glycoprotein, a rabies virus glycoprotein, a hepatitis virus glycoprotein, a herpes virus glycoprotein, a CMV glycoprotein, or a combination thereof, In other embodiments of the disclosure, the virus-like particle may be a chimeric virus-like particle comprising an influenza hemagglutinin, a matrix protein M1, and a modified bacterial flagellin adjuvant polypeptide, wherein the modified bacterial flagellin comprises a heterologous transmembrane-cytoplasmic tail and is incorporated into the chimeric virus-like carrier, and wherein the virus-like carrier is a virus-like particle or a virosome.

In the embodiments of this aspect of the disclosure, the immunogenic compositions may further comprise a pharmacologically acceptable carrier.

Still another aspect of the disclosure are methods of generating an immunological response in an animal or human comprising: exposing the immune system of an animal or human host to an immunogen and a virus-like carrier, wherein the virus-like carrier may be a virus-like particle or a virosome, and where the virus-like carrier may comprise an adjuvant polypeptide comprising a host cell Toll-like receptor ligand polypeptide derived from a bacterial or protozoal flagellum polypeptide, and at least one heterologous peptide selected from the group consisting of a transmembrane-cytoplasmic tail polypeptide and a heterologous signal peptide; thereby generating in the recipient host an immune response directed against the immunogen.

In embodiments of this aspect of the disclosure, exposing the host to the virus-like particle may comprise: delivering to the recipient host or host cell at least one expression vector, where the at least one expression vector or a multiplicity of expression vectors comprise at least one polynucleotide encoding at least one polypeptide selected from the group consisting of: a viral core protein, a viral surface envelope glycoprotein, and an adjuvant molecule, where each of the polynucleotide or polynucleotides is operably linked to an expression control region; expressing in the recipient host or host cell at least one viral surface envelope glycoprotein, and at least one adjuvant molecule, thereby assembling a virosome virus-like carrier.

In one embodiment of this aspect of the disclosure, an expression vector may further comprise a polynucleotide encoding a viral core protein, wherein the viral core protein is incorporated into a virus-like particle.

In various embodiments of this aspect of the disclosure, one or more vectors may be selected from the group consisting of: a plasmid, a cosmid, a viral vector, an artificial chromosome, a mini-chromosome, a baculovirus vector, a modified vaccinia Ankara (MVA) vector, a recombinant poxvirus vector, a recombinant VSV vectors, a recombinant adenovirus expression systems, an alphavirus vector, a paramyxovirus vector, or a combination thereof Yet another aspect of the disclosure provides methods of immunizing a host comprising: co-expressing in one or more host cells at least one viral surface envelope surface glycoprotein, and at least one adjuvant molecule; whereby the at least one viral surface envelope glycoprotein and the adjuvant molecule assemble to form a virus-like carrier, and wherein the at least one adjuvant molecule is a mammalian toll-like receptor ligand molecule.

Embodiments of this aspect of the disclosure may further comprise co-expressing a viral core protein, wherein the co-expressed viral core protein is assembled into the virus-like carrier, thereby forming a virus-like particle.

In embodiments of this aspect of the disclosure, the at least one adjuvant molecule may be a bacterial flagellin molecule.

In other embodiments of the disclosure, the at least one adjuvant molecule may assemble with the viral core protein and the at least one viral surface envelope glycoprotein to form a VLP, wherein the at least one adjuvant molecule may be a membrane-anchored variant of a bacterial surface protein that is a mammalian toll-like receptor (TLR) ligand molecule.

In other embodiments, the virus-like particle may be a chimeric virus-like particle comprising an influenza hemagglutinin, a matrix protein M1, and a modified bacterial flagellin adjuvant polypeptide, wherein the modified bacterial flagellin comprises a heterologous transmembrane-cytoplasmic tail and is incorporated into the chimeric virus-like particle, the chimeric virus-like particle inducing an immune response in the animal or human host and thereby inhibiting the development of influenza in the host.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

EXAMPLES

Example 1

Recombinant Monomeric Soluble Flagellin from *Salmonella enteritidis* Expressed in *E. coli*

A construct was generated to express wild type flagellin from the flagella filament protein gene FliC of *S. enteritidis*, and the protein was purified from *E. coli*. The flagellin gene was cloned into expression vector pET-22b(+) (Novigen) with NdeI/XhoI in-frame with a polyhistidine tag. *E. coli* strain BL(21) was used for the production of flagellin by IPTG induction. Five hours post-induction, cells were harvested and used for the isolation of flagellin with Nicklebead (Qiagen) affinity purification following the manufacturer's instruction. Purified soluble flagellin was characterized by gel electrophoresis and Coomassie Blue staining (as shown in FIG. 1A) and western blot analysis (as shown in FIG. 1B). Removal of LPS was determined as described.

Example 2

Isolating Polymeric Flagellin from *Salmonella enteritidis*

Flagella filament protein (FliC) from *S. enteritidis* wild type was prepared as described by Ibrahim et al., (1985) *J. Clin. Microbiol.* 22: 1040-1044; Vorderviszt, F., (1989) *J. Mol. Biol.* 209: 127-133; and Ogushi et al., (2001) *J. Biol. Chem.* 32: 30521-30526, incorporated herein by reference in their entireties, with some modifications. FIG. 2 is a gel analysis showing the degree of purity of the isolated flagellin.

Immunogenic activity was tested in Balb/c mice. Antiflagellin-specific IgG antibodies were assessed by Elisa. Plates were coated with either recombinant flagellin (prepared as described in Example 1 above) or purified bacterial flagellin, and antibodies were detected with anti-*Salmonella enteritidis* flagellin monoclonal antibody at a 1:100 dilution.

One immunization administered intramuscularly induced very high IgG titers, even at administered concentrations as low as 1 µg. In contrast, intranasal administration demonstrated low, although still detectable, immune responses, as shown in FIG. 3.

Example 3

Flagellin (Monomeric and Polymeric) is an Effective Adjuvant in Vaccine Composition with a Viral Antigen Balb/c female mice were immunized intramuscularly or intranasally with either 1 µg of soluble recombinant (monomeric) flagellin, or 1 µg of soluble polymeric flagellin (isolated from *S. enteritidis* wild type), and co-administered with 10 µg of inactivated H1N1 influenza virus (A/PR/8/34, hereinafter abbreviated as PR8) in a vaccine composition. Inactivated influenza virus alone, administered intramuscularly or intranasally, was used as a control group. Sera were collected retro-orbitally 14 days after immunization and tested for influenza-specific binding IgG antibodies.

Figure 4A:
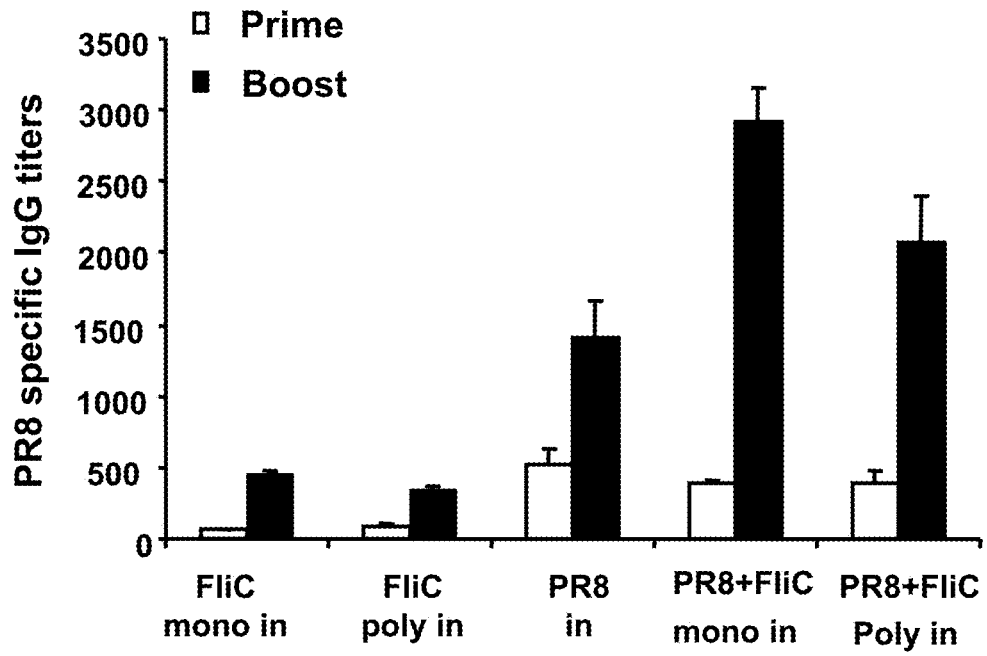
FIG. 4A is a bar graph illustrating the results of immunization of mice intranasally with 10 µg of whole inactivated influenza virus (A/PR/8/34, PR8) combined with 1 µg of polymeric (FliC poly), or monomeric (FliC mono) flagellin.
Figure 4B:
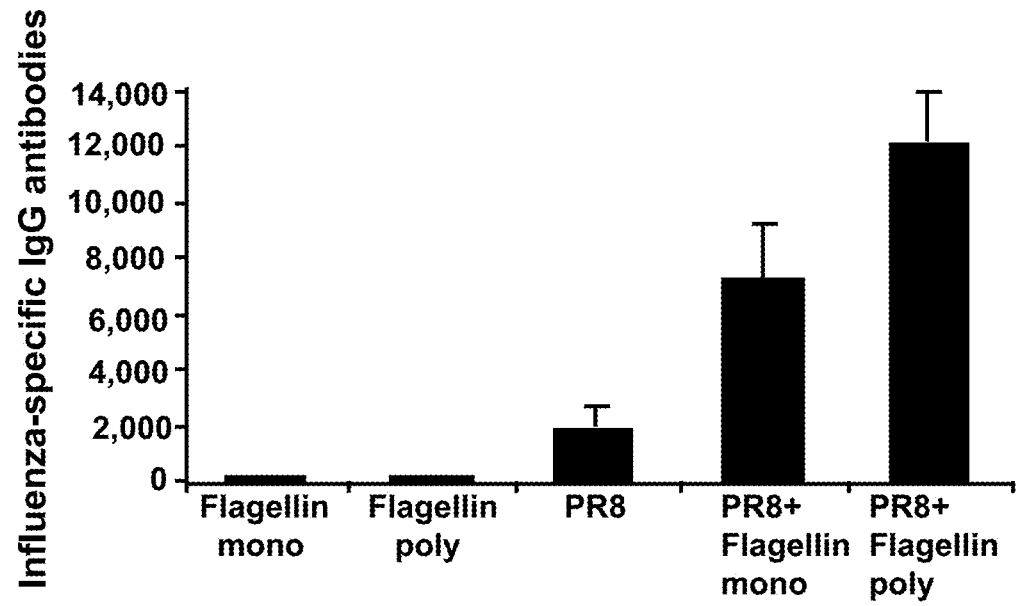
FIG. 4B is a bar graph of results from intramuscular immunization illustrating that inactivated influenza virus mixed with monomeric flagellin induced a 3.5-fold higher antibody titer when compared to inactivated influenza virus vaccine alone. Inactivated influenza virus mixed with the polymeric form of flagellin induced a 6-fold higher IgG level than did the PR8 group, and at least 1.5-fold higher titer than did the vaccine composition of PR8 with monomeric flagellin after a single immunization.

The results from the intramuscular immunization demonstrated that inactivated influenza virus mixed with monomeric flagellin induced 3.5-fold higher antibody titers when compared to inactivated influenza virus vaccine, as shown in FIG. 4B. The data also demonstrated that inactivated influenza virus mixed with the polymeric form of flagellin induced a 6-fold higher IgG level than did the PR8 group, and at least 1.5-fold higher titer than did the vaccine composition of PR8 with monomeric flagellin after a single immunization (FIG. 4B).

The same vaccine compositions administered intranasally with 10 µg of whole inactivated influenza virus (A/PR/8/34, PR8) with 1 µg of polymeric (FliC poly), or monomeric (FliC mono), flagellin, gave about a 1.5 to about 2-fold higher PR8-specific IgG titer than did immunization with influenza antigen alone after 2 immunizations, 4 weeks apart, as shown in FIG. 4A.

Example 4

Cell Lines and Viruses

*Spodoptera frugiperda* Sf9 cells were maintained as suspension cultures in flasks with serum-free SF900 II medium (Gibco-BRL) at 27° C. with stirring at a speed of 80 rpm. Madin-Darby canine kidney (MDCK) cells were cultured in Dulbecco's Modified Eagle's Medium (DMEM) plus 10% fetal bovine serum. Influenza A/PR8 (H1N1) virus was grown in and purified from hen egg embryonic fluid as described by Quan et al., (2007) *J. Virol.* 82:1350-1359, incorporated herein by reference in its entirety. Mouseadapted PR8 and A/Philippines/2/82/X-79 (H3N2) (A/Philippines) viruses were prepared as described by Quan et al., (2007) *J. Virol.* 81:3514-3524, incorporated herein by reference in its entirety.

Example 5

Construction of a Membrane-Anchored Flagellin Gene

Figure 5:
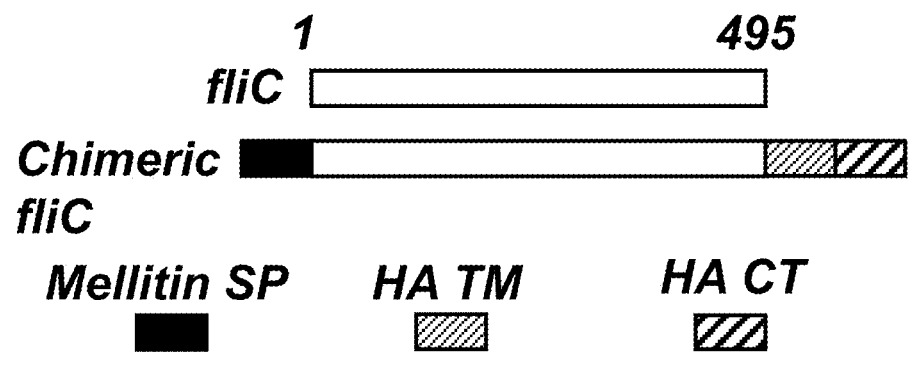

A full-length membrane-anchored flagellin encoding nucleic acid molecule was generated (as schematically illustrated in FIG. 5) by fusing in-frame (i) a signal peptide (SP)-encoding from honeybee melittin, and (ii) the transmembrane (TM) and cytoplasmic tail (CT) regions from the influenza A virus PR8 hemagglutinin (HA), to the 5' and 3' termini of the flagellin gene, respectively. The melittin SP-encoding fragment was PCR amplified from the plasmid M-TM.CT$_{MMTV}$ (described by Wang et al., (2007) *J. Virol.* 81:10869-10878, incorporated herein by reference in its entirety) by use of primers 5'-GGT TCTAGAATGAAATTCTTAGTC-3' (SEQ ID NO.: 1) and 5'-GTGGGATCCT TTCATGTTGATCGG-3' (SEQ ID NO.: 2) (XbaI and BamHI sites are underlined) and cloned into the XbaI/BamHI sites of cloning vector pBluescript (−), resulting in plasmid pBluescript-SP. The *Salmonella enterica* serovar *Typhimurium* flagellin gene (fliC; GenBank accession no. D13689) was amplified from plasmid pEM045 pEF6 FliC stop (Alan Aderem, Institute of Systems Biology, Seattle, Wash.) by using primers 5'-GCA GGATCCATGGCACAAGTCAT-3' (SEQ ID NO.: 3) and 5'-CGCGAATTCACGCAGTAAAGAGAG-3' (SEQ ID NO.: 4) (underlined sites are BamHI and EcoRI, respectively) and inserted into pBluescript-SP, resulting in construct pBluescript-SP-FliC. The nucleic acid sequence encoding the HA TM-CT region was amplified from plasmid pc/pS1 containing the full-length HA gene by using primers 5'-GCTAGAATTCCAGATTCTGG CGATC-3' (SEQ ID NO.: 5) and 5'-GCTAGGGCCCTTATCAGATGCATAT-TCT-3' (SEQ ID NO.: 6) (underlined sites are EcoRI and ApaI, respectively) and inserted into pBluescript-SP-FliC to produce pBluescript-SP-FliC-HA tail.

The full-length membrane anchored flagellin gene was amplified from pBluescript-SP-FliC-HA tail by using primers 5'-GCTCGTCGACATGAAATTCTTAG-3' (SEQ ID NO.: 7) and 5'-GCTACTCGAGT TATCAGATGCATATTC-3' (SEQ ID NO.: 8) (SalI and XhoI sites, respectively, are underlined) and inserted into pFastBac 1 under the control of the polyhedrin promoter.

Primer sequences used in the generation of the membrane-anchored flagellin-encoding nucleic acid constructs are shown in FIG. 6. The nucleotide sequence (SEQ ID NO.: 9) of the membrane-anchored flagellin-encoding nucleic acid was verified, and is shown in FIG. 7. The amino acid sequence (SEQ ID NO.: 10) encoded by the membrane-anchored flagellin-encoding nucleic acid (SEQ ID NO.: 9) is shown in FIG. 8.

Example 6

Generation of rBVs

A recombinant baculovirus vector (rBV) expressing membrane anchored flagellin was derived from the transfer plasmid pFastBac1 (described above in Example 1) by using a Bac-to-Bac expression system (Invitrogen) according to the manufacturer's instructions. rBVs expressing PR8 HA and M1 were described by Quan et al., (2007). J. Virol. 81:3514-3524, incorporated herein by reference in its entirety.

Example 7

Determination of the Cell Surface Expression of Membrane-Anchored Flagellin

The presence of the membrane-anchored flagellin on cell surfaces was determined by a cell surface expression assay. Sf9 cells were seeded in six-well plates at $10^6$ cells/well. The infection with the flagellin-expressing rBV and isotopic labeling were performed as described by Wang et al., (2007) J. Virol. 81:10869-10878, incorporated herein by reference in its entirety. The biotinylation of cell surface proteins and immunoprecipitation were carried out according to Yang & Compans, Virol. (1996) 221:87-97, incorporated herein by reference in its entirety). Final samples were analyzed by sodium dodecyl sulfate-polyacrylamide gel electrophoresis. Gels were dried and then used for autoradiography.

Example 8

Production and Characterization of Chimeric Virus-Like Particles (cVLPs)

Flagellin-containing influenza cVLPs were produced by infection of Sf9 cells with rBVs expressing PR8 HA, M1, and membrane-anchored flagellin. Standard VLPs containing HA/M1, and control VLPs containing M1 only, were produced by infecting Sf9 cell with rBVs expressing PR8 HA and M1 as described by Quan et al., (2007). J. Virol. 81:3514-3524, incorporated herein by reference in its entirety. Cell culture supernatants were collected on day 3 post-infection and cleared by a brief centrifugation (4,000×g for 20 min at 4° C.). VLPs were pelleted by ultracentrifugation at 100,000×g for 1 h at 4° C. The pellets were resuspended in phosphate-buffered saline (PBS) at 4° C. overnight. VLPs were further purified through a 20%-35%-60% discontinuous sucrose gradient at 100,000×g for 1 h at 4° C. The VLP band between 35% and 60% was collected and then diluted with PBS and pelleted at 100,000×g for 1 h at 4° C. VLPs were resuspended in PBS overnight at 4° C. The resulting VLPs were characterized by Western blot analysis (as shown in FIG. 10), hemagglutination activity analysis, and electric microscopic observation (as shown in FIG. 11). For Western blot analysis, HA and M1 bands were probed by mouse anti-HA or M1 polyclonal antibodies. Membrane-anchored flagellin was detected by rabbit anti-flagellin polyclonal antibodies. The flagellin content in cVLPs was estimated by comparison with a standard purified soluble standard flagellin in Western blotting. The hemagglutination activity of VLPs was determined by the capacity to hemagglutinate chicken red blood cells (Quan et al., (2007). J. Virol. 81:3514-3524, incorporated herein by reference in its entirety). For electron microscopy, VLP samples (5 µl to 10 µl; 0.1 mg/ml protein) were examined as described by Wang et al., (2007) J. Virol. 81:10869-10878, incorporated herein by reference in its entirety.

Example 9

Treatment with Glycosidases

N-glycosidase F (PNGase F) and endoglycosidase H (endo-H) (New England Biolabs) were used to determine the glycosylation of membrane-anchored flagellin by following the manufacturer's instructions. Flagellin-containing VLPs (10 µg in a volume of 10 µl) were mixed with 1 µl of denaturing buffer and heated at 100° C. for 10 min. After being cooled in an ice bath for 2 min, samples were mixed with reaction buffer and PNGase F or endo-H and incubated at 37° C. for 1 h. The reaction was terminated by adding sodium dodecyl sulfate-polyacrylamide gel electrophoresis loading buffer, and the mixture was heated at 100° C. for 5 min. Samples were subjected to Western blotting analysis, as shown in FIG. 12.

Example 10

TLR-5-Specific Bioactivity Assay

A RAW264.7 cell-based assay (McDonald et al., (2007). J. Infect. Dis. 195:1607-1617, incorporated herein by reference in its entirety) with modifications was used to determine the bioactivity of membrane-anchored flagellin in VLPs. The RAW264.7 cell line was a mouse macrophage cell line that expressed TLR-2 and -4, but not TLR-5. In brief, 80%-confluent RAW264.7 (TLR-5 negative) cells in a 75-cm² T flask were transfected with 10 µg of plasmid pUNO-hTLR5 expressing the human TLR-5 protein (InvivoGen) by use of the transfection reagent LIPOFECTAMINE™ (Invitrogen) by following the manufacturer's instructions. Six hours post-transfection, cells were removed from the T flask with a cell scraper and seeded into 96-well plates by using $5\times10^4$ cells/well in 100 µl of fresh medium. Non-transfected RAW264.7 cells (TLR-5 negative) were also seeded into 96-well plates for comparison. The TLR-5-positive and TLR-5-negative cells were incubated with 100 µl of serially diluted purified soluble flagellin, flagellin-containing VLPs, or standard HA/M1 VLPs in DMEM, and supernatants were collected after 24 hr. Levels of tumor necrosis factor alpha (TNF-α) production stimulated by soluble flagellin, flagellin-containing VLPs, or standard HA/M1 VLPs in both TLR-5-positive and TLR-5-negative cell cultures were determined by enzyme-linked immunosorbent assay (ELISA), the results of which are shown in FIG. 13. TLR-5 bioactivity was expressed as the level of TNF-α production of TLR-5-positive cells, from which was subtracted that of TLR-5-negative cells stimulated by flagellin, flagellin-containing VLPs, or standard HA/M1 VLPs.

Example 11

Immunization and Challenge

Inbred female BALB/c mice were obtained from Charles River Laboratory. Mouse groups (six mice per group) were immunized twice with 10 µg/mouse of VLPs at 4-week intervals (weeks 1 and 4). For virus challenge, mice were anesthetized with isoflurane and infected with 40 times the 50% lethal dose ($40 \times LD_{50}$) ($LD_{50} \times 50$ PFU/mouse) of mouse-adapted A/PR8 virus (2,000 PFU) or $40 \times LD_{50}$ ($LD_{50} \times 25$ PFU/mouse) of mouse-adapted A/Philippines virus (1,000 PFU) in 50 µl of PBS per mouse 4 weeks after the boosting immunization. For the determination of lung virus titers, six mice from each group were sacrificed on day 4 post-challenge. Blood samples were collected on weeks 0, 3, and 7 by retro-orbital plexus puncture. After clotting and a brief centrifugation, serum samples were collected and stored at −80° C. prior to use for assays.

Example 12

Antibody Titration

The influenza virus-specific serum antibody endpoint titers, including those for immunoglobulin G (IgG) and subtypes (IgG1, IgG2, and IgG2b), were determined by ELISA as described by Quan et al., (2007). J. Virol. 81:3514-3524, incorporated herein by reference in its entirety. In brief, 96-well microtiter plates (Nunc Life Technologies) were coated with 100 µl/well of inactivated PR8 virus (5 µg/ml) in PBS overnight at 4° C. For serum IgG titers against the heterologous A/Philippines virus (H3N2), plates were coated with 100 µl/well of inactivated A/Philippines virus (5 µg/ml). The serum samples were serially diluted in twofold steps. After being washed and blocked with 1.5% bovine serum albumin, plates were used to bind antibody with the diluted sera. The detection color was developed by binding horseradish peroxidase-labeled goat anti-mouse IgG, IgG1, IgG2a, or IgG2b (Southern Biotechnology) at 37° C. for 1 h. After extensive washing, the substrate TMB (Zymed, Invitrogen) was applied. The optical density at 450 nm ($OD_{450}$) was read using an ELISA reader (model 680; Bio-Rad). The highest dilution which gave an $OD_{450}$ twice that of the naive group without dilution was designated as the antibody endpoint titer. Results are shown in FIGS. 14A-14D.

Example 13

Virus Neutralization and HI Assays

A neutralization assay was performed using MDCK cells as described by Quan et al., (2007). J. Virol. 81:3514-3524, incorporated herein by reference in its entirety. Hemagglutination inhibition (HI) assays were carried out as described by Compans, R. W. (1974) J. Virol. 14:1307-1309, incorporated herein by reference in its entirety, with modifications. Briefly, 8 hemagglutination units of PR8 or A/Philippines virus were mixed with serially diluted receptor-destroying enzyme-pretreated serum samples in a total volume of 50 µl and incubated at 37° C. for 1 h. An equal volume of chicken blood cells (0.5%) was mixed with the virus-serum mixture and incubated at 25° C. for 30 min. HI titers were recorded. Results are shown in FIGS. 15A-16B.

Example 14

Cytokine Assays

Interleukin-2 (IL-2), gamma interferon (IFN-γ), TNF-α, and IL-4 levels were determined by ELISA (eBioscience, San Diego, Calif.) according to the manufacturer's instructions. Splenocytes ($1 \times 10^6$ cells) isolated from immunized mice were seeded into 96-well issue culture plates and stimulated with a mixture of two major histocompatibility complex class I (MHC-I) HA peptides (IYSTVASSL (SEQ ID NO.: 11) and LYEKVKSQL (SEQ ID NO.: 12)) or a pool of five MHC-II HA peptides (SFERFEIFPKE (SEQ ID NO.: 13), HNTNGVTAACSH (SEQ ID NO.: 14), CPKYVRSAKLRM (SEQ ID NO.: 15), KLKNSYV NKKGK (SEQ ID NO.: 16), and NAYVSWTSKYN RRF (SEQ ID NO.: 17)) (shown in FIG. 17) at a concentration of 10 µg/ml. The plates were incubated at 37° C. for 2 days, and cell culture supernatants were collected for cytokine assays, the results of which are shown in FIGS. 18A-18D.

Example 15

Figure 21:
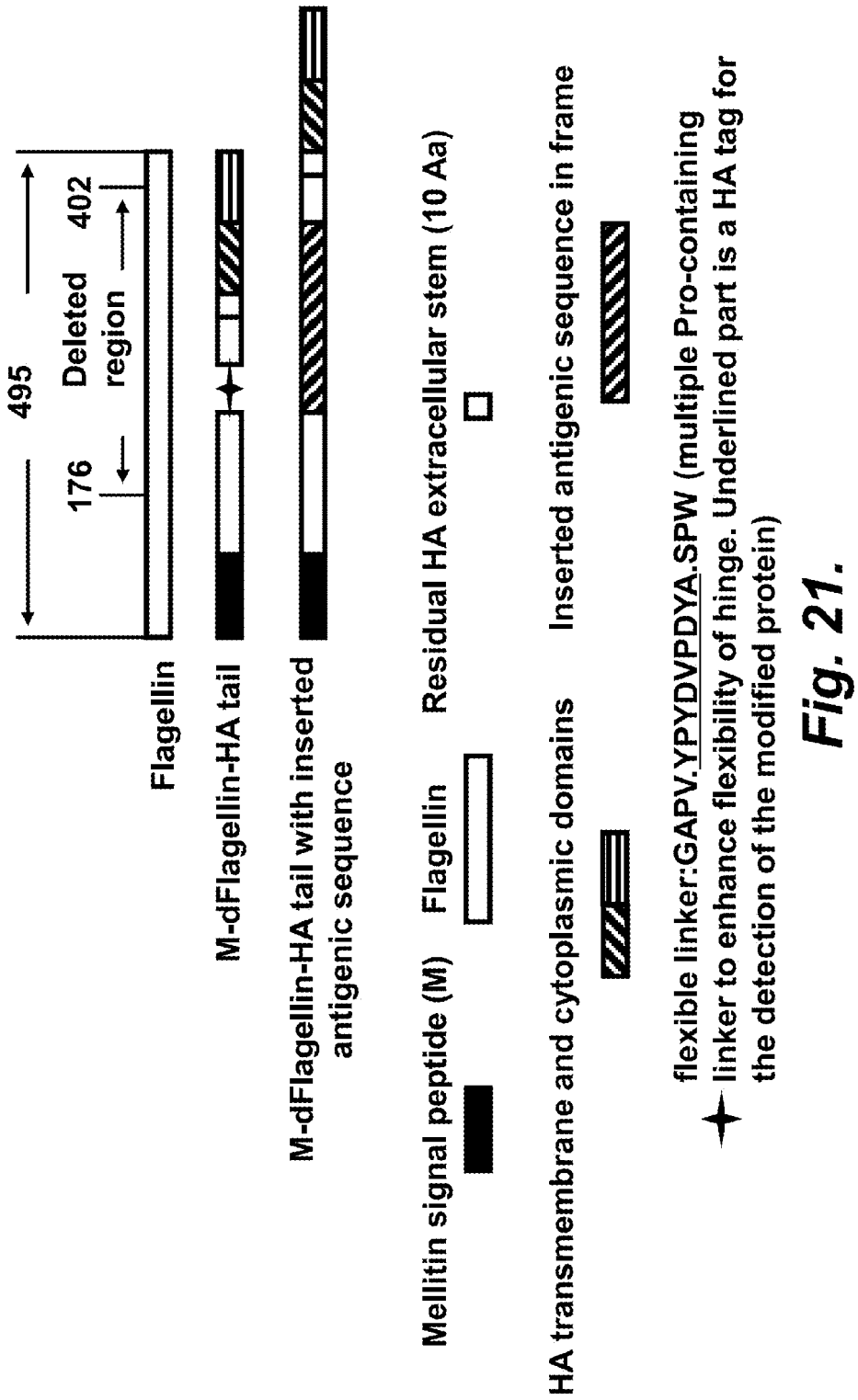
FIG. 21 illustrates modified flagellin variants with an influenza HA membrane anchor peptide.

Modified Bacterial Flagellin Adjuvants (i) Modified Flagellin with influenza HA membrane anchor, as shown in FIG. 21. Referring to FIG. 21, a full-length native *Salmonella* flagellin polypeptide contains 495 amino acids. Modified flagellins and have a deletion of amino acids 176 to 402 inclusive, but include, as heterologous polypeptide sequences fused in-frame, a melittin signal peptide, and an influenza HA transmembrane-cytoplasmic domain (TM-CT). In the variant M-dFlagellin-HA tail (2, FIG. 21), amino acids from 176-402 are deleted and replaced with a hinge peptide having the sequence GAPY-PYDVPDYASPW (SEQ ID NO.: 18). In (3), a heterologous peptide sequence replaces the deleted fragment.

Figure 22:
FIG. 22 illustrates modified flagellin variants with a mouse mammary tumor virus (MMTV) Env membrane anchor.

(ii) Referring to FIG. 22, another modified flagellin includes a mouse mammary tumor virus (MMTV) Env membrane anchor. Full-length native *Salmonella* flagellin polypeptide (1) contains 495 amino acids. Modified flagellins (2) and (3) have a deletion of amino acids 176 to 402 inclusive, but include, as heterologous polypeptide sequences fused in-frame, a melittin signal peptide, and MMMTV Env transmembrane and cytoplasmic domains. In the M-dFlagellin-MMTV tail (2), amino acids from 176-402 are deleted and replaced with a flexible hinge GAPYPYD-VPDYASPW (SEQ ID NO.: 18). In (3), a heterologous peptide replaces the deleted fragment.

Figure 23:
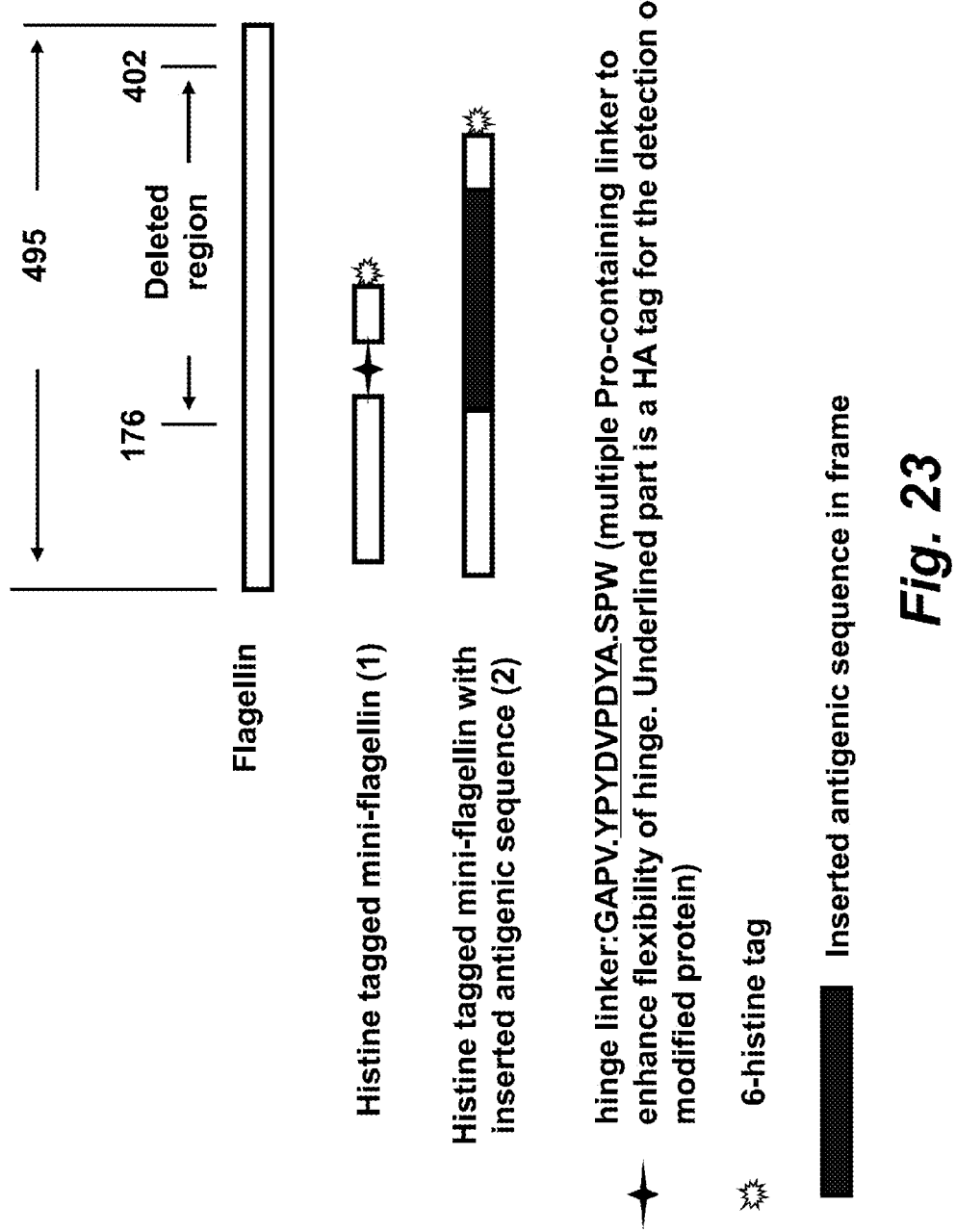
FIG. 23 illustrates modified flagellin variants with an influenza HA membrane anchor peptide and a hexahistidine tag is fused to C-terminus.

(iii) Referring to FIG. 23, a full-length native *Salmonella* flagellin polypeptide (1) contains 495 amino acids. Modified flagellins (2) and (3) have a deletion of amino acids 176 to 402 inclusive, but include, as heterologous polypeptide sequences fused in-frame, a melittin signal peptide, and an influenza HA transmembrane-cytoplasmic domain (TM-CT). In the variant M-dFlagellin-HA tail (2, FIG. 21), amino acids from 176-402 are deleted and replaced with a hinge peptide having the sequence GAPYPYDVPDYASPW (SEQ ID NO.: 18). In (3), a heterologous peptide sequence replaces the deleted fragment. Additionally, the variant flagellins are His-tagged modified flagellins that further include a hexahistidine tag fused to the C-terminus of the modified flagellin.

Example 16

Figure 25:
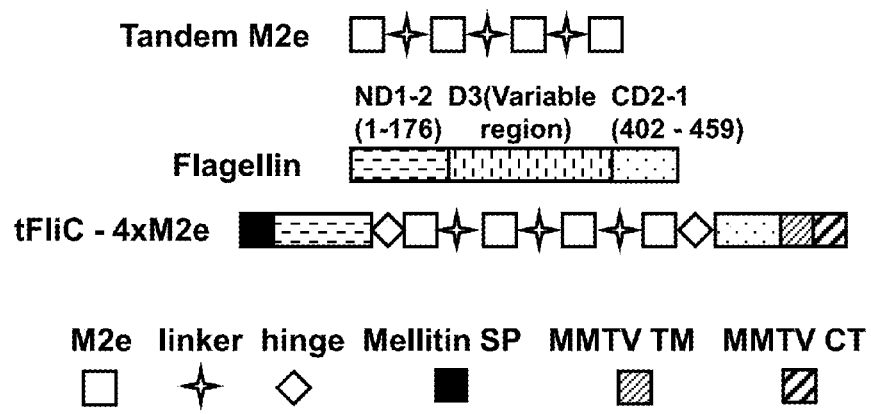
FIG. 25 is a schematic diagram of membrane-anchored flagellin with a tandem of four repeats of M2e (SEQ ID NO.: 19) inserted (tFliC-4×M2e).
Figure 26:
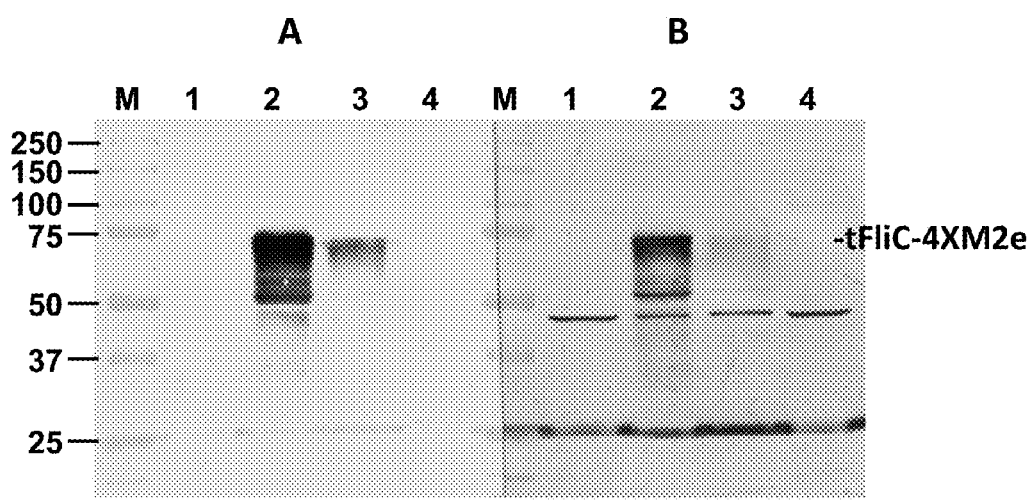
FIG. 26 is a digital image of a stained gel analysis of cellular and cell surface expression of membrane-anchored flagellin with M2e inserted therein.

As shown in FIGS. 25 and 26, a membrane-anchored flagellin was constructed having a tandem of four repeats of M2e having sequence SEQ ID NO.: 19 and substituting for the region of the flagellin between the amino acid positions of 176 and 402 (tFliC-4×M2e). Expression of the inserted region, as shown in FIG. 26, was shown in insect cells.

Insect cells were infected with rBV expressing membrane-anchored flagellin with tandem M2e sequences inserted (lanes 2 and 3) or mock rBV (lanes 1 and 4). Lanes 1 and 2, infected cells were lysed and applied to a Western blot 2 days postinfection. Lanes 3 and 4, infected cells were labeled by surface-protein biotinylation 2 days postinfection. Cell lysates were precipitated by immobilized neutravidin. Precipitates were dissolved in SDS-PAGE loading buffer and applied to Western blot. A, protein bands were probed by anti-flagellin antibody; B, Protein bands were probed with anti-M2e antibody.

The invention claimed is:

1. The nucleic acid molecule, comprising:
   a region encoding a chimeric bacterial flagellin, wherein the chimeric bacterial flagellin has an N-terminal flagellin domain, a C-terminal flagellin domain, a deleted flagellin central variable domain and a heterologous antigenic peptide inserted in the deleted central variable domain such that the antigenic peptide is between the N-, and C-terminal domains of flagellin, wherein the chimeric flagellin is capable of specifically interacting with a Toll-like receptor of an animal or human cell,
   a region encoding a heterologous signal peptide; and
   a region encoding a transmembrane-cytoplasmic tail capable of being incorporated into a virus-like particle or virosome.

2. The nucleic acid molecule of claim 1, wherein the heterologous antigenic peptide encodes a viral antigen.

3. The nucleic acid molecule of claim 1, wherein the heterologous signal peptide is a bee melittin signal peptide.

4. The nucleic acid molecule of claim 1, comprising:
   a first nucleotide sequence encoding an amino acid sequence from amino acid positions of about 1 to about 305 of sequence SEQ ID NO.: 10, or a conservative variant thereof;
   a second nucleotide sequence encoding an amino acid sequence from amino acid positions about 430 to about 565 of sequence SEQ ID NO.: 10, or a conservative variant thereof; and
   a third nucleotide sequence disposed between the first nucleotide sequence and the second nucleotide sequence, wherein the third nucleotide sequence encodes a heterologous antigenic peptide.

5. The nucleic acid molecule of claim 1, wherein the nucleic acid molecule is operably inserted into a nucleic acid expression vector.

6. The nucleic acid molecule of claim 5, wherein the nucleic acid expression vector is selected from the group consisting of: a plasmid, a baculovirus vector, a cosmid, a viral vector, a chromosome, a mini-chromosome, a modified vaccinia Ankara (MVA) vector, a recombinant poxvirus vector, a recombinant adenovirus vector, an alphavirus vector, and a paramyxovirus vector.

* * * * *